United States Patent
Sasaki et al.

(10) Patent No.: US 8,927,718 B2
(45) Date of Patent: Jan. 6, 2015

(54) FUSED HETEROCYCLIC RING DERIVATIVE AND USE THEREOF

(75) Inventors: Satoshi Sasaki, Kanagawa (JP); Yuta Tanaka, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 129 days.

(21) Appl. No.: 13/391,799

(22) PCT Filed: Aug. 25, 2010

(86) PCT No.: PCT/JP2010/064414
§ 371 (c)(1),
(2), (4) Date: Apr. 27, 2012

(87) PCT Pub. No.: WO2011/024873
PCT Pub. Date: Mar. 3, 2011

(65) Prior Publication Data
US 2012/0208794 A1  Aug. 16, 2012

(30) Foreign Application Priority Data

Aug. 26, 2009  (JP) .................................. 2009-195784

(51) Int. Cl.
C07D 471/04 (2006.01)
A61K 31/437 (2006.01)

(52) U.S. Cl.
CPC .................................. *C07D 471/04* (2013.01)
USPC ........................................ 546/113; 514/300

(58) Field of Classification Search
USPC ......................................... 546/113; 514/300
See application file for complete search history.

(56) References Cited

U.S. PATENT DOCUMENTS

| 6,159,962 | A | 12/2000 | Steiner et al. |
|---|---|---|---|
| 6,387,912 | B1 | 5/2002 | Steiner et al. |
| 2002/0068756 | A1 | 6/2002 | Labelle et al. |
| 2003/0181420 | A1 | 9/2003 | Bayne et al. |
| 2003/0203909 | A1 | 10/2003 | Ushio et al. |
| 2005/0080111 | A1 | 4/2005 | Bayne et al. |
| 2007/0213323 | A1 | 9/2007 | Imogai et al. |
| 2007/0232661 | A1 | 10/2007 | Beachy et al. |
| 2008/0119488 | A1 | 5/2008 | Bayne et al. |
| 2008/0193423 | A1 | 8/2008 | Brunton et al. |
| 2008/0194637 | A1 | 8/2008 | Brunton et al. |
| 2008/0280900 | A1 | 11/2008 | Pajouhesh et al. |
| 2009/0048286 | A1 | 2/2009 | Lee et al. |
| 2009/0227561 | A1 | 9/2009 | Fujii et al. |
| 2010/0056582 | A1 | 3/2010 | Bayne et al. |
| 2011/0053915 | A1 | 3/2011 | Ivaschenko et al. |
| 2012/0214795 | A1 | 8/2012 | Banno et al. |

FOREIGN PATENT DOCUMENTS

| EP | 2 471 793 | 7/2012 |
|---|---|---|
| JP | 2002-504103 | 2/2002 |
| JP | 2002-534465 | 10/2002 |
| WO | 01/64639 | 9/2001 |
| WO | 02/12189 | 2/2002 |
| WO | 03/059884 | 7/2003 |
| WO | 2005/033288 | 4/2005 |
| WO | 2005/081960 | 9/2005 |
| WO | 2006/030032 | 3/2006 |
| WO | WO 2007085188 A1 * | 8/2007 |
| WO | 2008/057468 | 5/2008 |
| WO | 2008/057469 | 5/2008 |
| WO | 2008/138126 | 11/2008 |
| WO | 2009/077956 | 6/2009 |
| WO | 2009/107850 | 9/2009 |

OTHER PUBLICATIONS

Banker (Modern Pharmaceutics) Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
STN-Chemical database, Registry RN 421562-47-2, Thieno[2,3-d]pyrimidine-6-carboxamide, 3,4-dihydro-N,2,3,5-tetramethyl-4-oxo-N-(phenylmethyl)-, May 24, 2002.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Yang, et al., "Converse Conformational Control of Smoothened Activity by Structurally Related Small Molecules", Journal of Biological Chemistry, vol. 284, No. 31, Jul. 2009, pp. 20876-20884.

* cited by examiner

*Primary Examiner* — David K O Dell
(74) *Attorney, Agent, or Firm* — Hamre, Schumann, Mueller & Larson, P.C.

(57) ABSTRACT

The present invention provides a fused heterocycle derivative having a strong Smo inhibitory activity, and use thereof.
Specially, the present invention relates to a compound represented by the formula

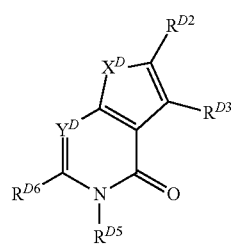

(DI)

wherein each symbol is as defined in the specification, or salt thereof, and a medicament containing the compound or a prodrug thereof, which is an Smo inhibitor or an agent for the prophylaxis or treatment of cancer.

10 Claims, No Drawings

SEQUENCE LISTING

```
<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
gaagatctgc cagcccaggc tccggggc                                        28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cccaagcttc tgcccgcaca gccctgctc                                       29

<210> SEQ ID NO 3
<211> LENGTH: 88
<212> TYPE: DNA
<213> ORGANISM: Artificial Sequence
<220> FEATURE:
<223> OTHER INFORMATION: primer

<400> SEQUENCE: 3
ggggtaccga ccacccagac cacccagacc acccagacca cccagaccac ccagaccacc     60
cagaccaccc agaccaccca agatcttc                                        88

<210> SEQ ID NO 4
<211> LENGTH: 88
<212> TYPE: DNA
<213> ORGANISM: Artificial Sequence
<220> FEATURE:
<223> OTHER INFORMATION: primer

<400> SEQUENCE: 4
gaagatcttg ggtggtctgg gtggtctggg tggtctgggt ggtctgggtg gtctgggtgg     60
tctgggtggt ctgggtggtc ggtacccc                                        88

<210> SEQ ID NO 5
<211> LENGTH: 20
<212> TYPE: DNA
<213> ORGANISM: Artificial Sequence
```

```
<220> FEATURE:
<223> OTHER INFORMATION: primer

<400> SEQUENCE: 5
ctgggtgggg atcggagaca                                              20

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gcgctttccc atcagttcct tatt                                         24

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
ggggtaccat gctgctgctg ctggcca                                      27

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
gctctagatc agctggactt gaccgcca                                     28

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atgctgctgc tgctggccag                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tcagccgccg gatttggccg                                              20
```

FUSED HETEROCYCLIC RING DERIVATIVE AND USE THEREOF

TECHNICAL FIELD

The present invention relates to a fused heterocycle derivative and use thereof. More particularly, the present invention relates to a compound having a strong Smo inhibitory activity and useful for the prophylaxis or treatment of cancer and the like, and use thereof.

BACKGROUND OF THE INVENTION

The study of morphogenesis during the developmental stage has been conducted based on the screening of variant using *Drosophila*. Hedgehog gene (hh) was found as one of the genes that cause morphological abnormality of *Drosophila* embryo due to mutation thereof. Hedgehog gene product (Hh) is a secretory protein, which is produced as an about 45 kDa precursor and then divided, due to autolysis, into a 20 kDa N-terminal side domain, which is a main active principle, and a 25 kDa C-terminal side domain. The 20 kDa N-terminal side domain, which is a main active principle, is modified by fatty acid on the N-terminal and cholesterol on the C-terminal thereof. The Hedgehog signal transduction system is formed by the protein group described below. Hh receptor is Patched (Ptch), which is a twelve-transmembrane-type protein. Ptch acts on Smoothened (Smo), which is a seven-transmembrane-type protein, and suppresses the function of Smo in the absence of Hh. When Hh is bound to the receptor Ptch, suppression of Smo is released and Smo is activated. The signal produced by the activation of Smo activates transcription factor Ci, which regulates the expression of the gene group involved in the morphogenesis (Curr. Opin. Genet. Dev., vol. 12, pages 503-511, 2002).

A pathway corresponding to the *Drosophila* Hedgehog signal transduction system has been confirmed also in mammals. In human, for example, three types of gene products, sonic hedgehog (Shh), indian hedgehog (Ihh) and desert hedgehog (Dhh), are known to correspond to *Drosophila* Hh, and undergo post-translational modification as in *Drosophila* Hh (Cell, vol. 103, pages 371-374, 2000). In human Shh, a 19 kDa active principle is cleaved out from a 45 kDa precursor protein by autolysis, and fatty acid is added to the N-terminal thereof, and cholesterol is added to the C-terminal thereof (J. Biol. Chem., vol. 273, pages 14037-14045, 1998). Such modification is considered to be essential for the maintenance of Shh activity and, for example, 40 times enhanced activity was achieved by the addition of palmitic acid to *Escherichia coli* recombinant human Shh free of N-terminal modification with fatty acid, and 160 times enhanced activity was achieved by the addition of myristic acid thereto (Biochemistry, vol. 40, pages 4359-4371, 2001). On the other hand, as a human gene corresponding to *Drosophila* Smo, human Smo is known, and as a human gene corresponding to *Drosophila* Ptch, 2 types of Ptch1 and Ptch2 are known. In addition, a transcription factor corresponding to *Drosophila* Ci is considered to be Gli in human, and 3 types of Gli1, Gli2 and Gli3 are known (Nature Rev. Cancer, vol. 2, pages 361-372, 2002). Shh/Ihh/Dhh are each bound to Ptch1 and activate Smo by inhibiting the bond between Ptch1 and Smo. Shh/Ihh/Dhh are also bound to Ptch2, Hip1, Gas1 and Cdo/Boc, besides Ptch1, and regulate the activation of Smo. A signal transduction from Smo induces nuclear localization of Gli1 and Gli2, and activate transcription of Gli1 (Curr. Opin. Cell Biol., vol. 19, pages 159-165, 2007).

The Hedgehog signal is involved in the morphogenesis in the developmental stages also in mammals. In human, for example, patients with Holoprosencephaly, which is a congenital developmental abnormality, showed mutation in Shh (Nat. Genet., vol. 14, pages 357-360, 1996). Moreover, a natural compound Cyclopamine derived from white hellebore known as a compound inducing Cyclopus in sheep (Am. J. Vet. Res., vol. 24, pages 1164-1175, 1963) was confirmed to inhibit Smo as action mechanism thereof (Development, vol. 125, pages 3553-3562, 1998). Furthermore, an Shh knockout mouse was prepared, and its phenotype was found to include Cyclopus, malformation of extremities (Nature, vol. 383, pages 407-413, 1996), and neural plate malformation (Cell, vol. 111, pages 63-75, 2002).

Hedgehog signal is inherently a developmental signal, which is promoted in tumor tissues and functions as a cancer cell proliferation and survival signal. Hedgehog signal is considered to function for the growth and survival of cancer cells in an autocrine mode, or function between cancer cells and cancer interstitial cells in a paracrine mode, in tumor tissues (Nat. Rev. Drug Discov., vol. 5, pages 1026-1033, 2006). In an autocrine mode, it works for the growth and maintenance of cancer cells, via transcription activation by Gli-1, by abnormal cell cycle control due to increased expression of Cyclin D and decreased expression of p21, promotion of proliferation signal by activation of EGFR pathway and the like. On the other hand, since Shh expressed in cancer cells acts on Smo in cancer interstitial cells, growth factors such as insulin-like growth factor-1, fibroblast growth factor, platelet-derived growth factor and the like are transmitted from cancer interstitial cells to cancer cells, and function for the growth and survival of cancer cells. It is also considered that promotion of VEGF, PDGF pathway and the like by Gli-1 promotes tumor angiogenesis (Clin Cancer Res., vol. 12, pages 5924-5928, 2006). As to the mechanism of promotion of Hedgehog signal, a cancer in which Hedgehog signal is promoted due to mutation of Ptch1 and a cancer which is promoted by overexpression of Shh, which is one of the ligands, have been reported (Nature Rev. Cancer, vol. 3, pages 903-911, 2003). As a cancer in which Hedgehog signal is promoted due to mutation, basal cell cancer and medulloblastoma are known, and mutation of Ptch1 observed in these cancers activates Hedgehog signal in a ligand independent manner (Am. J. Med. Gen., vol. 123A, pages 5-28, 2003). As a cancer in which Hedgehog signal is promoted by overexpression of Shh, pancreatic cancer (Nature, vol. 425, pages 846-851, 2003) and the like have been reported. In a transgenic mouse in which Shh is forcedly expressed in the pancreas, Hedgehog signal is suggested to be involved not only in the growth and maintenance of cancer, but also carcinogenic process, since a PanIN-like lesion in the initial stages of cancer progress was found in the pancreas (Nature, vol. 425, pages 851-856, 2003). Furthermore, Hedgehog signal is considered to function for the growth and survival of cancer stem cells, and play a key role in the metastasis or postoperative recurrence of tumor and the like (Trends Cell Biol., vol. 17, pages 438-447, 2007).

As the Hedgehog signal inhibitor, the following are known. Cyclopamine, which is a naturally occurring Smo inhibitory compound, has been reported to show a tumor growth suppressive effect on glioma (Development, vol. 128, pages 5201-5212, 2001) and the like. As a synthetic low-molecular-weight compound inhibiting Smo, CUR-61414 (Proc. Natl. Acad. Sci. U.S.A., vol. 100, pages 4616-4621, 2003) and SANT-1, 2, 3, 4 (Proc. Natl. Acad. Sci. U.S.A., vol. 99, pages 14071-14076, 2002) have been reported. As for the Hedgehog signal inhibitory antibody, it has been reported that administration of an anti-Shh antibody to a cancer-carrying nude mouse transplanted with colorectal cancer cell line HT-29 caused regression of cancer (WO 2004/020599).

Patent documents 1 to 5 and non-patent documents 1 to 2 disclose fused heterocycle compounds.

DOCUMENT LIST

Patent Documents

Patent Document 1: WO 01/64639
Patent Document 2: WO 02/12189
Patent Document 3: WO 03/059884
Patent Document 4: WO 2005/081960
Patent Document 5: WO 2006/030032

Non-Patent Documents

Non-Patent Document 1: Russian Journal of Organic Chemistry, vol. 38, pages 419-423, 2002
Non-Patent Document 2: CAS registry number: 858744-76-0

SUMMARY OF THE INVENTION

Problems to be Solved by the Invention

An object of the present invention is to provide a compound having a superior Smo inhibitory activity, low toxicity and sufficiently satisfactory as a pharmaceutical product.

Means of Solving the Problems

The present inventors have conducted intensive studies in an attempt to solve the above-mentioned problems and found that a compound represented by the following formula and a salt thereof have a superior Smo inhibitory activity, which resulted in the completion of the present invention.

Accordingly, the present invention provides the following.
[1] a compound represented by the formula

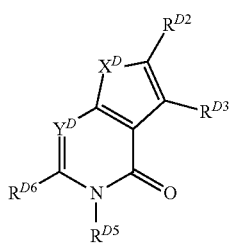

(DI)

wherein
$X^D$ is $NR^{D1}$, a sulfur atom or an oxygen atom;
$Y^D$ is $CR^{D7}$ or a nitrogen atom;
$R^{D1}$ is a hydrogen atom or a $C_{1-6}$ alkyl group;
$R^{D2}$ is a carbamoyl group optionally having substituent(s);
$R^{D3}$ is a halogen atom, a $C_{1-6}$ alkyl group optionally having substituent(s), a $C_{2-6}$ alkenyl group optionally having substituent(s), an amino group optionally having substituent(s), a mercapto group optionally having a substituent, a cyclic group optionally having substituent(s) or a cyano group;
$R^{D5}$ is a $C_{1-6}$ alkyl group optionally having substituent(s) or a cyclic group optionally having substituent(s);
$R^{D6}$ is a hydrogen atom, a halogen atom or a $C_{1-6}$ alkyl group; and $R^{D7}$ is a hydrogen atom, a halogen atom or a $C_{1-6}$ alkyl group, or a salt thereof (in the present specification, sometimes to be abbreviated as "compound (DI)");
[2] the compound or salt of the above-mentioned [1], wherein $X^D$ is $NR^{D1}$ wherein $R^{D1}$ is a hydrogen atom or a $C_{1-6}$ alkyl group;
$Y^D$ is $CR^{D7}$ wherein $R^{D7}$ is a hydrogen atom, a halogen atom or a $C_{1-6}$ alkyl group;
$R^{D2}$ is a carbamoyl group optionally having 1 or 2 substituents selected from
(1) a $C_{1-6}$ alkyl group optionally having substituent(s),
(2) a $C_{2-6}$ alkynyl group optionally having substituent(s),
(3) a $C_{3-8}$ cycloalkyl group optionally having substituent(s), and
(4) a heterocyclic group optionally having substituent(s);
$R^{D3}$ is a $C_{1-6}$ alkyl group or a $C_{2-6}$ alkenyl group;
$R^{D5}$ is
(1) a $C_{1-6}$ alkyl group optionally having substituent(s),
(2) a $C_{6-10}$ aryl group optionally having substituent(s), or
(3) a heterocyclic group optionally having substituent(s); and
$R^{D6}$ is a $C_{1-6}$ alkyl group;
[3] the compound or salt of the above-mentioned [2], wherein $X^D$ is $NR^{D1}$ wherein $R^{D1}$ is methyl, and $Y^D$ is $CR^{D7}$ wherein $R^{D7}$ is a hydrogen atom;
[4] 3,6-diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof;
[5] 3-ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof;
[6] 6-ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof;
[7] a prodrug of the compound or salt of any of the above-mentioned [1] to [6];
[8] a medicament comprising the compound or salt of any of the above-mentioned [1] to [6] or a prodrug thereof;
[9] the medicament of the above-mentioned [8], which is an Smo inhibitor;
[10] the medicament of the above-mentioned [8], which is an agent for the prophylaxis or treatment of cancer;
[11] a method for the prophylaxis or treatment of cancer in a mammal, which comprises administering an effective amount of the compound or salt of any of the above-mentioned [1] to [6] or a prodrug thereof to the mammal; and
[12] use of the compound or salt of any of the above-mentioned [1] to [6] or a prodrug thereof for the production of an agent for the prophylaxis or treatment of cancer.

Effect of the Invention

Since the compound of the present invention has a strong Smo inhibitory action, it can provide a clinically useful agent for the prophylaxis or treatment of cancer, a cancer growth inhibitor and a cancer metastasis suppressive agent.

DETAILED DESCRIPTION OF THE INVENTION

The present invention is explained in detail in the following.

In the present specification, the "halogen atom" means a fluorine atom, a chlorine atom, a bromine atom or an iodine atom.

In the present specification, the "$C_{1-6}$ alkyl group" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl group" means, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl group" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{1-6}$ alkoxy group" means, for example, methoxy, ethoxy, propoxy, isopropoxy, butoxy, isobutoxy, sec-butoxy, tert-butoxy, pentoxy, isopentoxy, hexoxy or the like.

In the present specification, the "$C_{1-6}$ alkyl-carbonyl group" means, for example, acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl or the like.

In the present specification, the "$C_{1-6}$ alkoxy-carbonyl group" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{3-8}$ cycloalkyl group" means, for example, cyclopropyl, cyclobutyl, cyclopentyl, cyclohexyl, cycloheptyl, cyclooctyl or the like.

In the present specification, the "$C_{3-8}$ cycloalkane" means, for example, cyclopropane, cyclobutane, cyclopentane, cyclohexane, cycloheptane, cyclooctane or the like.

In the present specification, the "$C_{3-6}$ cycloalkane" means, for example, cyclopropane, cyclobutane, cyclopentane, cyclohexane or the like.

In the present specification, the "$C_{3-8}$ cycloalkenyl group" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{6-10}$ aryl group" means, for example, phenyl, 1-naphthyl, 2-naphthyl or the like.

In the present specification, the "$C_{6-10}$ arene" means, for example, benzene, naphthalene or the like.

In the present specification, the "$C_{7-13}$ aralkyl group" means, for example, benzyl, phenethyl, naphthylmethyl or the like.

In the present specification, the "$C_{6-10}$ aryl-carbonyl group" means, for example, benzoyl, 1-naphthoyl, 2-naphthoyl or the like.

In the present specification, the "heterocyclic group" means an aromatic heterocyclic group (e.g., a 5- to 12-membered aromatic heterocyclic group) or a non-aromatic heterocyclic group (e.g., a 4- to 12-membered non-aromatic heterocyclic group).

In the present specification, the "aromatic heterocyclic group" means a monocyclic aromatic heterocyclic group and a fused aromatic heterocyclic group.

Examples of the monocyclic aromatic heterocyclic group include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-6-yl) and the like.

Examples of the fused aromatic heterocyclic group include a 8- to 12-membered fused aromatic heterocyclic group, specifically, a group derived from a fused ring wherein a ring corresponding to the above-mentioned 5- to 7-membered monocyclic aromatic heterocyclic group and a $C_{6-10}$ arene are condensed; and a group derived from a fused ring wherein rings corresponding to the above-mentioned 5- to 7-membered monocyclic aromatic heterocyclic groups are condensed. Specific examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 3-benzisoxazolyl), benzothiazolyl (e.g., 2-benzothiazolyl), benzoisothiazolyl (e.g., 3-benzoisothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), isoindolyl (e.g., isoindol-1-yl, isoindol-2-yl, isoindol-3-yl, isoindol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group and a fused non-aromatic heterocyclic group.

Examples of the monocyclic non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom. Examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), dihydropyranyl (e.g., 2,3-dihydropyran-2-yl, 2,3-dihydropyran-3-yl), tetrahydropyranyl (e.g., 2-tetrahydropyranyl, 3-tetrahydropyranyl, 4-tetrahydropyranyl), thiopyranyl (e.g., 4-thiopyranyl), dihydrothiopyranyl (e.g., dihydrothiopyran-3-yl, dihydrothiopyran-4-yl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., tetrahydropyridin-1-yl, tetrahydropyridin-2-yl, tetrahydropyridin-3-yl, tetrahydropyridin-4-yl) and the like.

Examples of the fused non-aromatic heterocyclic group include a 8- to 12-membered fused non-aromatic heterocyclic group, specifically, a group derived from a fused ring wherein a ring corresponding to the above-mentioned 4- to 7-membered monocyclic non-aromatic heterocyclic group and a $C_{6-10}$ arene are condensed; a group derived from a fused ring wherein rings corresponding to the above-mentioned 4- to 7-membered monocyclic non-aromatic heterocyclic groups are condensed; a group derived from a fused ring wherein a ring corresponding to the above-mentioned 4- to 7-membered monocyclic non-aromatic heterocyclic group and a ring corresponding to the above-mentioned 5- to 7-membered monocyclic aromatic heterocyclic group are condensed; and a group wherein the above-mentioned group is partially saturated. Specific examples thereof include dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), azabicyclohexyl (e.g., 2-azabicyclo[3.1.0]hexan-3-yl) and the like.

In the present specification, the "heterocycle" means an aromatic heterocycle (e.g., a 5- to 12-membered aromatic heterocycle) or a non-aromatic heterocycle (e.g., a 4- to 12-membered non-aromatic heterocycle).

In the present specification, the "aromatic heterocycle" means a monocyclic aromatic heterocycle and a fused aromatic heterocycle.

Examples of the monocyclic aromatic heterocycle include a 5- to 7-membered (preferably 5- or 6-membered) monocyclic aromatic heterocycle containing, as a ring-constituting atom besides carbon atoms, 1 to 4 hetero atoms selected from an oxygen atom, a sulfur atom (optionally oxidized) and a nitrogen atom (optionally oxidized). Examples thereof include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

Examples of the fused aromatic heterocycle include a 8- to 12-membered fused aromatic heterocycle, specifically, a fused ring wherein the above-mentioned 5- to 7-membered monocyclic aromatic heterocycle and a $C_{6-10}$ arene are condensed; and a fused ring wherein the above-mentioned 5- to 7-membered monocyclic aromatic heterocycles are condensed. Specific examples thereof include quinoline, isoquinoline, quinazoline, quinoxaline, benzofuran, benzothiophene, benzoxazole, benzisoxazole, benzothiazole, benzoisothiazole, benzimidazole, benzotriazole, indole, isoindole, indazole, pyrrolopyrazine (e.g., 1H-pyrrolo[2,3-b]pyrazine), imidazopyridine (e.g., 2H-imidazo[1,2-a]pyridine, 1H-imidazo[4,5-b]pyridine, 1H-imidazo[4,5-c]pyridine), thienopyridine (e.g., thieno[2,3-b]pyridine), imidazopyrazine (e.g., 1H-imidazo[4,5-b]pyrazine), pyrazolopyridine (e.g., 1H-pyrazolo[4,3-c]pyridine), pyrazolothiophene (e.g., 2H-pyrazolo[3,4-b]thiophene), pyrazolotriazine (e.g., pyrazolo[5,1-c][1,2,4]triazine) and the like.

In the present specification, the "non-aromatic heterocycle" means a monocyclic non-aromatic heterocycle and a fused non-aromatic heterocycle.

Examples of the monocyclic non-aromatic heterocycle include a 4- to 7-membered (preferably 5- or 6-membered) monocyclic non-aromatic heterocycle containing, as a ring-constituting atom besides carbon atoms, 1 to 4 hetero atoms selected from an oxygen atom, a sulfur atom (optionally oxidized) and a nitrogen atom. Examples thereof include azetidine, pyrrolidine, piperidine, morpholine, thiomorpholine, piperazine, oxazolidine, thiazolidine, imidazolidine, oxazoline, thiazoline, imidazoline, dioxole, dioxolane, dihydrooxadiazole, pyran, dihydropyran, tetrahydropyran, thiopyran, dihydrothiopyran, tetrahydrothiopyran, 1-oxidotetrahydrothiopyran, 1,1-dioxidotetrahydrothiopyran, tetrahydrofuran, pyrazolidine, pyrazoline, tetrahydropyrimidine, dihydrotriazole, tetrahydrotriazole, azepane, dihydropyridine, tetrahydropyridine and the like.

Examples of the fused non-aromatic heterocycle include a 8- to 12-membered fused non-aromatic heterocycle, specifically, a fused ring wherein the above-mentioned 4- to 7-membered monocyclic non-aromatic heterocycle and a $C_{6-10}$ arene are condensed; a fused ring wherein the above-mentioned 4- to 7-membered monocyclic non-aromatic heterocycles are condensed; a fused ring wherein the above-mentioned 4- to 7-membered monocyclic non-aromatic heterocycle and the above-mentioned 5- to 7-membered monocyclic aromatic heterocycle are condensed; and a ring wherein the above-mentioned ring is partially saturated. Specific examples thereof include dihydroindole (e.g., 2,3-dihydro-1H-indole), dihydroisoindole (e.g., 1,3-dihydro-2H-isoindole), dihydrobenzofuran (e.g., 2,3-dihydro-1-benzofuran), tetrahydrobenzofuran (e.g., 4,5,6,7-tetrahydro-1-benzofuran), dihydrobenzodioxine (e.g., 2,3-dihydro-1,4-benzodioxine), dihydrobenzodioxepine (e.g., 3,4-dihydro-2H-1,5-benzodioxepine), chromene, dihydrochromene (e.g., 3,4-dihydro-2H-chromene), dihydroquinoline (e.g., 1,2-dihydroquinoline), tetrahydroquinoline (e.g., 1,2,3,4-tetrahydroquinoline), dihydroisoquinoline (e.g., 1,2-dihydroisoquinoline), tetrahydroisoquinoline (e.g., 1,2,3,4-tetrahydroisoquinoline), dihydrophthalazine (e.g., 1,4-dihydrophthalazine), azabicyclohexane (e.g., 2-azabicyclo[3.1.0]hexane) and the like.

In the present specification, the "nitrogen-containing heterocycle" means, for example, a 5- to 7-membered nitrogen-containing heterocycle containing, as a ring constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

In the present specification, the "heterocyclyl-carbonyl group" means a carbonyl group substituted by the aforementioned "heterocyclic group". Specific examples of the heterocyclyl-carbonyl group include pyrrolylcarbonyl, pyrazolylcarbonyl, pyridylcarbonyl, pyrrolidinylcarbonyl, thienylcarbonyl, furylcarbonyl, thiazolylcarbonyl, oxazolylcarbonyl, piperidinocarbonyl, piperazinylcarbonyl, morpholinocarbonyl, thiomorpholinocarbonyl, tetrahydrobenzo[c]azepinylcarbonyl, tetrahydroisoquinolinylcarbonyl and the like.

In the present specification, the "$C_{3-8}$ cycloalkyl-carbonyl group" means, for example, cyclopropylcarbonyl, cyclobutylcarbonyl, cyclopentylcarbonyl, cyclohexylcarbonyl, cycloheptylcarbonyl, cyclooctylcarbonyl or the like.

In the present specification, examples of the substituent that the $C_{1-6}$ alkyl group of the "$C_{1-6}$ alkyl group optionally having substituent(s)" optionally has include substituents selected from the following Substituent A Group. While the number of the substituents is not particularly limited as long as it is a substitutable number, preferably 1 to 5, more preferably 1 to 3. When plural substituents are present, the respective substituents may be the same or different.

Substituent A Group:
(1) a halogen atom;
(2) a cyano group;
(3) a nitro group;
(4) a hydroxy group;
(5) a carboxy group;
(6) a $C_{3-8}$ cycloalkyl group optionally having 1 to 3 substituents selected from
  (a) a halogen atom,
  (b) a hydroxy group,
  (c) a $C_{1-6}$ alkyl group optionally having 1 to 3 halogen atoms,
  (d) a $C_{1-6}$ alkoxy group optionally having 1 to 3 halogen atoms, and
  (e) an oxo group;
(7) a $C_{6-10}$ aryl group optionally having 1 to 3 substituents selected from
  (a) a halogen atom,
  (b) a hydroxy group,
  (c) a $C_{1-6}$ alkyl group optionally having 1 to 3 halogen atoms, and
  (d) a $C_{1-6}$ alkoxy group optionally having 1 to 3 halogen atoms;
(8) a 5- to 12-membered (preferably 5- or 6-membered) aromatic heterocyclic group optionally having 1 to 3 substituents selected from
  (a) a halogen atom,
  (b) a hydroxy group,
  (c) a $C_{1-6}$ alkyl group optionally having 1 to 3 halogen atoms, and
  (d) a $C_{1-6}$ alkoxy group optionally having 1 to 3 halogen atoms;
(9) a 4- to 12-membered (preferably 4- to 7-membered) non-aromatic heterocyclic group optionally having 1 to 3 substituents selected from
  (a) a halogen atom,
  (b) a hydroxy group,
  (c) a $C_{1-6}$ alkyl group optionally having 1 to 3 halogen atoms,
  (d) a $C_{1-6}$ alkoxy group optionally having 1 to 3 halogen atoms,
  (e) a $C_{1-6}$ alkyl-carbonyl group optionally having 1 to 3 hydroxy, and
  (f) an oxo group;
(10) an amino group optionally having 1 or 2 substituents selected from
  (a) a $C_{1-6}$ alkyl group optionally having 1 to 3 halogen atoms,
  (b) a $C_{1-6}$ alkyl-carbonyl group optionally having 1 to 3 substituents selected from
    (i) a halogen atom,
    (ii) a hydroxy group, and
    (iii) a $C_{6-10}$ aryl group,
  (c) a $C_{1-6}$ alkoxy-carbonyl group optionally having 1 to 3 substituents selected from
    (i) a halogen atom, and
    (ii) a $C_{6-10}$ aryl group,
  (d) a $C_{1-6}$ alkylsulfonyl group (e.g., methylsulfonyl) optionally having 1 to 3 substituents selected from
    (i) a halogen atom, and
    (ii) a $C_{6-10}$ aryl group,
  (e) a $C_{6-10}$ arylsulfonyl group (e.g., phenylsulfonyl),
  (f) a carbamoyl group optionally having 1 or 2 $C_{1-6}$ alkyl groups optionally having 1 to 3 halogen atoms,
  (g) a 5- to 12-membered (preferably 5- or 6-membered) aromatic heterocyclic group optionally having 1 to 3 substituents selected from
    (i) a $C_{1-6}$ alkyl group optionally having 1 to 3 halogen atoms,
    (ii) a hydroxy group,
    (iii) a $C_{1-6}$ alkoxy group optionally having 1 to 3 halogen atoms, and
    (iv) a halogen atom, and
  (h) a 4- to 12-membered (preferably 4- to 7-membered) non-aromatic heterocyclic group optionally having 1 to 3 substituents selected from
    (i) a $C_{1-6}$ alkyl group optionally having 1 to 3 halogen atoms,
    (ii) a hydroxy group,
    (iii) a $C_{1-6}$ alkoxy group optionally having 1 to 3 halogen atoms,
    (iv) a halogen atom, and
    (v) an oxo group;
(11) an imino group;
(12) a $C_{1-6}$ alkyl-carbonyl group optionally having 1 to 3 halogen atoms;
(13) a $C_{1-6}$ alkoxy-carbonyl group optionally having 1 to 3 substituents selected from
  (a) a halogen atom,
  (b) a $C_{1-6}$ alkoxy group,
  (c) a $C_{6-10}$ aryl group,
  (d) a 5- to 12-membered (preferably 5- or 6-membered) aromatic heterocyclic group optionally having 1 to 3 substituents selected from
    (i) a $C_{1-6}$ alkyl group optionally having 1 to 3 halogen atoms,
    (ii) a hydroxy group,
    (iii) a $C_{1-6}$ alkoxy group optionally having 1 to 3 halogen atoms, and
    (iv) a halogen atom, and
  (e) a 4- to 12-membered (preferably 4- to 7-membered) non-aromatic heterocyclic group optionally having 1 to 3 substituents selected from
    (i) a $C_{1-6}$ alkyl group optionally having 1 to 3 halogen atoms,
    (ii) a hydroxy group, (iii) a $C_{1-6}$ alkoxy group optionally having 1 to 3 halogen atoms,
(iv) a halogen atom, and
(v) an oxo group;
(14) a $C_{1-6}$ alkylsulfonyl group (e.g., methylsulfonyl, ethylsulfonyl, isopropylsulfonyl) optionally having 1 to 3 substituents selected from
  (a) a halogen atom, and
  (b) a $C_{1-6}$ alkoxy group;
(15) a $C_{6-10}$ arylsulfonyl group (e.g., phenylsulfonyl);
(16) a carbamoyl group optionally having 1 or 2 substituents selected from
  (a) a $C_{1-6}$ alkyl group optionally having 1 to 3 halogen atoms, and
  (b) a $C_{6-10}$ aryl group;
(17) a thiocarbamoyl group optionally having 1 or 2 $C_{1-6}$ alkyl groups optionally having 1 to 3 halogen atoms;
(18) a sulfamoyl group optionally having 1 or 2 $C_{1-6}$ alkyl groups optionally having 1 to 3 halogen atoms;
(19) a $C_{1-6}$ alkoxy group optionally having 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally having 1 to 3 $C_{6-10}$ aryl groups,
  (e) an amino group optionally having 1 or 2 substituents selected from a $C_{1-6}$ alkyl group and a $C_{1-6}$ alkoxy-carbonyl group,
  (f) a $C_{3-8}$ cycloalkyl group,
  (g) a 5- to 12-membered (preferably 5- or 6-membered) aromatic heterocyclic group optionally having 1 to 3 substituents selected from
    (i) a halogen atom,
    (ii) a hydroxy group,
    (iii) a $C_{1-6}$ alkyl group optionally having 1 to 3 halogen atoms, and
    (iv) a $C_{1-6}$ alkoxy group optionally having 1 to 3 halogen atoms, and
  (h) a 4- to 12-membered (preferably 4- to 7-membered) non-aromatic heterocyclic group optionally having 1 to 3 substituents selected from
    (i) a halogen atom,
    (ii) a hydroxy group,
    (iii) a $C_{1-6}$ alkyl group optionally having 1 to 3 halogen atoms,
    (iv) a $C_{1-6}$ alkoxy group optionally having 1 to 3 halogen atoms, and
    (v) an oxo group;
(20) a $C_{2-6}$ alkenyloxy group (e.g., ethenyloxy) optionally having 1 to 3 halogen atoms;
(21) a $C_{3-8}$ cycloalkyloxy group (e.g., cyclopropoxy, cyclopentyloxy) optionally having 1 to 3 substituents selected from
  (a) a halogen atom, and
  (b) a $C_{1-6}$ alkoxy group;
(22) a $C_{6-10}$ aryloxy group (e.g., phenyloxy, naphthyloxy);
(23) a $C_{7-13}$ aralkyloxy group (e.g., benzyloxy);
(24) a $C_{1-6}$ alkyl-carbonyloxy group (e.g., acetyloxy, tert-butylcarbonyloxy);
(25) a $C_{6-10}$ aryl-carbonyl group optionally having 1 to 3 substituents selected from
  (a) a halogen atom, and
  (b) a $C_{1-6}$ alkyl group optionally having 1 to 3 halogen atoms;
(26) a 5- to 12-membered (preferably 5- or 6-membered) aromatic heterocyclyl-carbonyl group (e.g., thienylcarbonyl, pyrazolylcarbonyl, pyrazinylcarbonyl, isoxazolylcarbonyl, pyridylcarbonyl, thiazolylcarbonyl) optionally having 1 to 3 substituents selected from a $C_{1-6}$ alkyl group optionally having 1 to 3 halogen atoms;
(27) a 4- to 12-membered (preferably 4- to 7-membered) non-aromatic heterocyclyl-carbonyl group (e.g., pyrrolidinylcarbonyl, morpholinylcarbonyl) optionally having 1 to 3 substituents selected from a $C_{1-6}$ alkyl group optionally having 1 to 3 halogen atoms;
(28) a $C_{3-8}$ cycloalkyl-carbonyl group;
(29) a $C_{7-13}$ aralkyloxy-carbonyl group (e.g., benzyloxycarbonyl);
(30) a mercapto group;
(31) a $C_{1-6}$ alkylthio group (e.g., methylthio, ethylthio) optionally having 1 to 3 substituents selected from
  (a) a halogen atom, and
  (b) a $C_{1-6}$ alkoxy-carbonyl group;
(32) a $C_{7-13}$ aralkylthio group (e.g., benzylthio);
(33) a $C_{6-10}$ arylthio group (e.g., phenylthio, naphthylthio);
(34) a $C_{1-3}$ alkyleneoxy group (e.g., methyleneoxy, ethyleneoxy); and
(35) a $C_{1-3}$ alkylenedioxy group (e.g., methylenedioxy, ethylenedioxy).

In the present specification, examples of the substituent that the $C_{2-6}$ alkenyl group of the "$C_{2-6}$ alkenyl group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{2-6}$ alkynyl group of the "$C_{2-6}$ alkynyl group optionally having substituent(s)" optionally has include substituents selected the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{1-6}$ alkoxy group of the "$C_{1-6}$ alkoxy group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{1-6}$ alkyl-carbonyl group of the "$C_{1-6}$ alkyl-carbonyl group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{6-10}$ aryl group of the "$C_{6-10}$ aryl group optionally having substituent(s)" optionally has include substituents selected from the following Substituent B Group. While the number of the substituents is not particularly limited as long as it is a substitutable number, preferably 1 to 5, more preferably 1 to 3. When plural substituents are present, the respective substituents may be the same or different.

Substituent B Group:
(1) the substituent selected from the aforementioned Substituent A Group;

(2) a $C_{1-6}$ alkyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group,
  (f) an amino group optionally having 1 or 2 $C_{1-6}$ alkyl groups, and
  (g) a $C_{6-10}$ aryl-carbonyl group;
(3) a $C_{2-6}$ alkenyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group, and
  (f) an amino group optionally having 1 or 2 $C_{1-6}$ alkyl groups; and
(4) a $C_{7-13}$ aralkyl group optionally having 1 to 3 substituents selected from
  (a) a halogen atom,
  (b) a hydroxy group,
  (c) a $C_{1-6}$ alkyl group optionally having 1 to 3 halogen atoms, and
  (d) a $C_{1-6}$ alkoxy group.

In the present specification, examples of the substituent that the $C_{3-8}$ cycloalkyl group of the "$C_{3-8}$ cycloalkyl group optionally having substituent(s)" optionally has include substituents selected from the following Substituent C Group. While the number of the substituents is not particularly limited as long as it is a substitutable number, preferably 1 to 5, more preferably 1 to 3. When plural substituents are present, the respective substituents may be the same or different.

Substituent C Group:
(1) the substituent selected from the aforementioned Substituent A Group;
(2) a $C_{1-6}$ alkyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group,
  (f) an amino group optionally having 1 or 2 $C_{1-6}$ alkyl groups, and
  (g) a $C_{6-10}$ aryl-carbonyl group;
(3) a $C_{2-6}$ alkenyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group, and
  (f) an amino group optionally having 1 or 2 $C_{1-6}$ alkyl groups;
(4) a $C_{7-13}$ aralkyl group optionally having 1 to 3 substituents selected from
  (a) a halogen atom,
  (b) a hydroxy group,
  (c) a $C_{1-6}$ alkyl group optionally having 1 to 3 halogen atoms,
  (d) a $C_{1-6}$ alkoxy group; and
(5) an oxo group.

In the present specification, examples of the substituent that the $C_{6-10}$ aryl-carbonyl group of the "$C_{6-10}$ aryl-carbonyl group optionally having substituent(s)" optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclic group of the "heterocyclic group optionally having substituent(s)" is an "aromatic heterocyclic group", examples of the substituent that the aromatic heterocyclic group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclic group of the "heterocyclic group optionally having substituent(s)" is a "non-aromatic heterocyclic group", examples of the substituent that the non-aromatic heterocyclic group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, when the heterocyclyl-carbonyl group of the "heterocyclyl-carbonyl group optionally having substituent(s)" is an "aromatic heterocyclyl-carbonyl group", examples of the substituent that the aromatic heterocyclyl-carbonyl group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclyl-carbonyl group of the "heterocyclyl-carbonyl group optionally having substituent(s)" is a "non-aromatic heterocyclyl-carbonyl group", examples of the substituent that the non-aromatic heterocyclyl-carbonyl group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "amino group optionally having substituent(s)" means, for example, an "amino group" optionally having 1 or 2 substituents selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s); and the like.

When the "amino group optionally having substituent(s)" is an amino group having 2 substituents, these substituents optionally form, together with the adjacent nitrogen atom, a nitrogen-containing heterocycle. Specific examples of the nitrogen-containing heterocycle include a 5- to 7-membered nitrogen-containing heterocycle. The nitrogen-containing heterocycle optionally further has substituent(s). Examples of the substituent include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "carbamoyl group optionally having substituent(s)" means, for example, a "carbamoyl group" optionally having 1 or 2 substituents selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s); and the like.

When the "carbamoyl group optionally having substituent(s)" is a carbamoyl group having 2 substituents, these substituents optionally form, together with the adjacent nitrogen atom, a nitrogen-containing heterocycle. Specific examples of the nitrogen-containing heterocycle include a 5- to 7-membered nitrogen-containing heterocycle. The nitrogen-containing heterocycle optionally further has substituent(s). Examples of the substituent include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "optionally substituted hydroxy group" means, for example, a hydroxy group optionally substituted by a substituent selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkyl-carbonyl group optionally having substituent(s);
(5) a $C_{3-8}$ cycloalkyl group optionally having substituent(s);
(6) a $C_{6-10}$ aryl group optionally having substituent(s);
(7) a $C_{6-10}$ aryl-carbonyl group optionally having substituent(s);
(8) a heterocyclic group optionally having substituent(s);
(9) a heterocyclyl-carbonyl group optionally having substituent(s); and the like.

In the present specification, the "optionally substituted mercapto group" means, for example, a mercapto group optionally substituted by a substituent selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s);
and the like.

In the present specification, the "cyclic group" of the "cyclic group optionally having substituent(s)" means, for example, a $C_{3-8}$ cycloalkyl group, a group derived from a fused ring wherein a $C_{3-8}$ cycloalkane and a benzene ring are condensed (e.g., indanyl, 1,2,3,4-tetrahydronaphthyl), a $C_{6-10}$ aryl group, an aromatic heterocyclic group, a non-aromatic heterocyclic group or the like.

When the "cyclic group optionally having substituent(s)" is a $C_{3-8}$ cycloalkyl group optionally having substituent(s), examples of the substituent that the $C_{3-8}$ cycloalkyl group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a group derived from a fused ring wherein a $C_{3-8}$ cycloalkane and a benzene ring are condensed, which optionally has substituent(s), examples of the substituent that the fused ring group optionally has include substituents selected from the aforementioned Substituent C Group. The position of the substituent is not particularly limited as long as it is a substitutable position, and may be on the benzene ring moiety or $C_{3-8}$ cycloalkane moiety. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a $C_{6-10}$ aryl group optionally having substituent(s), examples of the substituent that the $C_{6-10}$ aryl group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is an aromatic heterocyclic group optionally having substituent(s), Examples of the substituent that the aromatic heterocyclic group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a non-aromatic heterocyclic group optionally having substituent(s), examples of the substituent that the non-aromatic heterocyclic group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the formula (DI), $X^D$ is $NR^{D1}$, a sulfur atom or an oxygen atom. $R^{D1}$ is a hydrogen atom or a $C_{1-6}$ alkyl group.

$X^D$ is preferably $NR^{D1}$ or a sulfur atom, more preferably $NR^{D1}$. $R^{D1}$ is preferably a $C_{1-6}$ alkyl group (e.g., methyl), more preferably methyl.

In the formula (DI), $Y^D$ is $CR^{D7}$ or a nitrogen atom. $R^{D7}$ is a hydrogen atom, a halogen atom or a $C_{1-6}$ alkyl group.

$Y^D$ is preferably $CR^{D7}$. $R^{D7}$ is preferably a hydrogen atom.

In the formula (DI), $R^{D2}$ is a carbamoyl group optionally having substituent(s).

$R^{D2}$ is preferably a carbamoyl group optionally having 1 or 2 substituents selected from
(1) a $C_{1-6}$ alkyl group optionally having substituent(s),
(2) a $C_{2-6}$ alkynyl group optionally having substituent(s),
(3) a $C_{3-8}$ cycloalkyl group optionally having substituent(s), and
(4) a heterocyclic group optionally having substituent(s).

In one embodiment, $R^{D2}$ is more preferably a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl) optionally having 1 to 3 substituents selected from
    (a) a $C_{1-6}$ alkyl group optionally having 1 to 3 hydroxy groups, and
    (b) a $C_{1-6}$ alkyl-carbonyl group (e.g., acetyl) optionally having 1 to 3 hydroxy groups;
(2) a $C_{3-8}$ cycloalkyl group (e.g., cyclohexyl) optionally having 1 to 3 hydroxy groups; and
(3) a $C_{1-6}$ alkyl group (e.g., ethyl, propyl) having one substituent selected from
    (a) a $C_{1-6}$ alkylsulfonyl group (e.g., ethylsulfonyl) optionally having 1 to 3 $C_{1-6}$ alkoxy groups (e.g., methoxy), and
    (b) an amino group having one $C_{1-6}$ alkyl-carbonyl group (e.g., acetyl) optionally having 1 to 3 hydroxy groups.

In another embodiment, $R^{D2}$ is more preferably a carbamoyl group having 1 or 2 substituents selected from
(1) a 4- to 12-membered (preferably 4- to 7-membered) non-aromatic heterocyclic group (e.g., morpholinyl, piperidyl, azepanyl) optionally having 1 to 3 substituents selected from
    (a) a $C_{1-6}$ alkyl group optionally having 1 to 3 hydroxy groups,
    (b) a $C_{1-6}$ alkyl-carbonyl group (e.g., acetyl) optionally having 1 to 3 hydroxy groups, and
    (c) an oxo group;
(2) a $C_{3-8}$ cycloalkyl group (e.g., cyclopropyl, cyclopentyl, cyclohexyl) optionally having 1 to 3 substituents selected from
    (a) a hydroxy group,
    (b) a $C_{1-6}$ alkyl group (e.g., methyl) optionally having 1 to 3 hydroxy groups,
    (c) a carbamoyl group,
    (d) a $C_{2-6}$ alkynyl group (e.g., ethynyl), and
    (e) a 5- to 12-membered (preferably 5- or 6-membered) aromatic heterocyclic group (e.g., thienyl);
(3) a $C_{1-6}$ alkyl group (e.g., methyl, ethyl, propyl, isopropyl, butyl, isobutyl, sec-butyl, tert-butyl) having one substituent selected from
    (a) a $C_{1-6}$ alkylsulfonyl group (e.g., ethylsulfonyl) optionally having 1 to 3 $C_{1-6}$ alkoxy groups (e.g., methoxy),
    (b) an amino group having one $C_{1-6}$ alkyl-carbonyl group (e.g., acetyl) optionally having 1 to 3 hydroxy groups,
    (c) an amino group having 1 or 2 $C_{1-6}$ alkyl groups (e.g., methyl, ethyl) optionally having 1 to 3 hydroxy groups,
    (d) a $C_{6-10}$ aryl group (e.g., phenyl) optionally having 1 to 3 $C_{1-6}$ alkylsulfonyl groups (e.g., methylsulfonyl),
    (e) a 4- to 12-membered (preferably 4- to 7-membered) non-aromatic heterocyclic group (e.g., pyrrolidinyl, tetrahydrofuryl) optionally having 1 to 3 oxo groups,
    (f) a 5- to 12-membered (preferably 5- or 6-membered) aromatic heterocyclic group (e.g., furyl),
    (g) a hydroxy group, and
    (h) a $C_{1-6}$ alkoxy group (e.g., methoxy);
(4) a 5- to 12-membered (preferably 5- or 6-membered) aromatic heterocyclic group (e.g., pyridyl); and
(5) a $C_{2-6}$ alkynyl group (e.g., 2-propynyl).

In the formula (DI), $R^{D3}$ is a halogen atom, a $C_{1-6}$ alkyl group optionally having substituent(s), a $C_{2-6}$ alkenyl group optionally having substituent(s), an amino group optionally having substituent(s), a mercapto group optionally having a substituent, a cyclic group optionally having substituent(s) or a cyano group.

$R^{D3}$ is preferably a $C_{1-6}$ alkyl group (e.g., ethyl), a $C_{2-6}$ alkenyl group (e.g., vinyl), an amino group optionally having 1 or 2 $C_{1-6}$ alkyl groups (e.g., ethyl) or a cyano group, more preferably a $C_{1-6}$ alkyl group (e.g., ethyl), a $C_{2-6}$ alkenyl group (e.g., vinyl) or a cyano group, more preferably a $C_{1-6}$ alkyl group (e.g., ethyl) or a $C_{2-6}$ alkenyl group (e.g., vinyl), still more preferably a $C_{1-6}$ alkyl group (e.g., ethyl).

In the formula (DI), $R^{D5}$ is a $C_{1-6}$ alkyl group optionally having substituent(s) or a cyclic group optionally having substituent(s).

$R^{D5}$ is preferably
(1) a $C_{1-6}$ alkyl group optionally having substituent(s),
(2) a $C_{6-10}$ aryl group optionally having substituent(s), or
(3) a heterocyclic group optionally having substituent(s).

In one embodiment, $R^{D5}$ is more preferably
(1) a $C_{1-6}$ alkyl group (e.g., methyl, ethyl, pentyl) optionally having 1 to 3 substituents selected from
    (a) a $C_{6-10}$ aryl-carbonyl group (e.g., benzoyl),
    (b) a $C_{6-10}$ aryl group (e.g., phenyl) optionally having 1 to 3 substituents selected from
        (i) a halogen atom (e.g., a fluorine atom, a chlorine atom), and
        (ii) a $C_{1-6}$ alkoxy group (e.g., methoxy), and
    (c) a $C_{1-6}$ alkoxy group (e.g., methoxy) optionally having 1 to 3 $C_{6-10}$ aryl groups (e.g., phenyl);
(2) a $C_{6-10}$ aryl group (e.g., phenyl, naphthyl) optionally having 1 to 3 substituents selected from
    (a) a halogen atom (e.g., a fluorine atom, a chlorine atom),
    (b) a $C_{1-6}$ alkyl group (e.g., methyl, ethyl) optionally having 1 to 3 halogen atoms (e.g., a fluorine atom), and
    (c) a $C_{1-6}$ alkoxy group (e.g., methoxy, isopropoxy); or
(3) a 5- or 6-membered monocyclic aromatic heterocyclic group (e.g., pyridyl) optionally having 1 to 3 substituents selected from
    (a) a halogen atom (e.g., a fluorine atom),
    (b) a $C_{1-6}$ alkyl group (e.g., methyl), and
    (c) a $C_{1-6}$ alkoxy group (e.g., methoxy).

In another embodiment, $R^{D5}$ is more preferably
(1) a $C_{1-6}$ alkyl group (e.g., methyl, ethyl, pentyl) optionally having 1 to 3 substituents selected from
    (a) a $C_{6-10}$ aryl-carbonyl group (e.g., benzoyl),
    (b) a $C_{6-10}$ aryl group (e.g., phenyl) optionally having 1 to 3 substituents selected from
        (i) a halogen atom (e.g., a fluorine atom, a chlorine atom), and
        (ii) a $C_{1-6}$ alkoxy group (e.g., methoxy), and
    (c) a $C_{1-6}$ alkoxy group (e.g., methoxy) optionally having 1 to 3 $C_{6-10}$ aryl groups (e.g., phenyl); or
(2) a $C_{6-10}$ aryl group (e.g., phenyl, naphthyl) optionally having 1 to 3 substituents selected from
    (a) a halogen atom (e.g., a fluorine atom, a chlorine atom),
    (b) a $C_{1-6}$ alkyl group (e.g., methyl, ethyl) optionally having 1 to 3 halogen atoms (e.g., a fluorine atom), and
    (c) a $C_{1-6}$ alkoxy group (e.g., methoxy, isopropoxy):
more preferably a $C_{1-6}$ alkyl group (e.g., methyl, ethyl, pentyl) having one benzoyl.

In the formula (DI), $R^{D6}$ is a hydrogen atom, a halogen atom or a $C_{1-6}$ alkyl group.

$R^{D6}$ is preferably a $C_{1-6}$ alkyl group (e.g., methyl, ethyl).

In one preferable embodiment, $X^D$ is $NR^{D1}$ wherein $R^{D1}$ is ethyl, and $Y^D$ is $CR^{D7}$ wherein $R^{D7}$ is a hydrogen atom.

Preferable specific examples of compound (DI) include the following compounds.

Compound (DI-1)

In the formula (DI), a compound wherein
$X^D$ is $NR^{D1}$, a sulfur atom or an oxygen atom (preferably $X^D$ is $NR^{D1}$);
$R^{D1}$ is a hydrogen atom or a $C_{1-6}$ alkyl group;
$Y^D$ is $CR^{D7}$ or a nitrogen atom (preferably $Y^D$ is $CR^{D7}$);
$R^{D7}$ is a hydrogen atom, a halogen atom or a $C_{1-6}$ alkyl group; preferably $X^D$ is $NR^{D1}$, $R^{D1}$ is a $C_{1-6}$ alkyl group (e.g., methyl),
$Y^D$ is $CR^{D7}$, and $R^{D7}$ is a hydrogen atom;
$R^{D2}$ is a carbamoyl group optionally having 1 or 2 substituents selected from
(1) a $C_{1-6}$ alkyl group optionally having substituent(s),
(2) a $C_{2-6}$ alkynyl group optionally having substituent(s),
(3) a $C_{3-8}$ cycloalkyl group optionally having substituent(s), and
(4) a heterocyclic group optionally having substituent(s);
$R^{D3}$ is a $C_{1-6}$ alkyl group, a $C_{2-6}$ alkenyl group or a cyano group (preferably $R^{D3}$ is a $C_{1-6}$ alkyl group or a $C_{2-6}$ alkenyl group);
$R^{D5}$ is
(1) a $C_{1-6}$ alkyl group optionally having substituent(s),
(2) a $C_{6-10}$ aryl group optionally having substituent(s), or
(3) a heterocyclic group optionally having substituent(s); and
$R^{D6}$ is a $C_{1-6}$ alkyl group,
or a salt thereof.

Compound (DI-2)

In the formula (DI), a compound wherein
$X^D$ is $NR^{D1}$, a sulfur atom or an oxygen atom (preferably $NR^{D1}$ or a sulfur atom);
$R^{D1}$ is a hydrogen atom or a $C_{1-6}$ alkyl group (e.g., methyl) (preferably a $C_{1-6}$ alkyl group (e.g., methyl));
$Y^D$ is $CR^{D7}$ or a nitrogen atom;
$R^{D7}$ is a hydrogen atom;
$R^{D2}$ is a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl) optionally having 1 to 3 substituents selected from
  (a) a $C_{1-6}$ alkyl group optionally having 1 to 3 hydroxy groups, and
  (b) a $C_{1-6}$ alkyl-carbonyl group (e.g., acetyl) optionally having 1 to 3 hydroxy groups;
(2) a $C_{3-8}$ cycloalkyl group (e.g., cyclohexyl) optionally having 1 to 3 hydroxy groups; and
(3) a $C_{1-6}$ alkyl group (e.g., ethyl, propyl) having one substituent selected from
  (a) a $C_{1-6}$ alkylsulfonyl group (e.g., ethylsulfonyl) optionally having 1 to 3 $C_{1-6}$ alkoxy groups (e.g., methoxy), and
  (b) an amino group having one $C_{1-6}$ alkyl-carbonyl group (e.g., acetyl) optionally having 1 to 3 hydroxy groups;
$R^{D3}$ is a $C_{1-6}$ alkyl group (e.g., ethyl) or a $C_{2-6}$ alkenyl group (e.g., vinyl);

$R^{D5}$ is
(1) a $C_{1-6}$ alkyl group (e.g., methyl, ethyl, pentyl) optionally having 1 to 3 substituents selected from
  (a) a $C_{6-10}$ aryl-carbonyl group (e.g., benzoyl),
  (b) a $C_{6-10}$ aryl group (e.g., phenyl) optionally having 1 to 3 substituents selected from
    (i) a halogen atom (e.g., a fluorine atom, a chlorine atom), and
    (ii) a $C_{1-6}$ alkoxy group (e.g., methoxy), and
  (c) a $C_{1-6}$ alkoxy group (e.g., methoxy) optionally having 1 to 3 $C_{6-10}$ aryl groups (e.g., phenyl);
(2) a $C_{6-10}$ aryl group (e.g., phenyl, naphthyl) optionally having 1 to 3 substituents selected from
  (a) a halogen atom (e.g., a fluorine atom, a chlorine atom),
  (b) a $C_{1-6}$ alkyl group (e.g., methyl, ethyl) optionally having 1 to 3 halogen atoms (e.g., a fluorine atom), and
  (c) a $C_{1-6}$ alkoxy group (e.g., methoxy, isopropoxy); or
(3) a 5- or 6-membered monocyclic aromatic heterocyclic group (e.g., pyridyl) optionally having 1 to 3 substituents selected from
  (a) a halogen atom (e.g., a fluorine atom),
  (b) a $C_{1-6}$ alkyl group (e.g., methyl), and
  (c) a $C_{1-6}$ alkoxy group (e.g., methoxy); and
$R^{D6}$ is a $C_{1-6}$ alkyl group (e.g., methyl, ethyl),
or a salt thereof.

Compound (DI-3)

In the formula (DI), a compound wherein
$X^D$ is $NR^{D1}$ wherein $R^{D1}$ is methyl;
$Y^D$ is $CR^{D7}$ wherein $R^{D7}$ is a hydrogen atom, or a nitrogen atom (preferably $CR^{D7}$ wherein $R^{D7}$ is a hydrogen atom);
$R^{D2}$ is a carbamoyl group having 1 or 2 substituents selected from
(1) a 4- to 12-membered (preferably 4- to 7-membered) non-aromatic heterocyclic group (e.g., morpholinyl, piperidyl, azepanyl) optionally having 1 to 3 substituents selected from
  (a) a $C_{1-6}$ alkyl group optionally having 1 to 3 hydroxy groups,
  (b) a $C_{1-6}$ alkyl-carbonyl group (e.g., acetyl) optionally having 1 to 3 hydroxy groups, and
  (c) an oxo group;
(2) a $C_{3-8}$ cycloalkyl group (e.g., cyclopropyl, cyclopentyl, cyclohexyl) optionally having 1 to 3 substituents selected from
  (a) a hydroxy group,
  (b) a $C_{1-6}$ alkyl group (e.g., methyl) optionally having 1 to 3 hydroxy groups,
  (c) a carbamoyl group,
  (d) a $C_{2-6}$ alkynyl group (e.g., ethynyl), and
  (e) a 5- to 12-membered (preferably 5- or 6-membered) aromatic heterocyclic group (e.g., thienyl);
(3) a $C_{1-6}$ alkyl group (e.g., methyl, ethyl, propyl, isopropyl, butyl, isobutyl, sec-butyl, tert-butyl) having one substituent selected from
  (a) a $C_{1-6}$ alkylsulfonyl group (e.g., ethylsulfonyl) optionally having 1 to 3 $C_{1-6}$ alkoxy groups (e.g., methoxy),
  (b) an amino group having one $C_{1-6}$ alkyl-carbonyl group (e.g., acetyl) optionally having 1 to 3 hydroxy groups,
  (c) an amino group having 1 or 2 $C_{1-6}$ alkyl groups (e.g., methyl, ethyl) optionally having 1 to 3 hydroxy groups,
  (d) a $C_{6-10}$ aryl group (e.g., phenyl) optionally having 1 to 3 $C_{1-6}$ alkylsulfonyl groups (e.g., methylsulfonyl),
  (e) a 4- to 12-membered (preferably 4- to 7-membered) non-aromatic heterocyclic group (e.g., pyrrolidinyl, tetrahydrofuryl) optionally having 1 to 3 oxo groups, (f) a 5- to 12-membered (preferably 5- or 6-membered) aromatic heterocyclic group (e.g., furyl),
(g) a hydroxy group, and
(h) a $C_{1-6}$ alkoxy group (e.g., methoxy);
(4) a 5- to 12-membered (preferably 5- or 6-membered) aromatic heterocyclic group (e.g., pyridyl); and
(5) a $C_{2-6}$ alkynyl group (e.g., 2-propynyl);
$R^{D3}$ is a $C_{1-6}$ alkyl group (e.g., ethyl) or a $C_{2-6}$ alkenyl group (e.g., vinyl) (preferably a $C_{1-6}$ alkyl group (e.g., ethyl));
$R^{D5}$ is
(1) a $C_{1-6}$ alkyl group (e.g., methyl, ethyl, pentyl) optionally having 1 to 3 substituents selected from
   (a) a $C_{6-10}$ aryl-carbonyl group (e.g., benzoyl),
   (b) a $C_{6-10}$ aryl group (e.g., phenyl) optionally having 1 to 3 substituents selected from
     (i) a halogen atom (e.g., a fluorine atom, a chlorine atom), and
     (ii) a $C_{1-6}$ alkoxy group (e.g., methoxy), and
   (c) a $C_{1-6}$ alkoxy group (e.g., methoxy) optionally having 1 to 3 $C_{6-10}$ aryl groups (e.g., phenyl);
(2) a $C_{6-10}$ aryl group (e.g., phenyl, naphthyl) optionally having 1 to 3 substituents selected from
   (a) a halogen atom (e.g., a fluorine atom, a chlorine atom),
   (b) a $C_{1-6}$ alkyl group (e.g., methyl, ethyl) optionally having 1 to 3 halogen atoms (e.g., a fluorine atom), and
   (c) a $C_{1-6}$ alkoxy group (e.g., methoxy, isopropoxy); or
(3) a 5- or 6-membered monocyclic aromatic heterocyclic group (e.g., pyridyl) optionally having 1 to 3 substituents selected from
   (a) a halogen atom (e.g., a fluorine atom),
   (b) a $C_{1-6}$ alkyl group (e.g., methyl), and
   (c) a $C_{1-6}$ alkoxy group (e.g., methoxy)
(preferably a $C_{1-6}$ alkyl group (e.g., methyl, ethyl, pentyl) having one benzoyl); and
$R^{D6}$ is a $C_{1-6}$ alkyl group (e.g., methyl, ethyl),
or a salt thereof.
Compound (DI-4)
3,6-diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide;
3-ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide; or
6-ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide;
or a salt thereof.

Examples of the salt in compound (DI) include metal salts, ammonium salts, salts with organic base, salts with inorganic acid, salts with organic acid, salts with basic or acidic amino acid and the like. Preferable examples of the metal salt include alkali metal salts such as sodium salt, potassium salt and the like; alkaline earth metal salts such as calcium salt, magnesium salt, barium salt and the like; an aluminum salt and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like, and preferable examples of the salt with acidic amino acid include salts with aspartic acid, glutamic acid and the like.

Of these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acids such as hydrochloric acid, hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is described in the following.

In each of the following production methods, when alkylation reaction, amidation reaction (condensation reaction), esterification reaction, reduction reaction, reductive amination reaction, amination reaction, halogenation reaction, oxidation reaction and the like are performed, these reactions are performed according to methods known per se. Examples of such methods include the methods described in Organic Functional Group Preparations, 2nd edition, Academic Press, Inc. (1989), Comprehensive Organic Transformations, VCH Publishers Inc. (1989) and the like, and the like.

In the following reaction, the starting compound or the intermediate may be in the form of a salt. Examples of the salt include those similar to the aforementioned salt of compound (DI).

The obtained compound in each step may be used in the form of the reaction mixture or as a crude product for the next step, or may be isolated from the reaction mixture according to a conventional method (e.g., separation means such as recrystallization, distillation, chromatography etc.).

In each of the above-mentioned reactions, when the starting compound has an amino group, a carboxyl group or a hydroxy group as a substituent, a protecting group generally used in peptide chemistry and the like may be introduced into these groups. By removing the protecting group as necessary after the reaction, the objective compound can be obtained. The protection and deprotection are performed according to a method known per se, for example, the method described in Protective Groups in Organic Synthesis, 3rd edition, John Wiley and Sons, Inc. (1999).

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

The solvents indicated in generic terms, which are used in the following reactions are explained in the following.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane and the like.

Examples of the "esters" include ethyl acetate, methyl acetate, tert-butyl acetate and the like.

Examples of the "hydrocarbons" include benzene, toluene, xylene, cyclohexane, hexane, pentane and the like.

Examples of the "amides" include N,N-dimethylformamide, N,N-dimethylacetamide, hexamethylphosphoric triamide and the like.

Examples of the "halogenated hydrocarbons" include dichloromethane, chloroform, carbon tetrachloride, 1,2-dichloroethane, tetrachloroethylene, chlorobenzene and the like.

Examples of the "nitriles" include acetonitrile, propionitrile and the like.

Examples of the "ketones" include acetone, 2-butanone and the like.

Examples of the "organic acids" include formic acid, acetic acid, propionic acid, trifluoroacetic acid, methanesulfonic acid and the like.

Examples of the "aromatic amines" include pyridine, 2,6-lutidine, quinoline and the like.

Examples of the "sulfoxides" include dimethyl sulfoxide and the like.

Compound (DI) can be produced, for example, according to the following [Method DA] or a method analogous thereto.

[Method DA]

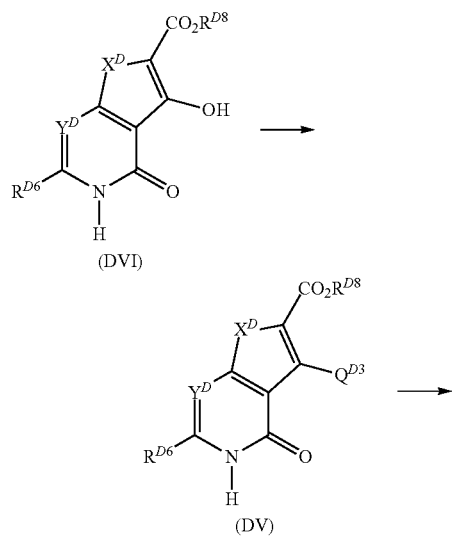

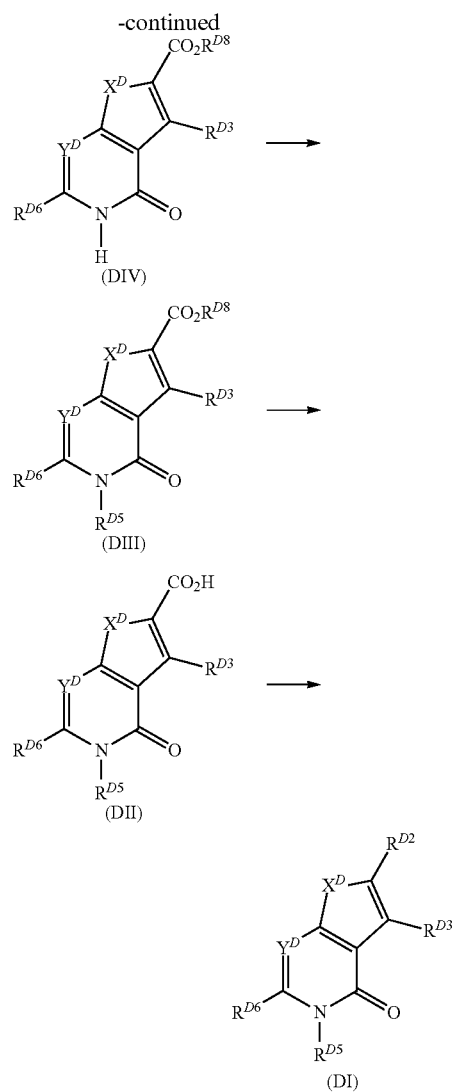

wherein $Q^{D3}$ is a leaving group, $R^{D8}$ is a $C_{1-6}$ alkyl group or a $C_{7-13}$ aralkyl group, and other symbols are as defined above.

Examples of the leaving group for $Q^{D3}$ include a $C_{1-6}$ alkylsulfonyloxy group optionally having 1 to 3 halogen atoms (e.g., methylsulfonyloxy, ethylsulfonyloxy, trifluoromethylsulfonyloxy), a $C_{6-10}$ arylsulfonyloxy group optionally having 1 to 3 $C_{1-6}$ alkyl groups (e.g., benzenesulfonyloxy, 4-toluenesulfonyloxy), $C_{1-6}$ alkylsulfonyl group (e.g., methanesulfonyl), and the like.

$Q^{D3}$ is preferably a $C_{1-6}$ alkylsulfonyloxy group.

$R^{D8}$ is preferably ethyl, benzyl.

The reaction from compound (DVI) to compound (DV) can be carried out by reacting compound (DVI) with a sulfonylating reagent under basic condition, in a solvent that does not adversely influence the reaction.

Examples of the sulfonylating reagent include trifluoromethanesulfonic anhydride, methanesulfonyl halides optionally having 1 to 3 halogen atoms, benzenesulfonyl halides optionally having 1 to 3 $C_{1-6}$ alkyl groups, and the like.

The amount of the sulfonylating reagent to be used is generally 1 to 2 mol, preferably 1 to 1.5 mol, per 1 mol of compound (DVI).

Where necessary, a base may be used for the reaction under basic condition. Examples of the base include triethylamine, diisopropylethylamine, pyridine, 4-dimethylaminopyridine and the like.

The amount of the base to be used is generally 2 to 5 mol, preferably 2 to 3 mol, per 1 mol of compound (DVI).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally −10 to 100° C., preferably 0 to 60° C.

The reaction time is generally 0.5 to 100 hr, preferably 1 to 48 hr.

When $R^{D3}$ is a $C_{1-6}$ alkenyl group optionally having substituent(s) or an amino group optionally having substituent(s), the reaction from compound (DV) to compound (DIV) can be carried out by reacting compound (DV) with a tin compound or amine corresponding to $R^{D3}$, in a solvent that does not adversely influence the reaction.

Specifically, compound (DV) is reacted with a tin compound or amine corresponding to $R^{D3}$, a copper compound (e.g., copper powder, copper(I) iodide, copper(I) chloride, copper oxide, copper(II) acetate and the like) and a base (e.g., potassium carbonate, potassium phosphate, triethylamine, pyridine).

Alternatively, compound (DV) is reacted with a tin compound corresponding to $R^{D3}$, a palladium compound (e.g., tris(dibenzylideneacetone)dipalladium(0), palladium(II) acetate), a ligand (e.g., 9,9-dimethyl-4,5-bis(diphenylphosphino)xanthene) and a base (e.g., cesium carbonate, sodium t-butoxide).

The amount of the tin compound or amine corresponding to $R^{D3}$ to be used is generally 1 to 5 mol, preferably 1 to 3 mol, per 1 mol of compound (DV).

The amount of the copper compound to be used is generally 0.01 to 1 mol, preferably 0.1 to 0.5 mol, per 1 mol of compound (DV).

The amount of the palladium compound to be used is generally 0.01 to 1 mol, preferably 0.1 to 0.5 mol, per 1 mol of compound (DV).

The amount of the ligand to be used is generally 0.01 to 1 mol, preferably 0.1 to 0.5 mol, per 1 mol of compound (DV).

The amount of the base to be used is generally 1 to 5 mol, preferably 1 to 3 mol, per 1 mol of compound (DV).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally 0 to 150° C., preferably 20 to 120° C.

The reaction time is generally 0.5 to 100 hr, preferably 1 to 48 hr.

When $R^{D3}$ is a mercapto group optionally having a substituent, a halogen atom or a cyano group, the reaction from compound (DV) to compound (DIV) can be carried out by reacting compound (DV) with a thiol, metal halide or cyanide corresponding to $R^{D3}$ in a solvent that does not adversely influence the reaction, in the presence of a catalyst and a base, as necessary.

Examples of the thiol corresponding to $R^{D3}$ include methanethiol and ethanethiol.

Examples of the metal halide corresponding to $R^{D3}$ include sodium bromide, lithium chloride and the like.

Examples of the cyanide corresponding to $R^{D3}$ include zinc(II) cyanide, sodium cyanide, potassium cyanide, copper cyanide, trimethylsilyl cyanide and the like.

The amount of the thiol, metal halide or cyanide corresponding to $R^{D3}$ to be used is generally 1 to 5 mol, preferably 1 to 3 mol, per 1 mol of compound (DV).

Examples of the catalyst used as necessary include tetrakis(triphenylphosphine)palladium(0) and the like.

The amount of the catalyst to be used is generally 0.001 to 1 mol, preferably 0.05 to 0.5 mol, per 1 mol of compound (DV).

Examples of the base used as necessary include 1,8-azabicyclo[5.4.0]undec-7-ene (DBU), sodium hydride, sodium methoxide, sodium ethoxide, sodium carbonate, sodium hydrogen carbonate, sodium hydroxide, triethylamine, diisopropylethylamine, pyridine, 4-dimethylaminopyridine and the like.

The amount of the base to be used is generally 1 to 5 mol, preferably 1 to 3 mol, per 1 mol of compound (DV).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally 0 to 150° C., preferably 20 to 120° C.

The reaction time is generally 0.5 to 100 hr, preferably 1 to 48 hr.

The thiol, metal halide or cyanide corresponding to $R^{D3}$ may be commercially available product, or can be produced from the corresponding starting material compound according to a method known per se.

When $R^{D3}$ is a $C_{1-6}$ alkyl group optionally having substituent(s) or a cyclic group optionally having substituent(s), the reaction from compound (DV) to compound (DIV) can be carried out by reacting compound (DV) with a tin compound, boronic acid or borate corresponding to $R^{D3}$ in a solvent that does not adversely influence the reaction, in the presence of a base, as necessary.

Specifically, compound (DV) is reacted with a tin compound, boronic acid or borate corresponding to $R^{D3}$, a palladium compound (e.g., tris(dibenzylideneacetone)dipalladium(0), palladium(II) acetate), ligand (e.g., 9,9-dimethyl-4,5-bis(diphenylphosphino)xanthene) and a base (e.g., cesium carbonate, sodium t-butoxide).

The amount of the tin compound, boronic acid or borate corresponding to $R^{D3}$ to be used is generally 1 to 5 mol, preferably 1 to 3 mol, per 1 mol of compound (DV).

The amount of the palladium compound to be used is generally 0.01 to 1 mol, preferably 0.1 to 0.5 mol, per 1 mol of compound (DV).

The amount of the ligand to be used is generally 0.01 to 1 mol, preferably 0.1 to 0.5 mol, per 1 mol of compound (DV).

The amount of the base to be used is generally 1 to 5 mol, preferably 1 to 3 mol, per 1 mol of compound (DV).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally 0 to 150° C., preferably 20 to 120° C.

The reaction time is generally 0.5 to 100 hr, preferably 1 to 48 hr.

The tin compound, boronic acid or borate corresponding to $R^{D3}$ may be commercially available product, or can be produced from the corresponding starting material compound according to a method known per se.

When $R^{D3}$ is a $C_{1-6}$ alkyl group optionally having substituent(s), the reaction from compound (DV) to compound (DIV) can be carried out by reducing compound (DIV) wherein $R^{D3}$ is a $C_{1-6}$ alkenyl group optionally having substituent(s) in a solvent that does not adversely influence the reaction.

A catalytic hydrogenation can be employed for the reduction. Examples of the catalyst include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (DV) wherein $R^{D3}$ is a $C_{1-6}$ alkenyl group optionally having substituent(s).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. Two or more kinds of the above-mentioned solvents may mixed in an appropriate ratio and used.

The reaction temperature is generally 0 to 100° C., preferably 20 to 60° C.

The reaction time is generally 0.5 to 100 hr, preferably 1 to 48 hr.

The reaction from compound (DIV) to compound (DIII) can be carried out using compound (DIV) and a halide corresponding to $R^{D5}$ under basic condition, in a solvent that does not adversely influence the reaction.

The amount of the halide corresponding to $R^{D5}$ to be used is generally 1 to 20 mol, preferably 1 to 10 mol, per 1 mol of compound (DIV).

Where necessary, a base may be used for the reaction under basic condition. Examples of the base include sodium hydride, sodium t-butoxide, sodium carbonate, potassium carbonate, cesium carbonate and the like.

The amount of the base to be used is generally 1 to 20 mol, preferably 1 to 10 mol, per 1 mol of compound (DIV).

In addition, an additive such as lithium hydroxide, lithium chloride, lithium bromide, lithium iodide and the like may be added in the reaction system, as necessary.

The amount of the additive to be used is generally 1 to 20 mol, preferably 1 to 10 mol, per 1 mol of compound (DIV).

Examples of the solvent that does not adversely influence the reaction include ethers, alcohols, hydrocarbons, ketones, nitriles, amides, esters, and the like, and ethers, nitriles and amides are particularly preferable. Two or more kinds of the above-mentioned solvents may mixed in an appropriate ratio and used.

The reaction temperature is generally 0 to 130° C., preferably 20 to 100° C.

The reaction time is generally 0.5 to 100 hr, preferably 1 to 48 hr.

The halide corresponding to $R^{D5}$ may be commercially available product, or can be produced from the corresponding starting material compound according to a method known per se.

The reaction from compound (DIII) to compound (DII) can be carried out by subjecting compound (DIII) to hydrolysis in the presence of an acid or a base, in a solvent that does not adversely influence the reaction.

Particularly, when $R^{D8}$ is benzyl, a catalytic hydrogenation can be employed in a solvent that does not adversely influence the reaction.

Examples of the acid include hydrochloric acid, sulfuric acid and the like.

Examples of the base include sodium hydroxide, potassium hydroxide, lithium hydroxide and the like.

The amount of the acid or base to be used is generally 1 to 20 mol, preferably 1 to 10 mol, per 1 mol of compound (DIII).

Examples of the catalyst for the catalytic hydrogenation include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (DIII).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. Two or more kinds of the above-mentioned solvents may mixed in an appropriate ratio and used.

The reaction temperature is generally 0 to 100° C., preferably 20 to 60° C.

The reaction time is generally 0.5 to 100 hr, preferably 1 to 48 hr.

The reaction from compound (DII) to compound (DI) can be carried out by subjecting compound (DII) to condensation with an amine corresponding to $R^{D2}$, using a condensing agent, in a solvent that does not adversely influence the reaction. Where necessary, a base such as tertiary amine and the like may be added.

Examples of the condensing agent include carbodiimides (e.g., dicyclohexylcarbodiimide (DCCD), water-soluble carbodiimide (WSCD)), phosphates (e.g., diethyl cyanophosphonate, diethyl chlorophosphonate, diphenylphosphoryl azide), BOP reagent (e.g., 1H-benzotriazol-1-yloxytripyrrolidinophosphonium hexafluorophosphate (PyBOP)), O-(7-azabenzotriazol-1-yl)-N,N,N',N'-tetramethyluronium hexafluorophosphate (HATU), 2-ethoxy-1-ethoxycarbonyl-1,2-dihydroquinoline (EEDQ), carbonyldiimidazole and the like, and WSCD and HATU are particularly preferable.

The amount of the amine corresponding to $R^{D2}$ to be used is generally 1 to 10 mol, preferably 1 to 2 mol, per 1 mol of compound (DII).

The amount of the condensing agent to be used is generally 1 to 10 mol, preferably 1 to 2 mol, per 1 mol of compound (DII).

Examples of the solvent that does not adversely influence the reaction include ethers, hydrocarbons, ketones, nitriles, amides, esters and the like, and ethers and amides are particularly preferable. Two or more kinds of the above-mentioned solvents may mixed in an appropriate ratio and used.

The reaction temperature is generally 0 to 100° C., preferably 20 to 60° C.

The reaction time is generally 0.5 to 100 hr, preferably 1 to 48 hr.

The amine corresponding to $R^{D2}$ may be commercially available product, or can be produced from the corresponding starting material compound according to a method known per se.

Compound (DVI) can be produced, for example, according to the following [Method DB] or a method analogous thereto.

[Method DB]

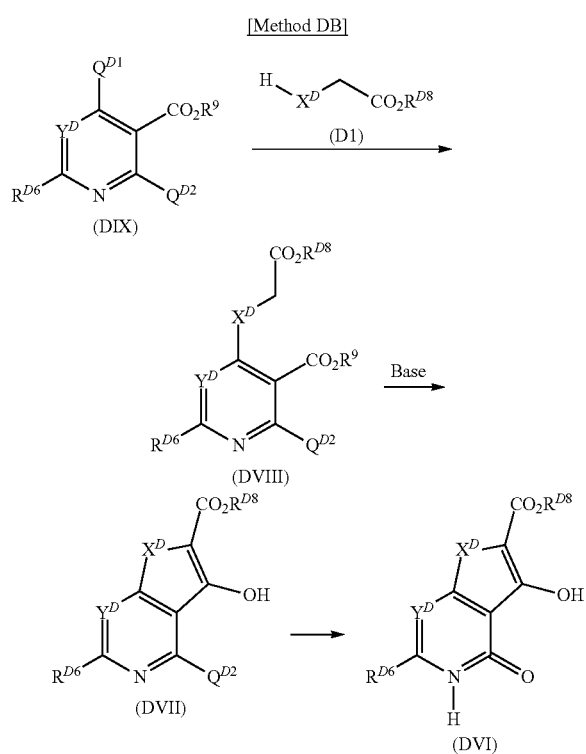

wherein $Q^{D1}$ and $Q^{D2}$ are independently a leaving group, and other symbols are as defined above.

Examples of the leaving group for $Q^{D1}$ or $Q^{D2}$ include those exemplified as the above-mentioned $Q^{D3}$ and a halogen atom, and a halogen atom is particularly preferable.

The reaction of compound (DIX) with compound (D1) can be carried out in a solvent that does not adversely influence the reaction, in the presence of a base, as necessary.

The amount of compound (D1) to be used is generally 1 to 20 mol, preferably 1 to 10 mol, per 1 mol of compound (DIX).

Examples of the base include sodium hydride, sodium methoxide, sodium ethoxide, sodium carbonate, sodium hydrogen carbonate, sodium hydroxide, triethylamine, diisopropylethylamine, pyridine, 4-dimethylaminopyridine and the like.

The amount of the base to be used is generally 2 to 20 mol, preferably 2 to 15 mol, per 1 mol of compound (DIX).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally 0 to 100° C., preferably 20 to 90° C.

The reaction time is generally 0.5 to 100 hr, preferably 1 to 48 hr.

Compound (D1) may be commercially available product, or can be synthesized according to a method known per se.

The reaction from compound (DVIII) to compound (DVII) can be carried out by reacting compound (DVIII) with a base in a solvent that does not adversely influence the reaction.

Examples of the base include sodium methoxide, sodium ethoxide, sodium hydroxide and the like.

The amount of the base to be used is generally 2 to 5 mol, preferably 2 to 3 mol, per of 1 mol of compound (DVIII).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally 0 to 100° C., preferably 20 to 90° C.

The reaction time is generally 0.5 to 100 hr, preferably 1 to 48 hr.

Compound (DVII) can also be obtained directly from compound (DIX) without isolation of compound (DVIII).

The reaction from compound (DVII) to compound (DVI) can be carried out by subjecting compound (DVII) to hydrolysis in the presence of an acid or a base, in a solvent that does not adversely influence the reaction.

The hydrolysis may be carried out after converting $Q^{D2}$ of compound (DVII) to acetoxy or alkoxy, or directly in the presence of a base or an acid.

The conversion of $Q^{D2}$ of compound (DVII) to acetoxy or alkoxy can be carried out, for example, by reacting compound (DVII) with sodium acetate, sodium methoxide or sodium ethoxide.

The amount of the sodium acetate, sodium methoxide or sodium ethoxide to be used is generally 1 to 20 mol, preferably 1 to 10 mol, per 1 mol of compound (DVII).

Examples of the acid include acetic acid, hydrochloric acid, sulfuric acid, methanesulfonic acid and the like.

Examples of the base include aqueous sodium hydroxide solution, aqueous potassium hydroxide solution, aqueous lithium hydroxide solution and the like.

The amount of the acid or base to be used is generally 1 to 20 mol, preferably 1 to 10 mol, per 1 mol of compound (DVII).

Examples of the solvent that does not adversely influence the reaction include ethers, hydrocarbons, alcohols, ketones, nitriles, amides, water and the like, and ethers and amides are particularly preferable, water. Two or more kinds of the above-mentioned solvents may mixed in an appropriate ratio and used.

The reaction temperature is generally 0 to 130° C., preferably 20 to 100° C.

The reaction time is generally 0.5 to 100 hr, preferably 1 to 48 hr.

Compound (DIX-2), which is compound (DIX) wherein $Y^D$ is a nitrogen atom, can be produced, for example, according to the following [Method DC] or a method analogous thereto.

[Method DC]

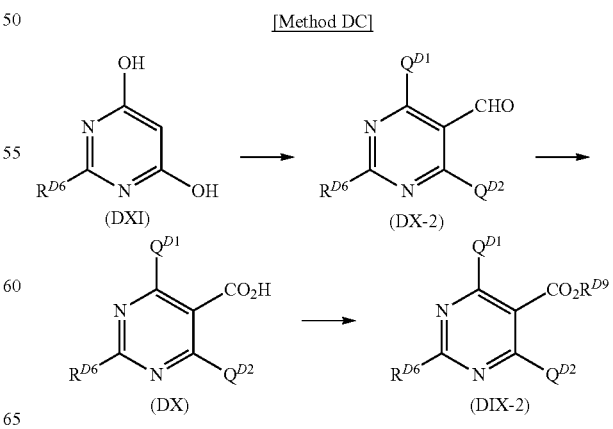

wherein each symbol is as defined above.

The reaction from compound (DXI) to compound (DX-2) can be carried out by reacting compound (DXI) with the Vilsmeier reagent, in a solvent that does not influence the reaction.

Examples of the Vilsmeier reagent include DMF-phosphorus oxychloride, DMF-thionyl chloride and the like.

The amount of the DMF to be used is generally 1 to 2 mol, preferably 1 to 1.5 mol, per 1 mol of compound (DXI).

The amount of the phosphorus oxychloride or thionyl chloride to be used is generally 1 to 20 mol, preferably 1 to 10 mol, per 1 mol of compound (DX DXI).

Examples of the solvent that does not influence the reaction include ethers, hydrocarbons, nitriles, esters and the like, and ethers and nitriles are particularly preferable. Two or more kinds of the above-mentioned solvents may mixed in an appropriate ratio and used.

The reaction temperature is generally 0 to 180° C., preferably 0 to 150° C.

The reaction time is generally 0.5 to 48 hr, preferably 1 to 24 hr. Compound (DXI) can be synthesized according to a method known per se (e.g., the method described in Journal of Heterocyclic Chemistry, vol. 13, pages 1141-1144, 1976).

The reaction from compound (DX-2) to compound (DX) can be carried out by reacting compound (DX-2) with an oxidant in a solvent that does not influence the reaction.

Examples of the oxidant include sodium chlorite, potassium permanganate, m-chloroperbenzoic acid, hydrogen peroxide, oxygen and the like.

The amount of the oxidant to be used is generally 1 to 3 mol, preferably 1 to 2 mol, per 1 mol of compound (DX-2).

Examples of the solvent that does not adversely influence the reaction include alcohols, nitriles, amides, water and the like, and amides and water are particularly preferable. Two or more kinds of the above-mentioned solvents may mixed in an appropriate ratio and used.

The reaction temperature is generally 0 to 60° C., preferably 20 to 40° C.

The reaction time is generally 0.5 to 48 hr, preferably 1 to 24 hr.

The reaction from compound (DX) to compound (DIX-2) can be carried out, for example, by converting compound (DX), which is a carboxylic acid, to the corresponding acid chloride, and then the acid chloride with an alcohol corresponding to $R^{D9}$.

The conversion of the carboxylic acid to the acid chloride can be carried out by reacting compound (DX) with a halogenating agent, in a solvent that does not influence the reaction.

Examples of the halogenating agent include oxalyl chloride, thionyl chloride, phosphoryl chloride, phosphorus pentachloride, phosphorus tribromide and the like.

The amount of the halogenating agent to be used is generally 1 to 5 mol, preferably 1 to 2 mol, per 1 mol of compound (DX).

In addition, DMF may be added to this reaction system.

The amount of the DMF to be used is generally 1 to 2 mol, preferably 1 to 1.5 mol, per 1 mol of compound (DX).

Examples of the solvent that does not adversely influence the reaction include ethers, hydrocarbons, ketones, nitriles, amides, esters and the like, and hydrocarbons, ethers and nitriles are particularly preferable. Two or more kinds of the above-mentioned solvents may mixed in an appropriate ratio and used.

The reaction temperature is generally 0 to 80° C., preferably 20 to 40° C.

The reaction time is generally 0.5 to 48 hr, preferably 1 to 24 hr.

The reaction of the acid chloride with an alcohol corresponding to $R^{D9}$ can be carried out in a solvent that does not influence the reaction, in the presence of a base, as necessary.

The amount of the alcohol corresponding to $R^{D9}$ to be used is generally 1 to 5 mol, preferably 1 to 2 mol, per 1 mol of the acid chloride.

Examples of the base include triethylamine, N,N-diisopropylethylamine, pyridine and the like.

The amount of the base to be used is generally 1 to 5 mol, preferably 1 to 2 mol, per 1 mol of the acid chloride.

Examples of the solvent that does not adversely influence the reaction include ethers, hydrocarbons, ketones, nitriles, amides, esters and the like, and ethers, nitriles and amides are particularly preferable. Two or more kinds of the above-mentioned solvents may mixed in an appropriate ratio and used.

The reaction temperature is generally 0 to 80° C., preferably 20 to 40° C.

The reaction time is generally 0.5 to 48 hr, preferably 1 to 24 hr.

Compound (DIX-3), which is compound (DIX) wherein $Y^D$ is CH, can also be produced, for example, according to the following [Method DD] or a method analogous thereto.

[Method DD]

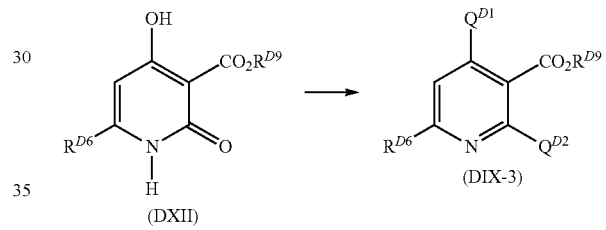

wherein each symbol is as defined above.

The reaction from compound (DXII) to compound (DIX-3) can be carried out using a halogenating reagent in a solvent that does not adversely influence the reaction or without solvent, in the presence of a base, as necessary.

Examples of the halogenating reagent include thionyl chloride, phosphoryl chloride, phosphorus pentachloride, phosphorus tribromide and the like.

The amount of the halogenating reagent to be used is generally 1 to 20 mol, preferably 2 to 10 mol, per 1 mol of compound (DXII).

Examples of the base include triethylamine, diisopropylethylamine, pyridine, 4-dimethylaminopyridine and the like.

The amount of the base to be used is generally 1 to 20 mol, preferably 2 to 10 mol, per 1 mol of compound (DXII).

Examples of the solvent that does not adversely influence the reaction include ethers, hydrocarbons, alcohols, amides, esters and the like. Two or more kinds of the above-mentioned solvents may mixed in an appropriate ratio and used. This reaction is preferably carried out without solvent.

The reaction temperature is generally 0 to 130° C., preferably 20 to 130° C.

The reaction time is generally 0.5 to 100 hr, preferably 1 to 48 hr.

Alternatively, The reaction from compound (DXII) to compound (DIX-3) can be carried out using a sulfonylating reagent in a solvent that does not adversely influence the reaction or without solvent, in the presence of a base, as necessary.

Examples of the sulfonylating reagent include trifluoromethanesulfonic anhydride, methanesulfonyl halides optionally having 1 to 3 halogen atoms, benzenesulfonyl halides optionally having 1 to 3 $C_{1-6}$ alkyl groups and the like.

The amount of the sulfonylating reagent to be used is generally 1 to 2 mol, preferably 1 to 1.5 mol, per 1 mol of compound (DXII).

Examples of the base include triethylamine, diisopropylethylamine, pyridine, 4-dimethylaminopyridine and the like.

The amount of the base to be used is generally 2 to 5 mol, preferably 2 to 3 mol, per 1 mol of compound (DXII).

Examples of the solvent that does not adversely influence the reaction include ethers, hydrocarbons, alcohols, amides, esters and the like, and ethers and amides are particularly preferable. Two or more kinds of the above-mentioned solvents may mixed in an appropriate ratio and used.

The reaction temperature is generally −10 to 100° C., preferably 0 to 60° C.

The reaction time is generally 0.5 to 100 hr, preferably 1 to 48 hr.

Compound (DXII) can be synthesized according to a method known per se (for example, the method described in Journal of Medicinal Chemistry, vol. 51, pages 1385-1392, 2008).

Compound (DIII-3), which is compound (DIII) wherein $Y^D$ is CH, can also be produced, for example, according to the following or a method analogous thereto.

[Method DE]

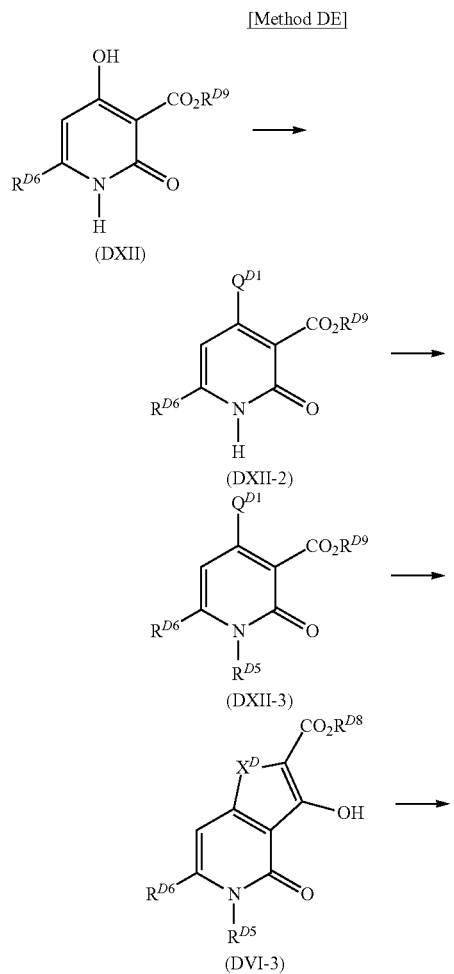

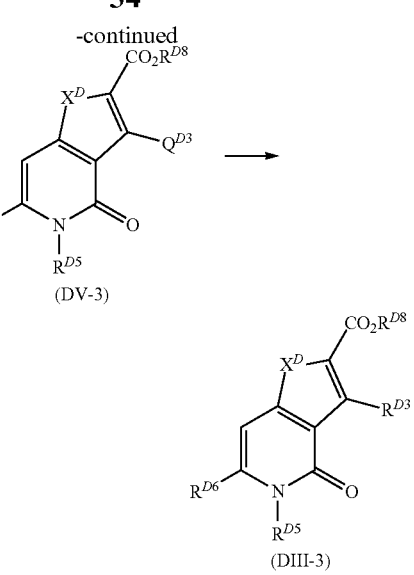

wherein each symbol is as defined above.

The reaction from compound (DXII) to compound (DXII-2) can be carried out according [Method DD], while adjusting the amount of the reagent and the reaction time.

The reaction from compound (DXII-2) to compound (DXII-3) can be carried out according to the reaction from compound (DIV) to compound (DIII) shown in [Method DA].

The reaction from compound (DXII-3) to compound (DVI-3) can be carried out according to the reaction from compound (DIX) to compound (DVII) shown in [Method DB].

The reaction from compound (DVI-3) to compound (DV-3) can be carried out according to the reaction from compound (DVI) to compound (DV) shown in [Method DA].

The reaction from compound (DV-3) to compound (DIII-3) can be carried out according to the reaction from compound (DV) to compound (DIV) shown in [Method DA].

When $R^{D5}$ is reduced during the reduction reaction, compound (DIII-3) can also be synthesized by oxidizing $R^{D5}$.

Examples of the oxidant include a combination of 4-methylmorpholine N-oxide and tetrapropylammonium perruthenate, and the like. The amount of the 4-methylmorpholine N-oxide to be used is generally 1 to 10 mol per 1 mol of the reduced compound, and the amount of the tetrapropylammonium perruthenate to be used is generally 0.01 to 0.5 mol per 1 mol of the reduced compound.

Examples of the solvent that does not adversely influence the reaction include hydrocarbons, alcohols, amides, nitriles, esters and the like, and nitriles are particularly preferable. Two or more kinds of the above-mentioned solvents may mixed in an appropriate ratio and used.

The reaction temperature is generally −10 to 60° C., preferably 1.0 to 40° C.

The reaction time is generally 0.5 to 100 hr, preferably 1 to 48 hr.

Compound (DI) can also be produced by the above-mentioned reaction combined with, when desired, one or two or more of known hydrolysis, deprotection, acylation reaction, alkylation reaction, oxidation reaction, cyclization reaction, carbon chain extension reaction and substituent exchange reaction.

Compound (DIII-4), which is compound (DIII-3) wherein $R^{D3}$ is an amino group optionally having substituent(s), can also be produced, for example, according to the following [Method DF] or a method analogous thereto.

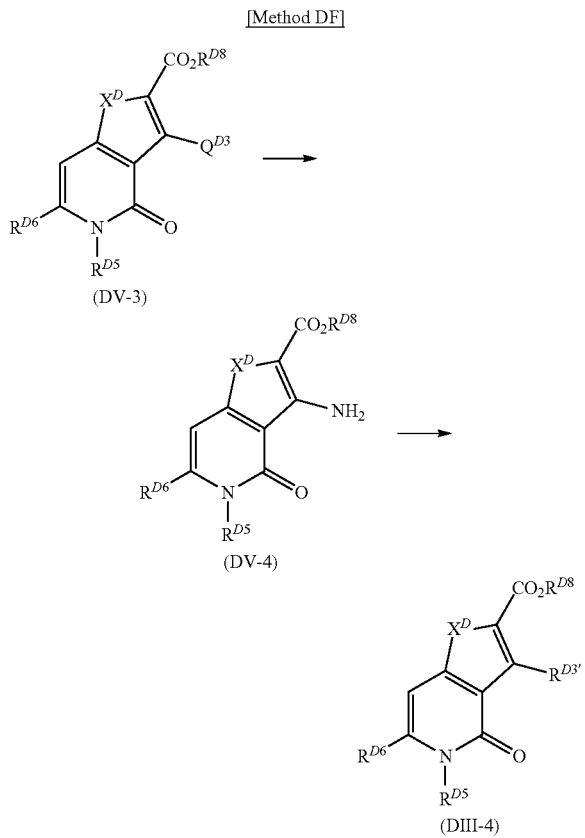

wherein $R^{D3'}$ is an amino group optionally having substituent(s), and other symbols are as defined above.

The reaction from compound (DV-3) to compound (DV-4) can be carried out, for example, by reacting compound (DV-3) with benzophenonimine, and then subjecting the resulting compound to hydrolysis.

The reaction of compound (DV-3) with benzophenonimine can be carried out in the presence of a base and a metal complex, in a solvent that does not adversely influence the reaction.

The amount of the benzophenonimine to be used is generally 1 to 5 mol, preferably 1 to 2 mol, per 1 mol of compound (DV-3).

Examples of the base include cesium carbonate, potassium carbonate, sodium t-butoxide and the like.

The amount of the base to be used is generally 1 to 5 mol, preferably 1 to 3 mol, per 1 mol of compound (DV-3).

Examples of the metal complex include a complex consisting of tris(dibenzylideneacetone)dipalladium(0) and 4,5'-bis(diphenylphosphino)-9,9'-dimethylxanthene.

The amount of the complex to be used is generally 0.05 to 1 mol, preferably 0.1 to 0.5 mol, per 1 mol of compound (DV-3).

Examples of the solvent that does not adversely influence the reaction include ethers, alcohols, hydrocarbons, ketones, nitriles, amides, esters and the like, and ethers and hydrocarbons are particularly preferable. Two or more kinds of the above-mentioned solvents may mixed in an appropriate ratio and used.

The reaction temperature is generally 0 to 100° C., preferably 20-80° C.

The reaction time is generally 0.5 to 100 hr, preferably 1 to 48 hr.

The hydrolysis can be carried out under acidic conditions, in a solvent that does not adversely influence the reaction.

Examples of the acid include hydrochloric acid, sulfuric acid, methanesulfonic acid and the like.

Examples of the solvent that does not adversely influence the reaction include alcohols, nitriles, amides and the like, and alcohols and amides are particularly preferable. Two or more kinds of the above-mentioned solvents may mixed in an appropriate ratio and used.

The reaction temperature is generally 0 to 60° C., preferably 20 to 40° C.

The reaction time is generally 0.5 to 48 hr, preferably 1 to 24 hr.

The reaction from compound (DV-4) to compound (DIII-4) can be carried out, for example, by subjecting compound (DV-4) to reduction alkylation reaction using a combination of a carbonyl compound and a reducing agent, or to substitution reaction which is a reaction with an alkyl group having a leaving group or an acyl group. In addition, these reactions may be combined.

The reduction alkylation reaction can be carried out, for example, using a carbonyl compound corresponding to the "substituent" of the "amino group optionally having substituent(s)" for $R^{D3'}$ and a reducing agent, in a solvent that does not adversely influence the reaction, in the presence of an acid, as necessary.

The amount of the carbonyl compound to be used is generally 1 to 3 mol, preferably 1 to 2 mol, per 1 mol of compound (DV-4).

Examples of the reducing agent include sodium borohydride, sodium triacetoxyborohydride, sodium cyanoborohydride and the like.

The amount of the reducing agent to be used is generally 1 to 5 mol, preferably 1 to 3 mol, per 1 mol of compound (DV-4).

Examples of the acid include hydrochloric acid, p-toluenesulfonic acid, acetic acid and the like.

The amount of the acid to be used is generally 1 to 5 mol, preferably 1 to 3 mol, per 1 mol of compound (DV-4).

Examples of the solvent that does not adversely influence the reaction include alcohols, ethers, hydrocarbons, nitriles, amides and the like, and alcohols, ethers and amides are particularly preferable. Two or more kinds of the above-mentioned solvents may mixed in an appropriate ratio and used.

The reaction temperature is generally 0 to 60° C., preferably 0 to 40° C.

The reaction time is generally 0.5 to 48 hr, preferably 1 to 24 hr.

The carbonyl compound corresponding to the "substituent" of the "amino group optionally having substituent(s)" for $R^{D3'}$ may be commercially available product, or can be produced from the corresponding starting material compound according to a method known per se.

The alkylation reaction can be carried out, for example, using an alkyl halide compound corresponding to the "substituent" of the "amino group optionally having substituent(s)" for $R^{D3'}$, in a solvent that does not adversely influence the reaction, in the presence of a base, as necessary.

The amount of the alkyl halide compound to be used is generally 1 to 3 mol, preferably 1 to 2 mol, per 1 mol of compound (DV-4).

Examples of the base include sodium methoxide, sodium ethoxide, cesium carbonate, sodium carbonate, potassium carbonate, sodium hydrogen carbonate, sodium hydroxide, triethylamine, diisopropylethylamine, pyridine, 4-dimethylaminopyridine, 1,8-diazabicyclo[5.4.0]undec-7-ene (DBU) and the like, and pyridine, triethylamine and diisopropylethylamine are particularly preferable.

The amount of the base to be used is generally 1 to 5 mol, preferably 1 to 3 mol, per 1 mol of compound (DV-4).

Examples of the solvent that does not adversely influence the reaction include alcohols, ethers, hydrocarbons, nitriles, amides and the like, and ethers and amides are particularly preferable. Two or more kinds of the above-mentioned solvents may mixed in an appropriate ratio and used.

The reaction temperature is generally 0 to 60° C., preferably 0 to 40° C.

The reaction time is generally 0.5 to 48 hr, preferably 1 to 24 hr.

The alkylhalide compound corresponding to the "substituent" of the "amino group optionally having substituent(s)" for $R^{D3'}$ may be commercially available product, or can be produced from the corresponding starting material compound according to a method known per se.

The acylation reaction can be carried out, for example, using an acid chloride corresponding to the "substituent" of the "amino group optionally having substituent(s)" for $R^{D3'}$, in the presence of a base, in a solvent that does not adversely influence the reaction.

The amount of the acid chloride to be used is generally 1 to 3 mol, preferably 1 to 2 mol, per 1 mol of compound (DV-4).

Examples of the base include sodium methoxide, sodium ethoxide, cesium carbonate, sodium carbonate, potassium carbonate, sodium hydrogen carbonate, sodium hydroxide, triethylamine, diisopropylethylamine, pyridine, 4-dimethylaminopyridine, 1,8-diazabicyclo[5.4.0]undec-7-ene (DBU) and the like, and pyridine, triethylamine and diisopropylethylamine are particularly preferable.

The amount of the base to be used is generally 1 to 5 mol, preferably 1 to 3 mol, per 1 mol of compound (DV-4).

Examples of the solvent that does not adversely influence the reaction include ethers, hydrocarbons, ketones, nitriles, amides, esters and the like, and ethers and amides are particularly preferable. Two or more kinds of the above-mentioned solvents may mixed in an appropriate ratio and used.

The reaction temperature is generally 0 to 60° C., preferably 0 to 40° C.

The reaction time is generally 0.5 to 48 hr, preferably 1 to 24 hr.

The acid chloride corresponding to the "substituent" of the "amino group optionally having substituent(s)" for $R^{D3'}$ can be produced from the corresponding starting material compound according to a method known per se.

Compound (DI) can be isolated and purified by a means known per se, such as phase transfer, concentration, solvent extraction, fractionation, liquid conversion, crystallization, recrystallization, chromatography and the like. When compound (DI) is obtained as a free compound, it can be converted to a desired salt by a method known per se or a method analogous thereto. Conversely, when the compound is obtained as a salt, it can be converted to a free form or other desired salt by a method known per se or a method analogous thereto.

A compound within the scope of the present invention can also be produced by applying a means known per se to compound (DI) for introduction of substituents and conversion of functional groups. For conversion of substituents, a known conventional method can be used. For example, conversion to amino by hydrolysis of amide, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination by reduction of nitro, alkylation of hydroxy, substitution and amination of hydroxy and the like. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby the compound within the scope of the present invention can also be produced.

Compound (DI) may be used as a prodrug. A prodrug of compound (DI) means a compound converted to compound (DI) by a reaction due to an enzyme, a gastric acid, etc. under the physiological condition in the living body, that is, a compound converted to compound (DI) by oxidation, reduction, hydrolysis, etc. due to an enzyme, a compound converted to compound (DI) by hydrolysis etc. due to gastric acid, and the like.

Examples of the prodrug of compound (DI) include a compound obtained by subjecting amino in compound (DI) to an acylation, alkylation or phosphorylation (e.g., a compound obtained by subjecting amino in compound (DI) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (DI) to acylation, alkylation, phosphorylation or boration (e.g., a compound obtained by subjecting hydroxy in the compound (DI) to acetylation, palmitoylation, propanoylation, pivaloylation, succinylation, fumarylation, alanylation or dimethylaminoacethylation); a compound obtained by subjecting carboxy in compound (DI) to esterification or amidation (e.g., a compound obtained by subjecting carboxy in compound (DI) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (DI) by a method known per se.

A prodrug of compound (DI) may also be a compound converted into compound (DI) under physiological conditions, such as those described in IYAKUHIN no KAIHATSU (Development of Pharmaceuticals), Vol. 7, Design of Molecules, p. 163-198, Published by HIROKAWA SHOTEN (1990).

When compound (DI) has an isomer such as optical isomer, stereoisomer, positional isomer, rotational isomer and the like, any isomer and a mixture thereof are encompassed in compound (DI). For example, when compound (DI) has an optical isomer, an optical isomer resolved from a racemate is also encompassed in compound (DI). Such isomers can be obtained as independent products by a synthesis means or a separation means (concentration, solvent extraction, column chromatography, recrystallization and the like) known per se.

Compound (DI) may be a crystal, and both a single crystal and crystal mixtures are encompassed in compound (DI).

Crystals can be produced by crystallization according to crystallization methods known per se.

Compound (DI) may also be a cocrystal.

Compound (DI) may be a hydrate, a non-hydrate, a solvate or a non-solvate.

A compound labeled with an isotope (e.g., $^2$H, $^3$H, $^{14}$C, $^{35}$S, $^{125}$I etc.) is also encompassed in compound (DI).

Compound (DI) may be a deuterium conversion.

Compound (DI) or a prodrug thereof (sometimes to be abbreviated as "the compound of the present invention" in the present specification) interacts, for example, with human Smo protein and changes the steric structure thereof, whereby formation of a complex with a protein involved in the signal transduction in the cytoplasm is inhibited and the Hedgehog signal transduction system is inhibited. Alternatively, the compound of the present invention interacts with human Smo protein and directly inhibits formation of a complex of human Smo protein with a protein involved in the Hedgehog signal transduction system in the cytoplasm, whereby the Hedgehog signal transduction system is inhibited. Alternatively, the compound of the present invention interacts with a site of an Smo protein, for example, phosphorylation site and the like, which is modified by a protein involved in the Hedgehog signal transduction system, whereby modification such as phosphorylation of Smo and the like is inhibited and the Hedgehog signal transduction system is inhibited.

Inhibition of the Hedgehog signal transduction system can be measured, for example, by quantifying a decrease in the expression level of a reporter gene connected to the downstream of the Gli binding site based on the fluorescence intensity according to the following Experimental Example 1. Alternatively, it can be measured by quantifying the expression of Gli-1 mRNA in a cell extract by quantitative PCR method and the like. A compound that inhibits Hedgehog signal targets Smo, which can be confirmed, for example, by binding fluorescence-labeled Cyclopamine and a test compound to cells expressing Smo, measuring the fluorescence level of the cell, and comparing the value with that without addition of a test compound to find a decrease.

Accordingly, the compound of the present invention is useful as an Smo inhibitor for mammals (e.g., mouse, rat, hamster, rabbit, cat, dog, bovine, sheep, monkey, human). The compound of the present invention is used as a medicament of diseases possibly influenced by Smo, for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, esophagus cancer, gastric cancer (e.g., papillary adenocarcinoma, mucinous adenocarcinoma, adenosquamous cancer), duodenal cancer, small intestinal cancer, breast cancer (e.g., invasive ductal breast carcinoma, ductal cancer in situ, inflammatory breast cancer), ovarian cancer (e.g., ovarian epithelial cancer, extragonadal germ cell tumor, ovarian germ cell tumor, ovarian low malignant potential tumor), testicular tumor, prostate cancer (e.g., hormone-dependent prostate cancer, non-hormone dependent prostate cancer), liver cancer (e.g., hepatocellular carcinoma, primary liver cancer, bile duct cancer, extrahepatic bile duct cancer), thyroid cancer (e.g., medullary, thyroid cancer), kidney cancer (e.g., renal cell carcinoma, renal pelvis and ureter transitional cell cancer), uterine cancer (e.g., cervical cancer, cancer of uterine body, uterine sarcoma), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell carcinoma, malignant melanoma), sarcoma (e.g., rhabdomyosarcoma, leiomyosarcoma, soft tissue sarcoma), malignant bone tumor, urinary bladder cancer, hematologic cancer (e.g., multiple myeloma, leukemia, malignant lymphoma, Hodgkin's disease, chronic myeloproliferative disorder), cancer unknown primary], a cancer growth inhibitor, a cancer metastasis inhibitor, an apoptosis promoter and the like.

Among these, the compound of the present invention is effective, for example, for brain tumor, skin cancer, lung cancer, pancreatic cancer, biliary tract cancer, prostate cancer, esophagus cancer, gastric cancer, colorectal cancer, sarcoma and breast cancer.

Especially, the compound of the present invention is effective for glioma, medulloblastoma, basal cell tumor, small cell lung cancer, pancreatic cancer, biliary tract cancer, prostate cancer, esophagus cancer, gastric cancer, colorectal cancer, rhabdomyosarcoma and breast cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, crystalline cellulose, powdered glycyrrhiza, mannitol, sodium hydrogen carbonate, calcium phosphate, calcium sulfate and the like.

Examples of the binder include 5 to 10 wt % starch liquid paste, 10 to 20 wt % gum arabic solution or gelatin solution, 1 to 5 wt % tragacanth solution, carboxymethyl cellulose solution, sodium alginate solution, glycerin and the like.

Examples of the disintegrant include starch, calcium is carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride) and the like, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like can be blended. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 is portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, epristeride), aderenal cortex hormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid hormone, and DDS (Drug Delivery System) preparations thereof, and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" in the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα], (2) insulin or substances possessing substantially the same activity as insulin [e.g., insulin, IGF (insulin-like growth factor)-1, IGF-2], (3) FGF (fibroblast growth factor) or substances possessing substantially the same activity as FGF [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

Examples of the "cell growth factor receptors" include any receptors capable of binding to the aforementioned cell growth factors, including EGF receptor, heregulin receptor (HER3, etc.), insulin receptor inhibitor, IGF receptor-1, IGF receptor-2, FGF receptor-1 or FGF receptor-2, VEGF receptor, angiopoietin receptor (Tie2 etc.), PDGF receptor, c-MET, c-Kit, Trk and the like.

Examples of the "medicaments inhibiting the action of cell growth factors or cell growth factor receptors" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, MEK(MEK1/2) inhibitor, MET inhibitor, Akt inhibitor, ERK inhibitor and the like. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl) phenyl]-N-[1(R)-phenylethyl]-7H-pyrrolo[2,3-d]pyrimidin-4-amine (AEE-788), Vandetanib, Temsirolimus, Everolimus, Sirolimus, Enzastaurin, N-[4-[4-(4-methylpiperazin-1-yl)-6-(3-methyl-1H-pyrazol-5-ylamino)pyrimidin-2-ylsulfanyl] phenyl]cyclopropanecarboxamide (VX-680), 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 2-hydroxyethyl 5-(4-bromo-2-chlorophenylamino)-4-fluoro-1-methyl-1H-benzimidazole-6-carbohydroxamate (AZD-6244), N-[2(R),3-dihydroxypropoxy]-3,4-difluoro-2-(2-fluoro-4-iodophenylamino)benzamide (PD-0325901) and the like are used.

In addition to the aforementioned drugs, cell cycle inhibitors (e.g., Aurora A inhibitors, Aurora B inhibitors, PLK inhibitors, CDK inhibitors), pro-apoptotic agents (e.g., Bcl-2 inhibitors, IAP inhibitors, Nedd-8 inhibitors), proteasome inhibitors (e.g., bortezomib), (Hedgehog signal inhibitors (e.g., Vismodegib, LDE225, IPI-926), Wnt signal inhibitors (e.g., β-catenin/TCF inhibitors, anti-Wnt antibody), Notch signal inhibitors (e.g., anti-Notch antibody, γ-secretase inhibitors), L-asparaginase, aceglatone, procarbazine hydrochloride, protoporphyrin-cobalt complex salt, mercuric hematoporphyrin-sodium, topoisomerase I inhibitors (e.g., irinotecan, topotecan), topoisomerase II inhibitors (e.g., sobuzoxane), differentiation inducers (e.g., retinoid, vitamin D), other angiogenesis inhibitors (e.g., humagillin, shark extract, COX-2 inhibitor), α-blockers (e.g., tamsulosin hydrochloride), bisphosphonic acids (e.g., pamidronate, zoledronate), thalidomide, 5-azacytidine, decitabine, antitumor antibody such as anti-CD20 antibody and the like, toxin labeled antibody and the like can also be used.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is appropriately determined in accordance with its clinical dose, and the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous). An injection can be administered by intravenous, intramuscular, subcutaneous or intra-organ administration, or directly to the lesion.

As a pharmacologically acceptable carrier which may be used for preparing the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage form, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin), a stabilizer (e.g., ascorbic acid, sodium pyrosulfite), a surfactant (e.g., Polysorbate 80, macrogol), a solubilizer (e.g., glycerin, methanol), a buffer (e.g., phosphoric acid and alkali metal salt thereof, citric acid and alkali metal salt thereof), an isotonizing agent (e.g., sodium chloride, potassium chloride, mannitol, sorbitol, glucose), a pH adjuster (e.g., hydrochloric acid, sodium hydroxide), a preservative (e.g., ethyl paraoxybenzoate, benzoic acid, methylparaben, propylparaben, benzyl alcohol), a dissolving agent (e.g., conc. glycerin, meglumine), a solubilizing agent (e.g., propylene glycol, sucrose), a soothing agent (e.g., glucose, benzyl alcohol), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch), a disintegrating agent (e.g., starch, calcium carbonate), a binder (e.g., starch, gum arabic, carboxymethylcellulose, polyvinylpyrrolidone, hydroxypropylcellulose), a lubricant (e.g., talc, magnesium stearate, polyethylene glycol 6000) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid.acrylic acid copolymer, manufactured by Rohm, DE), pigment (e.g., iron oxide red, titanium dioxide) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany)], glycerides of medium chain fatty acid [e.g., Miglyols (manufactured by Dynamit Nobel, Germany)], or vegetable oils (e.g., sesame oil, soybean oil, cotton seed oil), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof.

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as trometamol and the like, etc. are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

The injection of the present invention appropriately contains additives usually used in an injection, for example, a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride), a dispersing agent (e.g., hydroxypropylmethylcellulose, dextrin), a pH regulator (e.g., hydrochloric acid, sodium hydroxide), a preservative (e.g., ethyl parahydroxybenzoate, benzoic acid), a dissolving agent (e.g., conc. glycerin, meglumine), a solubilizing agent (e.g., propylene glycol, sucrose), a soothing agent (e.g., glucose, benzyl alcohol), and the like. These additives are generally blended in a proportion usually used in an injection.

It is advantageous that pH of an injection be controlled from pH 2 to 12, preferably from pH 2.5 to 8.0, by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof.

A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethylchloride methacrylate/ethyl ammonium copolymer), Eudoragit NE-30D (methyl methacrylate/ethyl acrylate copolymer), and the like, hydrogenated oils such as hydrogenated castor oil (e.g., LUBRI WAX; Freund Corporation)), waxes such as carnauba wax, fatty acid glycerin ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (all of which are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained release preparation is from about 30 to about 90% (w/w), preferably from about 35 to about 80% (w/w), further preferably, from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably the nucleus is formed into particles such as a granule or fine particle.

When the nucleus is composed of granules or fine particles, the average particle size thereof is preferably from about 150 to about 2000 μm, further preferably from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral administration agents and parenteral administration agents such as an injection and the like are used, and oral administration agents are preferable.

The immediate-release preparation, usually, may contain, in addition to an active component drug, also carriers, additives and excipients conventionally used in the pharmaceutical field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95 w/w %, preferably from about 1 to about 60 w/w % based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (Shin-Etsu Chemical Co., Ltd.), carboxymethylstarch (Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient and an excipient constituting the nucleus, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (Nippon Aerosil))), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule) or made into one preparation for oral administration appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof.

Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, β-cyclodextrin or β-cyclodextrin derivatives (e.g., hydroxypropyl-β-cyclodextrin) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably from about 10 to about 70% by weight. The content of the hydrophilic carrier in the whole preparation is from about 0.1 to about 50% by weight, preferably from about 10 to about 30% by weight. The content of the water-dispersible polymer in the whole preparation is from about 0.1 to about 30% by weight, preferably from about 10 to about 25% by weight. The content of the stabilizer in the whole preparation is from about 0.1 to about 10% by weight, preferably from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg body weight of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is explained in detail in the following by referring to Reference Examples, Examples, Formulation Examples and Experimental Examples, which are not to be construed as limitative.

In the Reference Examples and Examples, the purity of the compounds was measured under the following HPLC conditions.

measurement device: SHIMADZU Corporation LC-10 Avp system
column: CAPSEL PAK C18UG120 S-3 μm, 2.0×50 mm
solvent: Solution A; 0.1% trifluoroacetic acid-containing water,
  Solution B; 0.1% trifluoroacetic acid-containing acetonitrile
gradient cycle: 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)
injection volume: 2 μl
flow rate: 0.5 ml/min
detection method: UV 220 nm
  In the Reference Examples and Examples, the purification of the compounds by preparative HPLC was performed under the following conditions.
measurement device: Gilson Company Inc., High Throughput Purification System
column: YMC CombiPrep ODS-A, S-5 μm, 50×20 mm
detection method: UV 220 nm
solvent: Solution A; 0.1% trifluoroacetic acid-containing water,
  Solution B; 0.1% trifluoroacetic acid-containing acetonitrile
gradient cycle: representative example 0.00 min (SOLUTION A/SOLUTION B=98/2), 1.00 min (SOLUTION A/SOLUTION B=98/2), 5.20 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2), flow rate: 25 mL/min, or,
0.00 min (SOLUTION A/SOLUTION B=90/10), 1.00 min (SOLUTION A/SOLUTION B=90/10), 4.00 min (SOLUTION A/SOLUTION B=10/95), 8.50 min (SOLUTION A/SOLUTION B=10/95), 8.60 min (SOLUTION A/SOLUTION B=90/10), 8.70 min (SOLUTION A/SOLUTION B=90/10), flow rate: 20 mL/min
  In the Reference Examples and Examples, mass spectrum (MS) was measured under the following conditions.
measurement device: Micromass platform II or Waters ZMD
ionization method: Atmospheric Pressure Chemical Ionization (APCI) or electron impact ionization method (Electron Spray Ionization: ESI)
  In Reference Example and Example, HPLC-mass spectrum (LC-MS) was measured under the following conditions.
measurement device: Micromass ZMD, Agilent Technologies HP1100 and 1200 LC/MSD
column: CAPCELL PAK C18UG120, S-3 μm, 1.5×35 mm
solvent: SOLUTION A; 0.05% trifluoroacetic acid-containing water,
  SOLUTION B; 0.04% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.45 min (SOLUTION A/SOLUTION B=90/10)
injection volume: 2 μL, flow rate: 0.5 mL/min, detection method: UV 220 nm
ionization method: electron impact ionization method (Electron Spray Ionization: ESI)
  $^1$H NMR spectrum was measured using tetramethylsilane as the internal standard by AVANCE DPX-300 (300 MHz) manufactured by Bruker, AV-300M (300 MHz) manufactured by Bruker and VARIAN Mercury-300 (300 MHz), and all δ values were shown by ppm.

As the Microwave reaction apparatus, Emrys Optimizer, Biotage Japan Ltd. was used.
  Unless otherwise specified, the numerical value of mixed solvent shows a volume mixing ratio of each solvent. Unless otherwise specified, % means weight %. While the room temperature (ambient temperature) in the present specification means a temperature of from about 10° C. to about 35° C., it is not particularly strictly limited.
  Other abbreviations used in the specification mean the following:
s: singlet
d: doublet
t: triplet
q: quartet
m: multiplet
br: broad
J: coupling constant
Hz: hertz
$CDCl_3$: deuterated chloroform
DMSO-$d_6$: dimethyl sulfoxide-$d_6$
$CD_3OD$: deuterated methanol
$^1$H-NMR: proton nuclear magnetic resonance
DMF: N,N-dimethylformamide
THF: tetrahydrofuran
WSCD: water-soluble carbodiimide (1-ethyl-3-(3-dimethylaminopropyl)carbodiimide) hydrochloride
HOBt: 1-hydroxybenzotriazole
mCPBA: m-chloroperbenzoic acid
CDI: N,N'-carbonyldiimidazole
DMT-MM: 4-(4,6-dimethoxy-1,3,5-triazin-2-yl)-4-methylmorpholinium chloride
DPPA: diphenylphosphoryl azide
MeCN: acetonitrile
Pd(PPh$_3$)$_4$: tetrakis(triphenylphosphine)palladium(0)
OTf: [(trifluoromethyl)sulfonyl]oxy
Me: methyl
Et: ethyl
HATU: O-(7-azabenzotriazol-1-yl)-N,N,N',N'-tetramethyluronium hexafluorophosphate
DIPEA: diisopropylethylamine Reference Example 1

Production of methyl (2Z)-3-aminopent-2-enoate

A mixture of methyl 3-oxovalerate (75.0 g, 576 mmol), ammonium acetate (222 g, 2.88 mmol) and methanol (750 mL) was stirred at room temperature for 3 days. After concentration under reduced pressure, and water (500 mL) was added to the residue and the mixture was extracted with ethyl acetate (200 mL). The extract was washed with brine, dried over magnesium sulfate, concentrated under reduced pressure, and dried to give the title compound (68.5 g, 92%) as a pale-yellow oil.
  $^1$H-NMR (300 MHz, DMSO-$d_6$) δ: 1.06 (3H, t, J=7.6 Hz), 2.09 (2H, q, J=7.6 Hz), 3.49 (3H, s), 4.34 (1H, s), 6.94 (1H, s), 7.72 (1H, br s).

Reference Example 2

Production of ethyl 6-ethyl-4-hydroxy-2-oxo-1,2-dihydropyridine-3-carboxylate

To a solution of the compound of Reference Example 1 (50.0 g, 387 mmol) and diethyl malonate (58.8 mL, 387 mmol) in ethanol (400 mL) was added 20% ethanol solution (133 g) of sodium ethoxide, and the mixture was stirred at 150° C. for 15 hr while evaporating ethanol. After cooling, the obtained solid was collected by filtration, washed with ethyl acetate, and dissolved in water. The insoluble material was filtered off, and the filtrate was acidified with 5N hydrochloric acid, and the precipitated solid was collected by filtration. The obtained solid was washed with water and ethyl acetate-hexane to give the title compound (36.4 g, 45%) as a white powder.

$^1$H-NMR (300 MHz, DMSO-$d_6$) δ: 1.12 (3H, t, J=7.6 Hz), 1.26 (3H, t, J=7.1 Hz), 2.42 (2H, q, J=7.6 Hz), 4.25 (2H, q, J=7.0 Hz), 5.79 (1H, s), 11.37 (1H, br s), 12.57 (1H, s).

Reference Example 3

Production of ethyl 4-chloro-6-ethyl-2-oxo-1,2-dihydropyridine-3-carboxylate

A mixture of the compound of Reference Example 2 (15.0 g, 71.0 mmol) and phosphorus oxychloride (19.9 mL, 213 mmol) was stirred at 80° C. for 30 min. The mixture was concentrated under reduced pressure, and ice water was added to the residue. The precipitated solid was collected by filtration, and washed with water and ethyl acetate to give the title compound (9.80 g, 60%) as a white solid.

$^1$H-NMR (300 MHz, DMSO-$d_6$) δ: 1.15 (3H, t, J=7.5 Hz), 1.26 (3H, t, J=7.0 Hz), 2.44-2.55 (2H, m), 4.25 (2H, q, J=7.1 Hz), 6.26 (1H, s), 12.28 (1H, s).

Reference Example 4

Production of ethyl 4-chloro-6-ethyl-2-oxo-1-(2-oxo-2-phenylethyl)-1,2-dihydropyridine-3-carboxylate A mixture of the compound of Reference Example 3 (9.50 g, 41.4 mmol), potassium carbonate (13.7 g, 99.2 mmol), phenacyl bromide (9.88 g, 49.6 mmol) and DMF (100 ml) was stirred at room temperature for 15 hr. The reaction mixture was added to water (100 mL), and the mixture was extracted with ethyl acetate. The extract was washed with brine, dried over magnesium sulfate, and concentrated under reduced pressure. The residue was purified by aminosilica gel chromatography (eluent; ethyl acetate:hexane=1:9→7:3) to give the title compound (1.00 g, 7%) as a white powder.

$^1$H-NMR (300 MHz, DMSO-$d_6$) δ: 1.14 (3H, t, J=7.4 Hz), 1.24 (3H, t, J=7.1 Hz), 2.62 (2H, q, J=7.4 Hz), 4.25 (2H, q, J=7.1 Hz), 5.61 (2H, s), 6.44 (1H, s), 7.54-7.66 (2H, m), 7.70-7.79 (1H, m), 8.05-8.13 (2H, m).

Reference Example 5

Production of ethyl 6-ethyl-3-hydroxy-1-methyl-4-oxo-5-(2-oxo-2-phenylethyl)-4,5-dihydro-1H-pyrrolo[3,2-c]pyridine-2-carboxylate A mixture of the compound of Reference Example 4 (950 mg, 2.73 mmol), ethyl sarcosinate hydrochloride (839 mg, 5.46 mmol), triethylamine (2.27 mL, 16.4 mmol) and ethanol (10 ml) was stirred at 80° C. for 10 hr, triethylamine (2.27 mL, 16.4 mmol) was further added thereto, and the mixture was stirred at 100° C. for 15 hr. After cooling, water was added to the reaction mixture, and the mixture was acidified with 1N hydrochloric acid, and extracted with ethyl acetate. The extract was washed successively with water and brine, dried over magnesium sulfate, and concentrated under reduced pressure. The residue was purified by silica gel chromatography (eluent; ethyl acetate:methanol=10:1) to give the title compound (698 mg, 67%) as a brown solid.

$^1$H-NMR (300 MHz, DMSO-$d_6$) δ: 1.18 (3H, t, J=7.4 Hz), 1.31 (3H, t, J=7.1 Hz), 2.56 (2H, q, J=7.6 Hz), 3.80 (3H, s), 4.30 (2H, q, J=7.2 Hz), 5.55 (2H, s), 6.43 (1H, s), 7.60 (2H, t, J=7.6 Hz), 7.68-7.79 (1H, m), 8.00-8.21 (2H, m), 8.90 (1H, s).

Reference Example 6

Production of ethyl 6-ethyl-1-methyl-4-oxo-5-(2-oxo-2-phenylethyl)-3-{[(trifluoromethyl)sulfonyl]oxy}-4,5-dihydro-1H-pyrrolo[3,2-c]pyridine-2-carboxylate A mixture of the compound of Reference Example 5 (300 mg, 0.784 mmol), trifluoromethanesulfonic anhydride (158 μL, 0.941 mmol) and pyridine (6.0 mL) was stirred at 60° C. for 3 hr under a nitrogen atmosphere. Water (50 mL) was added to the reaction mixture, and the mixture was extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel chromatography (eluate, hexane:ethyl acetate=50:50→0:100) to give the title compound (239 mg, 59%) as a pale-yellow powder. $^1$H NMR (300 MHz, DMSO-$d_6$) δ: 1.20 (3H, t, J=7.3 Hz), 1.33 (3H, t, J=7.2 Hz), 2.60 (2H, q, J=7.3 Hz), 3.95 (3H, s), 4.34 (2H, q, J=7.2 Hz), 5.64 (2H, s), 6.64 (1H, s), 7.57-7.68 (2H, m), 7.70-7.81 (1H, m), 8.07-8.19 (2H, m).

Reference Example 7

Production of ethyl 3-ethenyl-6-ethyl-1-methyl-4-oxo-5-(2-oxo-2-phenylethyl)-4,5-dihydro-1H-pyrrolo[3,2-c]pyridine-2-carboxylate A mixture of the compound of Reference Example 6 (218 mg, 0.424 mmol), tributylvinyltin (328 μL, 1.28 mmol) and Pd(PPh$_3$)$_4$ (148 mg, 0.128 mmol) was stirred at 100° C. for 3 hr under an argon atmosphere. Water (50 mL) was added to the reaction mixture, and the mixture was extracted with ethyl acetate (100 ml). The extract was washed with brine (50 mL), and dried over anhydrous sodium sulfate. The insoluble material was removed by filtration, and the filtrate was concentrated under reduced pressure. The precipitate was collected by filtration, and washed with diisopropyl ether to give the title compound (120 mg, 72%) as a gray solid.

$^1$H NMR (300 MHz, DMSO-$d_6$) δ: 1.20 (3H, t, J=7.3 Hz), 1.33 (3
H, t, J=7.1 Hz), 2.61 (2H, q, J=7.3 Hz), 3.85 (3H, s), 4.33 (2H, q, J=7.1 Hz), 5.29-5.43 (1H, m), 5.59 (2H, s), 6.41-6.59 (2H, m), 7.23 (1H, dd, J=17.7, 11.8 Hz), 7.55-7.67 (2H, m), 7.68-7.81 (1H, m), 8.01-8.20 (2H, m).

Reference Example 8

Production of ethyl 3,6-diethyl-5-(2-hydroxy-2-phenylethyl)-1-methyl-4-oxo-4,5-dihydro-1H-pyrrolo[3,2-c]pyridine-2-carboxylate A mixture of the compound of Reference Example 7 (113 mg, 0.288 mmol), 10% palladium on carbon (56.5 mg) and methanol (3.4 ml) was stirred at room temperature for 2 hr under a hydrogen atmosphere. The insoluble material was removed by filtration, and the filtrate was concentrated under reduced pressure. The precipitate was collected by filtration, and washed with diisopropyl ether to give the title compound (41.2 mg, 36%) as a white solid.

$^1$H NMR (300 MHz, DMSO-$d_6$) δ: 1.11-1.23 (6H, m), 1.34 (3H, t, J=7.1 Hz), 2.75-2.88 (2H, m), 3.16-3.26 (2H, m), 3.79-3.91 (4H, m), 4.16-4.25 (1H, m), 4.30 (2H, q, J=7.1 Hz), 4.87-4.99 (1H, m), 5.56 (1H, d, J=4.2 Hz), 6.38 (1H, s), 7.22-7.49 (5H, m).

Reference Example 9

Production of ethyl 3,6-diethyl-1-methyl-4-oxo-5-(2-oxo-2-phenylethyl)-4,5-dihydro-1H-pyrrolo[3,2-c]pyridine-2-carboxylate A mixture of the compound of Reference Example 8 (66.1 mg, 0.167 mmol), 4-methylmorpholine N-oxide (39.1 mg, 0.941 mmol), tetrapropylammonium perruthenate (11.7 mg, 33.4 μmol) and MeCN (2.0 mL) was stirred at room temperature for 1 hr. The reaction mixture was concentrated, and the residue was purified by silica gel chromatography (eluate, hexane:ethyl acetate=50:500:100) to give the title compound (66.2 mg, 100%) as a white powder.

$^1$H NMR (300 MHz, DMSO-$d_6$) δ: 1.08 (3H, t, J=7.0 Hz), 1.19 (3H, t, J=7.0 Hz), 1.33 (3H, t, J=7.1 Hz), 2.58 (2H, q, J=7.0 Hz), 3.12 (2H, q, J=7.0 Hz), 3.87 (3H, s), 4.30 (2H, q, J=7.1 Hz), 5.58 (2H, s), 6.48 (1H, s), 7.56-7.66 (2H, m), 7.69-7.78 (1H, m), 8.06-8.18 (2H, m).

Reference Example 10

Production of 3,6-diethyl-1-methyl-4-oxo-5-(2-oxo-2-phenylethyl)-4,5-dihydro-1H-pyrrolo[3,2-c]pyridine-2-carboxylic acid A mixture of the compound of Reference Example 9 (66.2 mg, 0.168 mmol), 8N aqueous sodium hydroxide solution (0.199 mL) and ethanol (2.0 mL) was stirred at 70° C. for 3 hr. The reaction mixture was concentrated under reduced pressure, and 1N hydrochloric acid (20 mL) was added to the residue, and the mixture was extracted with ethyl acetate (50 mL). The extract was washed with brine (20 mL), and dried over anhydrous sodium sulfate. The insoluble material was removed by filtration, and the filtrate was concentrated under reduced pressure to give the title compound (61.0 mg, 99%) as a white solid.

$^1$H NMR (300 MHz, DMSO-$d_6$) δ: 1.07 (3H, t, J=7.3 Hz), 1.19 (3H, t, J=7.4 Hz), 2.57 (2H, q, J=7.4 Hz), 3.11 (2H, q, J=7.3 Hz), 3.87 (3H, s), 5.58 (2H, s), 6.46 (1H, s), 7.56-7.66 (2H, m), 7.68-7.78 (1H, m), 8.05-8.17 (2H, m), 12.80 (1H, br s).

Reference Example 11

Production of 3-ethenyl-6-ethyl-1-methyl-4-oxo-5-(2-oxo-2-phenylethyl)-4,5-dihydro-1H-pyrrolo[3,2-c]pyridine-2-carboxylic acid By a method similar to that in Reference Example 10, the title compound (118 g, 100%) was obtained as a brown powder from the compound of Reference Example 7 (120 mg, 0.306 mmol), 8N aqueous sodium hydroxide solution (0.240 mL), and ethanol (1.6 ml).

$^1$H NMR (300 MHz, DMSO-$d_6$) δ: 1.20 (3H, t, J=7.3 Hz), 2.60 (2 H, q, J=7.3 Hz), 3.86 (3H, s), 5.26-5.40 (1H, m), 5.59 (2H, s), 6.45-6.64 (2H, m), 7.30 (1H, dd, J=17.8, 11.9 Hz), 7.56-7.67 (2H, m), 7.68-7.78 (1H, m), 8.03-8.18 (2H, m), 13.10 (1H, br s).

Reference Example 12

Production of ethyl 6-ethyl-1-methyl-4-oxo-5-(2-oxo-2-phenylethyl)-3-(2,2,2-trifluoroethoxy)-4,5-dihydro-1H-pyrrolo[3,2-c]pyridine-2-carboxylate A mixture of the compound of Reference Example 5 (1.00 g, 2.61 mmol), 1,1,1-trifluoro-2-iodoethane (1.29 mL, 13.1 mmol), cesium carbonate (4.27 g, 13.1 mmol) and dimethyl sulfoxide (10 mL) was stirred at 100° C. for 5 hr. The reaction mixture was filtered, and the filtrate was diluted with 1N hydrochloric acid (30 mL), and the mixture was extracted with ethyl acetate. The extract was washed with water and brine, dried over magnesium sulfate, and concentrated under reduced pressure. The residue was purified by aminosilica gel chromatography (eluent; hexane:ethyl acetate=90:10-0:100) to give the title compound (278 mg, 23%) as a white solid.

$^1$H-NMR (300 MHz, DMSO-$d_6$) δ: 1.19 (3H, t, J=7.4 Hz), 1.28 (3H, t, J=7.1 Hz), 2.59 (2H, q, J=7.4 Hz), 3.86 (3H, s), 4.26 (2H, q, J=7.1 Hz), 4.83 (2H, q, J=9.3 Hz), 5.62 (2H, s), 6.56 (1H, s), 7.61 (2H, t, J=7.5 Hz), 7.70-7.78 (1H, m), 8.08-8.14 (2H, m).

Reference Example 13

Production of 6-ethyl-1-methyl-4-oxo-5-(2-oxo-2-phenylethyl)-3-(2,2,2-trifluoroethoxy)-4,5-dihydro-1H-pyrrolo[3,2-c]pyridine-2-carboxylic acid A solution of the compound of Reference Example 12 (270 mg, 0.581 mmol) and 8N aqueous sodium hydroxide solution (1 mL) in ethanol (7 mL) was stirred at 60° C. for 1 hr. The reaction mixture was diluted with water, and acidified with 5N hydrochloric acid, and the precipitated solid was collected by filtration. The obtained solid was washed with water, and dried under reduced pressure to give the title compound (235 mg, 93%) as a white powder.

$^1$H-NMR (300 MHz, DMSO-$d_6$) δ: 1.19 (3H, t, J=7.4 Hz), 2.58 (2H, q, J=7.4 Hz), 3.86 (3H, s), 4.82 (2H, q, J=9.2 Hz), 5.61 (2H, s), 6.54 (1H, s), 7.61 (2H, t, J=7.6 Hz), 7.70-7.77 (1H, m), 8.07-8.16 (2H, m), 12.74 (1H, br s).

Reference Example 14

Production of 6-ethyl-N-[1-(hydroxyacetyl)piperidin-4-yl]-1-methyl-4-oxo-5-(2-oxo-2-phenylethyl)-3-(2,2,2-s trifluoroethoxy)-4,5-dihydro-1H-pyrrolo[3,2-c]pyridine-2-carboxamide To a solution of the compound of Reference Example 13 (230 mg, 0.527 mmol), 2-(4-aminopiperidin-1-yl)-2-oxoethanol hydrochloride (133 mg, 0.685 mmol), HOBt (107 mg, 0.791 mmol) and triethylamine (95.0 μL, 0.685 mmol) in DMF (4 mL) was added WSCD (152 mg, 0.791 mmol) under ice-cooling, and the mixture was stirred at room temperature for 15 hr. The reaction mixture was diluted with water, and extracted twice with ethyl acetate. The extracts were combined, washed with water and brine, dried over magnesium sulfate, and concentrated under reduced pressure. The residue was purified by aminosilica gel chromatography (eluent; ethyl acetate:hexane=1:3→100:0), and the obtained solid was recrystallized from ethyl acetate-hexane to give the title compound (146 mg, 48%) as a white powder.
$^1$H NMR (300 MHz, DMSO-$d_6$) δ: 1.13-1.49 (5H, m), 1.82-1.94 (2H, m), 2.59 (2H, q, J=7.2 Hz), 2.76-2.88 (1H, m), 3.02-3.15 (1H, m), 3.64-3.75 (1H, m), 3.86 (3H, s), 3.96-4.16 (3H, m), 4.20-4.33 (1H, m), 4.53 (1H, t, J=5.4 Hz), 5.05 (2H, q, J=9.3 Hz), 5.63 (2H, s), 6.54 (1H, s), 7.51 (1H, d, J=7.7 Hz), 7.61 (2H, t, J=7.6 Hz), 7.70-7.78 (1H, m), 8.08-8.14 (2H, m).

Reference Example 15

Production of 6-ethyl-N-[1-(hydroxyacetyl)piperidin-4-yl]-5-(2-hydroxy-2-phenylethyl)-1-methyl-4-oxo-3-(2,2,2-trifluoroethoxy)-4,5-dihydro-1H-pyrrolo[3,2-c]pyridine-2-carboxamide To a solution of the compound of Reference Example 14 (100 mg, 0.173 mmol) in a mixed solvent of THF (6 mL)-ethanol (2 mL) was added sodium borohydride (15 mg, 0.396 mmol) under ice-cooling, and the mixture was stirred at room temperature for 5 hr. The reaction mixture was poured into water, and the mixture was extracted with ethyl acetate. The extract was washed with water and brine, and dried over magnesium sulfate, and the solvent was evaporated under reduced pressure. The obtained solid was recrystallized from acetone-hexane to give the title compound (51 mg, 51%) as white crystals.
$^1$H NMR (300 MHz, DMSO-$d_6$) δ: 1.18 (3H, t, J=7.2 Hz), 1.20-1.55% (2H, m), 1.81-1.97 (2H, m), 2.68-2.95 (3H, m), 3.01-3.20 (1H, m), 3.70 (1H, br d, J=13.2 Hz), 3.83 (3H, s), 3.85-4.15 (4H, m), 4.18-4.35 (2H, m), 4.50 (1H, t, J=5.4 Hz), 4.89-5.00 (1H, m), 5.13 (2H, q, J=8.7 Hz), 5.56 (1H, d, J=4.5 Hz), 6.42 (1H, s), 7.20-7.51 (6H, m).

Reference Example 16

Production of ethyl 6-ethyl-1-methyl-4-oxo-5-(2-oxo-2-phenylethyl)-4,5-dihydro-1H-pyrrolo[3,2-c]pyridine-2-carboxylate A mixture of the compound of Reference Example 6 (3.70 g, 7.19 mmol), tributylphosphine (146 mg, 0.72 mmol), palladium acetate (161 mg, 0.72 mmol), formic acid (993 mg, 21.58 mmol) and triethylamine (2.18 g, 21.58 mmol) in DMF (50 mL) was refluxed for 4 hr under an argon atmosphere. Tributylphosphine (1.31 g, 6.45 mmol) and palladium acetate (1.45 g, 6.45 mmol) were added to the reaction mixture, and the mixture was further refluxed for 4 hr under an argon atmosphere. The reaction mixture was cooled to room temperature, and diluted with water and ethyl acetate. The insoluble material was removed by filtration, and the organic phase was washed with brine, dried over magnesium sulfate, and concentrated under reduced pressure. The residue was purified by silica gel chromatography (eluate, hexane/ethyl acetate=1/1) to give the title compound (1.10 g, 42%) as a pale-pink powder.
$^1$H NMR (300 MHz, DMSO-$d_6$) δ: 1.20 (3H, t, J=7.4 Hz), 1.31 (3H, t, J=7.1 Hz), 2.59 (2H, q, J=7.3 Hz), 3.96 (3H, s), 4.28 (2H, q, J=7.2 Hz), 5.63 (2H, s), 6.57 (1H, s), 7.22 (1H, s), 7.61 (2H, t, J=7.7 Hz), 7.74 (1H, t, J=7.4 Hz), 8.09-8.12 (2H, m).

Reference Example 17

Production of 6-ethyl-1-methyl-4-oxo-5-(2-oxo-2-phenylethyl)-4,5-dihydro-1H-pyrrolo[3,2-c]pyridine-2-carboxylic acid A mixture of the compound of Reference Example 16 (147 mg, 0.40 mmol), 1N aqueous sodium hydroxide solution (1.2 mL) and ethanol (4 mL)-THF (1 mL) was stirred at 60° C. for 1.5 hr. 1N Hydrochloric acid (2 mL) was added to the reaction mixture, the mixture was further diluted with water, and the obtained solid was collected by filtration. The solid was washed with water, and dried under reduced pressure to give the title compound (131 mg, 97%) as a gray powder.
$^1$H NMR (300 MHz, DMSO-$d_6$) δ: 1.20 (3H, t, J=7.4 Hz), 2.59 (2H, q, J=7.4 Hz), 3.96 (3H, s), 5.62 (2H, s), 6.55 (1H, s), 7.17 (1H, s), 7.56-7.66 (2H, m), 7.68-7.78 (1H, m), 8.07-8.15 (2H, m), 12.76 (1H, s).

Reference Example 18

Production of 6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide A mixture of the compound of Reference Example 17 (131 mg, 0.39 mmol), 2-(4-aminopiperidin-1-yl)-2-oxoethanol hydrochloride (117 mg, 0.60 mmol), HOBt (81 mg, 0.60 mmol), WSCD (115 mg, 0.60 mmol) and triethylamine (0.112 ml, 0.80 mmol) in DMF (3 mL) was stirred at room temperature for 3 days. The reaction mixture was partitioned between water and ethyl acetate, the organic phase was washed with brine, dried over magnesium sulfate, and concentrated under reduced pressure. The residue was purified by aminosilica gel column chromatography (eluate, ethyl acetate/methanol=100/0→80/20), then silica gel chromatography (eluate, ethyl acetate/methanol=100/0→85/15) to give the title compound (239 mg, 59%) as a pale-yellow powder.
$^1$H NMR (300 MHz, DMSO-$d_6$) δ: 1.19 (3H, t, J=7.4 Hz), 1.30-1.56 (2H, m), 1.75-1.91 (2H, m), 2.58 (2H, q, J=7.4 Hz), 2.69-2.86 (1H, m), 2.98-3.14 (1H, m), 3.62-3.78 (1H, m), 3.94 (3H, s), 3.93-4.20 (3H, m), 4.23-4.38 (1H, m), 4.51 (1H, t, J=5.4 Hz), 5.63 (2H, s), 6.51 (1H, s), 7.30 (1H, s), 7.56-7.65 (2H, m), 7.69-7.78 (1H, m), 8.07-8.15 (2H, m), 8.21 (1H, d, J=7.9 Hz).

Reference Example 19

Production of benzyl 6-ethyl-3-hydroxy-1-methyl-4-oxo-5-(2-oxo-2-phenylethyl)-4,5-dihydro-1H-pyrrolo[3,2-c]pyridine-2-carboxylate A mixture of the compound of Reference Example 4 (5.00 g, 14.98 mmol), benzyl sarcosinate hydrochloride (6.46 g, 29.96 mmol) and triethylamine (15.15 g, 0.15 mol) in DME (80 mL) was heated under reflux for 24 hr. DBU (2.28 g, 14.98 mmol) was added thereto, and the mixture was further heated under reflux for 24 hr. After cooling, the reaction mixture was concentrated under reduced pressure, and the residue was partitioned between 1N hydrochloric acid and ethyl acetate-THF. The organic layer was purified by silica gel column chromatography (eluate, hexane/ethyl acetate=1/1), and the obtained solid was washed with diisopropyl ether and dried under reduced pressure to give the title compound (3.41 g, 51%) as a beige solid.
$^1$H NMR (300 MHz, DMSO-$d_6$) δ: 1.18 (3H, t, J=7.4 Hz), 2.56 (2H, q, J=7.2 Hz), 3.79 (3H, s), 5.34 (2H, s), 5.56 (2H, s), 6.43 (1H, s), 7.33-7.42 (3H, m), 7.47 (2H, dd, J=8.4, 1.8 Hz), 7.60 (2H, t, J=7.5 Hz), 7.73 (1H, t, J=7.5 Hz), 8.09-8.12 (2H, m), 9.01 (1H, s).

Reference Example 20

Production of benzyl 6-ethyl-1-methyl-4-oxo-5-(2-oxo-2-phenylethyl)-3-{[(trifluoromethyl)sulfonyl]oxy}-4,5-dihydro-1H-pyrrolo[3,2-c]pyridine-2-carboxylate To a solution of the compound of Reference Example 19 (3.0 g, 6.75 mmol) in pyridine (50 mL) was added trifluoromethanesulfonic anhydride (1.59 mL, 9.45 mmol), and the mixture was stirred at 60° C. for 3 hr. The reaction mixture was diluted with water (250 mL), and the mixture was extracted with ethyl acetate. The extract was washed with brine, dried over anhydrous magnesium sulfate, and concentrated under reduced pressure. The residue was purified by silica gel column chromatography (eluate, hexane/ethyl acetate=1/2), and the obtained solid was washed with diisopropyl ether and dried under reduced pressure to give the title compound (2.54 g, 66%) as a pale-yellow solid.

$^1$H NMR (300 MHz, DMSO-$d_6$) δ: 1.19 (3H, t, J=7.3 Hz), 2.59 (2H, q, J=7.3 Hz), 3.95 (3H, s), 5.38 (2H, s), 5.64 (2H, s), 6.64 (1H, s), 7.36-7.48 (5H, m), 7.61 (2H, t, J=7.7 Hz), 7.74 (1H, t, J=7.5 Hz), 8.10-8.13 (2H, m).

Reference Example 21

Production of benzyl 3-[(diphenylmethylidene)amino]-6-ethyl-1-methyl-4-oxo-5-(2-oxo-2-phenylethyl)-4,5-dihydro-1H-pyrrolo[3,2-c]pyridine-2-carboxylate To a mixture of the compound of Reference Example 20 (500 mg, 0.87 mmol), benzophenonimine (210 μL), cesium carbonate (565 mg, 1.73 mmol) and toluene (10 mL) were added Pd$_2$dba$_3$ (40 mg, 0.04 mmol) and Xantphos (50 mg, 0.08 mmol), and the mixture was stirred at 100° C. for 18 hr under an argon atmosphere. After cooling, the mixture was filtered through Celite, and washed with ethyl acetate. The filtrate was washed with water and brine, dried over anhydrous magnesium sulfate, and concentrated under reduced pressure. The residue was purified by silica gel column chromatography (eluate, hexane/ethyl acetate=1/1), and the obtained solid was washed with diisopropyl ether and dried under reduced pressure to give the title compound (299 mg, 57%) as a yellow powder.

$^1$H NMR (300 MHz, DMSO-$d_6$) δ: 1.17 (3H, t, J=7.1 Hz), 2.44-2.50 (2H, m), 3.79 (3H, s), 5.21 (2H, s), 5.51 (2H, d, J=5.7 Hz), 6.37 (1H, s), 6.85-7.00 (2H, br), 7.06 (2H, t, J=7.5 Hz), 7.16-7.60 (13H, m), 7.70 (1H, t, J=7.5 Hz), 8.06-8.09 (2H, m).

Reference Example 22

Production of benzyl 3-amino-6-ethyl-1-methyl-4-oxo-5-(2-oxo-2-phenylethyl)-4,5-dihydro-1H-pyrrolo[3,2-c]pyridine-2-carboxylate A mixture of the compound of Reference Example 21 (280 mg, 0.46 mmol) and 2N hydrochloric acid (1 mL) in THF (4 mL) was stirred at room temperature for 1 hr. To the mixture was added aqueous sodium hydrogen carbonate solution, and the mixture was extracted with ethyl acetate. The extract was washed with brine, dried over anhydrous magnesium sulfate, and concentrated under reduced pressure. The obtained solid was washed with diisopropyl ether and dried under reduced pressure to give the title compound (177 mg, 87%) as a beige powder.

$^1$H NMR (300 MHz, DMSO-$d_6$) δ: 1.17 (3H, t, J=7.4 Hz), 2.50-2.58 (2H, m), 3.75 (3H, s), 5.30 (2H, s), 5.55 (2H, s), 5.85 (2H, br s), 6.37 (1H, s), 7.33-7.47 (5H, m), 7.60 (2H, t, J=7.5 Hz), 7.73 (1H, t, J=7.5 Hz), 8.09-8.11 (2H, m).

Reference Example 23

Production of benzyl 6-ethyl-1-methyl-4-oxo-5-(2-oxo-2-phenylethyl)-3-[(trifluoroacetyl)amino]-4,5-dihydro-1H-pyrrolo[3,2-c]pyridine-2-carboxylate A mixture of the compound of Reference Example 22 (170 mg, 0.38 mmol) and trifluoroacetic anhydride (121 mg, 0.57 mmol) in pyridine (3 mL) was stirred at room temperature for 1 hr. Water was added to the reaction mixture, and the mixture was extracted with ethyl acetate. The extract was washed with brine, dried over anhydrous magnesium sulfate, and concentrated under reduced pressure. The obtained solid was washed with diisopropyl ether, and dried under reduced pressure to give the title compound (185 mg, 90%) as a white solid.

$^1$H NMR (300 MHz, DMSO-$d_6$) δ: 1.20 (3H, t, J=7.5 Hz), 2.58 (2H, q, J=7.5 Hz), 3.94 (3H, s), 5.27 (2H, s), 5.59 (2H, s), 6.57 (1H, s), 7.32-7.43 (5H, m), 7.60 (2H, t, J=7.5 Hz), 7.70 (1H, t, J=7.5 Hz), 8.09-8.12 (2H, m), 10.97 (1H, s).

Reference Example 24

Production of benzyl 6-ethyl-3-[ethyl(trifluoroacetyl)amino]-1-methyl-4-oxo-5-(2-oxo-2-phenylethyl)-4,5-dihydro-1H-pyrrolo[3,2-c]pyridine-2-carboxylate A mixture of the compound of Reference Example 23 (160 mg, 0.30 mmol), iodoethane (231 mg, 1.48 mmol) and potassium carbonate (82 mg, 0.60 mmol) in DMF (2 mL) was stirred at room temperature for 18 hr. Saturated aqueous sodium hydrogen carbonate was added to the reaction mixture, and the mixture was extracted with ethyl acetate. The extract was washed with brine, dried over anhydrous magnesium sulfate, and concentrated under reduced pressure. The residue was purified by silica gel column chromatography (eluate, ethyl acetate/hexane=1/1) to give the title compound (170 mg, 100%) as a colorless oil.

$^1$H NMR (300 MHz, CDCl$_3$) δ: 0.97 (3H, t, J=7.4 Hz), 1.23-1.32 (3H, m), 2.53 (2H, q, J=7.4 Hz), 3.59-3.70 (1H, m), 3.77-3.86 (1H, m), 3.99 (3H, s), 5.16-5.39 (3H, m), 5.77 (0.8H, d, J=17.7 Hz), 5.95 (0.2H, d, J=17.7 Hz), 6.26 (1H, s), 7.34-7.39 (5H, m), 7.50 (2H, t, J=7.5 Hz), 7.59-7.65 (1H, m), 8.01-8.04 (2H, m).

Reference Example 25

Production of 6-ethyl-3-[ethyl(trifluoroacetyl)amino]-1-methyl-4-oxo-5-(2-oxo-2-phenylethyl)-4,5-dihydro-1H-pyrrolo[3,2-c]pyridine-2-carboxylic acid A mixture of the compound of Reference Example 24 (80 mg, 0.14 mmol) and 5% palladium on carbon (10 mg) in ethyl acetate (3 mL) was stirred at room temperature for 1 hr under a hydrogen atmosphere. Methanol (0.5 mL) was added thereto, and the mixture was further stirred under a hydrogen atmosphere at room temperature for 18 hr. The catalyst was filtered off, and the filtrate was concentrated to give the title compound (50 mg, 75%) as a pale-yellow oil.

$^1$H NMR (300 MHz, CDCl$_3$) δ: 1.07 (3H, br s), 1.23-1.30 (3H, m), 2.52 (2H, br d, J=7.2 Hz), 3.70-3.99 (5H, m), 5.43 (1H, d, J=17.7 Hz), 5.79 (1H, d, J=17.7 Hz), 6.31 (1H, s), 7.38-7.63 (3H, m), 8.03 (2H, d, J=7.5 Hz).

Reference Example 26

Production of ethyl 3-cyano-6-ethyl-1-methyl-4-oxo-5-(2-oxo-2-phenylethyl)-4,5-dihydro-1H-pyrrolo[3,2-c]pyridine-2-carboxylate A mixture of the compound of Reference Example 6 (100 mg, 0.19 mmol), zinc(II) cyanide (222 mg, 1.90 mmol) and tetrakis(triphenylphosphine)palladium(0) (22 mg, 0.019 mmol) in DMF (3 mL) was stirred at 150° C. for 1 hr under microwave irradiation. After cooling, the reaction mixture was filtered through Celite, and the filtrate was washed successively with saturated aqueous sodium hydrogen carbonate and brine, dried over anhydrous magnesium sulfate, and concentrated under reduced pressure. The residue was purified by silica gel column chromatography (eluate, ethyl acetate/hexane=1/1-2/1) to give the title compound (20 mg, 27%) as a white solid.

$^1$H NMR (300 MHz, DMSO-$d_6$) δ: 1.33 (3H, t, J=7.4 Hz), 1.49 (3H, t, J=7.2 Hz), 2.60 (2H, q, J=7.4 Hz), 4.04 (3H, s), 4.47 (2H, q, J=7.2 Hz), 5.62 (2H, s), 6.29 (1H, s), 7.51-7.56 (2H, m), 7.63-7.66 (1H, m), 8.05-8.09 (2H, m).

Reference Example 27

Production of 3-cyano-6-ethyl-1-methyl-4-oxo-5-(2-oxo-2-phenylethyl)-4,5-dihydro-1H-pyrrolo[3,2-c]pyridine-2-carboxylic acid A mixture of the compound of Reference Example 26 (26 mg, 0.066 mmol) and 2N aqueous sodium hydroxide solution (1 mL) in ethanol (2 mL) was stirred at room temperature for 1 hr. The reaction mixture was neutralized with 1N hydrochloric acid (2 mL), and further diluted with water (10 mL). The precipitate was collected by filtration, washed with water, and dried under reduced pressure to give the title compound (19 mg, 79%) as a beige powder.

$^1$H NMR (300 MHz, DMSO-$d_6$) δ: 1.20 (3H, t, J=7.2 Hz), 2.63 (2H, q, J=7.2 Hz), 4.00 (3H, s), 5.65 (2H, s), 6.66 (1H, s), 7.62 (2H, t, J=7.5 Hz), 7.75 (1H, t, J=7.5 Hz), 8.11-8.14 (2H, m).

Example 1

Production of 3,6-diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

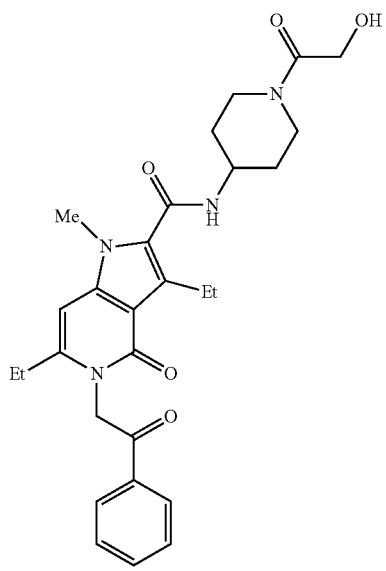 [SMILES: CCc1c(C(=O)NC2CCN(C(=O)CO)CC2)n(C)c2cc(CC)n(CC(=O)c3ccccc3)c(=O)c12]

A mixture of the compound of Reference Example 10 (61.0 mg, 0.166 mmol), 2-(4-aminopiperidin-1-yl)-2-oxoethanol hydrochloride (38.9 mg, 0.200 mmol), HOBt (44.9 mg, 0.332 mmol), WSCD (63.6 mg, 0.332 mmol), triethylamine (92.0 μL, 0.664 mmol) and DMF (1.8 mL) was stirred at room temperature for 20 hr. The reaction mixture was diluted with water, and extracted twice with ethyl acetate. The extracts were combined, washed with water and brine, dried over sodium sulfate, and concentrated under reduced pressure. The residue was purified by aminosilica gel chromatography (eluent; ethyl acetate), and the obtained solid was recrystallized from ethyl acetate to give the title compound (39.2 mg, 47%) as a white powder.

$^1$H NMR (300 MHz, DMSO-$d_6$) δ: 1.06 (3H, t, J=7.2 Hz), 1.18 (3H, t, J=7.3 Hz), 1.30-1.54 (2H, m), 1.81-1.93 (2H, m), 2.54-2.63 (2H, m), 2.78-2.92 (3H, m), 3.01-3.17 (1H, m), 3.59-3.73 (4H, m), 3.99-4.16 (3H, m), 4.20-4.31 (1H, m), 4.51 (1H, t, J=5.5 Hz), 5.58 (2H, s), 6.42 (1H, s), 7.56-7.65 (2H, m), 7.69-7.77 (1H, m), 8.07-8.15 (2H, m), 8.21 (1H, d, J=7.4 Hz).

Example 2

Production of 3-ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

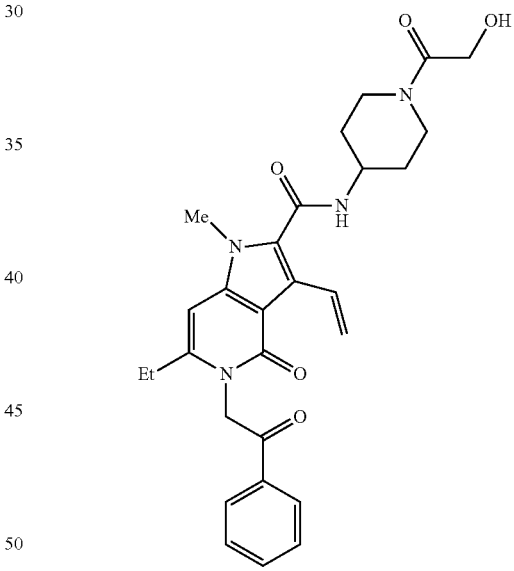

By a method similar to that in Example 1, the title compound (51.0 mg, 31%) was obtained as a white powder from the compound of Reference Example 11 (118 mg, 0.324 mmol), 2-(4-aminopiperidin-1-yl)-2-oxoethanol hydrochloride (81.9 mg, 0.421 mmol), HOBt (65.7 mg, 0.486 mmol), WSCD (93.2 mg, 0.486 mmol), triethylamine (89.7 μL, 0.648 mmol) and DMF (2.4 mL). $^1$H NMR (300 MHz, DMSO-$d_6$) δ: 1.19 (3H, t, J=7.3 Hz), 1.27-1.53 (2H, m), 1.77-1.95 (2H, m), 2.54-2.65 (2H, m), 2.77-2.93 (1H, m), 3.02-3.19 (1H, m), 3.57-3.77 (4H, m), 3.96-4.16 (3H, m), 4.19-4.31 (1H, m), 4.44-4.58 (1H, m), 5.16 (1H, s), 5.60 (2H, s), 5.96-6.12 (1H, m), 6.47 (1H, s), 6.97 (1H, dd, J=17.8, 11.5 Hz), 7.52-7.67 (2H, m), 7.68-7.80 (1H, m), 8.04-8.18 (2H, m), 8.62 (1H, d, J=7.6 Hz).

Example 3

Production of N-[2-(diethylamino)ethyl]-3,6-diethyl-1-methyl-4-oxo-5-(2-oxo-2-phenylethyl)-4,5-dihydro-1H-pyrrolo[3,2-c]pyridine-2-carboxamide

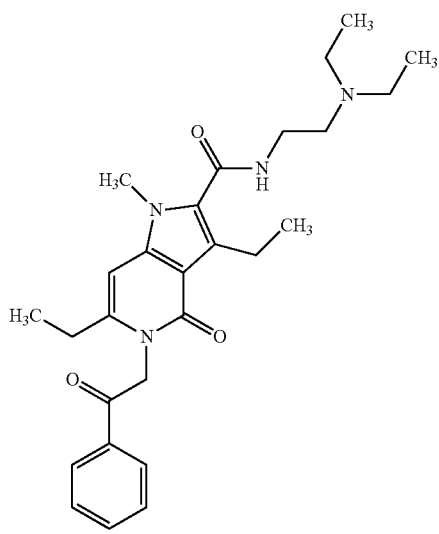 [SMILES: CCc1c(C(=O)NCCN(CC)CC)n(C)c2cc(CC)n(CC(=O)c3ccccc3)c(=O)c12]

To a 0.19M DMF solution (500 μL, 96 μmol) of N,N-diethylethylenediamine was added a 0.16M DMF solution (500 μL, 80 μmol) of the compound of Reference Example 10, and a DMF solution (500 μL) of HOBt (120 μmol) and WSCD HCl (120 μmol) was added thereto. The reaction mixture was stirred at room temperature overnight and extracted with ethyl acetate (3 mL) and 2% aqueous sodium hydrogen carbonate solution (2 mL). The organic layer was collected by upper layer PhaseSeptube (manufactured by Wako Pure Chemical Industries, Ltd.). Ethyl acetate was evaporated by blowing nitrogen against it, and the residue was dissolved in DMSO:acetonitrile (1:4) (1000 μL), and the solution was purified by preparative HPLC (acetonitrile-10 mM ammonium carbonate-containing water) to give the title compound.

yield: 22.5 mg

LC-MS analysis: purity 98%

MS (ESI+): 465.3 (M+H)

Example 4-Example 30

By a method similar to that in Example 3, the compounds shown in Table 1 were obtained from the compound of Reference Example 10 and the corresponding amine.

TABLE 1

| Ex. No. | structure | yield (mg) | purity (%) | MS (ESI+) |
|---|---|---|---|---|
| 4 | 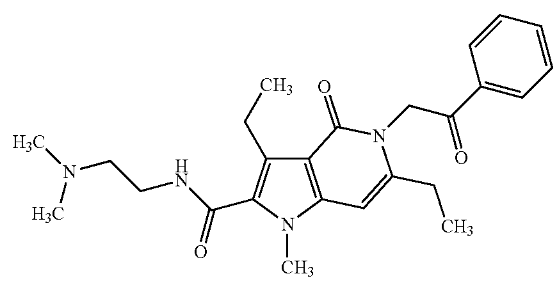 [SMILES: CCc1c(C(=O)NCCN(C)C)n(C)c2cc(CC)n(CC(=O)c3ccccc3)c(=O)c12] | 17.8 | 98 | 437.3 |
| 5 | 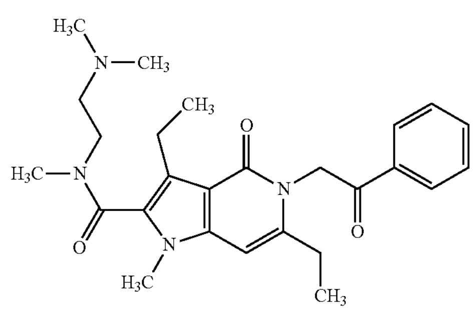 [SMILES: CCc1c(C(=O)N(C)CCN(C)C)n(C)c2cc(CC)n(CC(=O)c3ccccc3)c(=O)c12] | 22.8 | 96 | 451.3 |
| 6 | 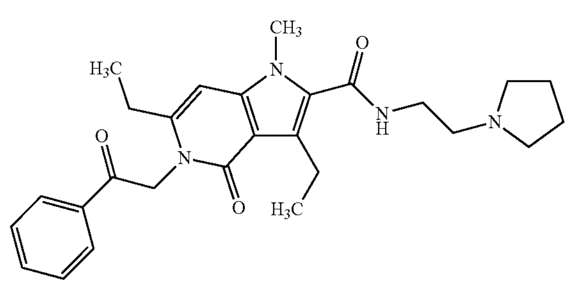 [SMILES: CCc1c(C(=O)NCCN2CCCC2)n(C)c2cc(CC)n(CC(=O)c3ccccc3)c(=O)c12] | 24.3 | 100 | 463.3 |

TABLE 1-continued
| Ex. No. | structure | yield (mg) | purity (%) | MS (ESI+) |
|---|---|---|---|---|
| 7 | 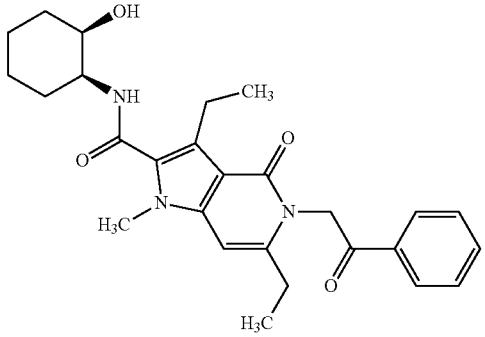 [SMILES: CCc1c(C(=O)N[C@H]2CCCC[C@H]2O)n(C)c2cc(CC)n(CC(=O)c3ccccc3)c(=O)c12] | 21.8 | 100 | 464.2 |
| 8 | 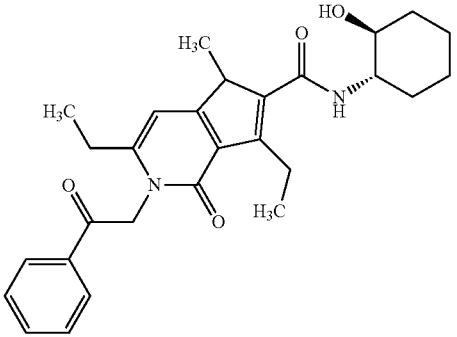 [SMILES: CCC1=C(C(=O)N[C@H]2CCCC[C@@H]2O)C(C)c2cc(CC)n(CC(=O)c3ccccc3)c(=O)c21] | 24.4 | 90 | 464.2 |
| 9 | 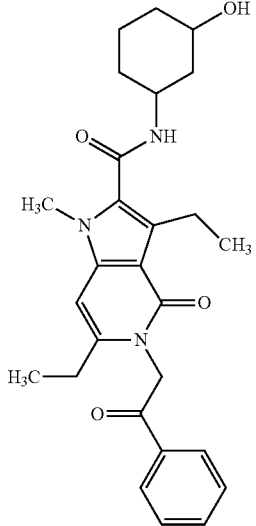 [SMILES: CCc1c(C(=O)NC2CCCC(O)C2)n(C)c2cc(CC)n(CC(=O)c3ccccc3)c(=O)c12] | 20.6 | 100 | 464.3 |

TABLE 1-continued
| Ex. No. | structure | yield (mg) | purity (%) | MS (ESI+) |
|---|---|---|---|---|
| 10 | 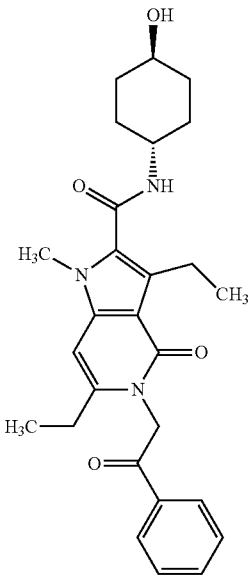 [SMILES: CCc1c(C(=O)N[C@H]2CC[C@H](O)CC2)n(C)c2cc(CC)n(CC(=O)c3ccccc3)c(=O)c12] | 11.8 | 100 | 464.2 |
| 11 | 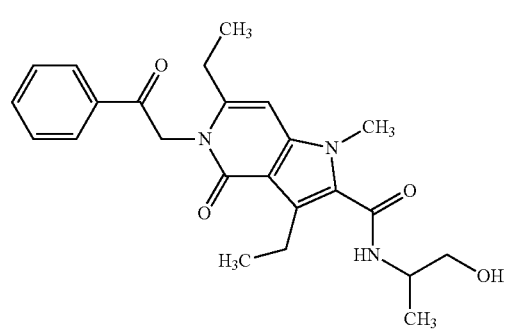 [SMILES: CCc1c(C(=O)NC(C)CO)n(C)c2cc(CC)n(CC(=O)c3ccccc3)c(=O)c12] | 24.1 | 100 | 424.2 |
| 12 | 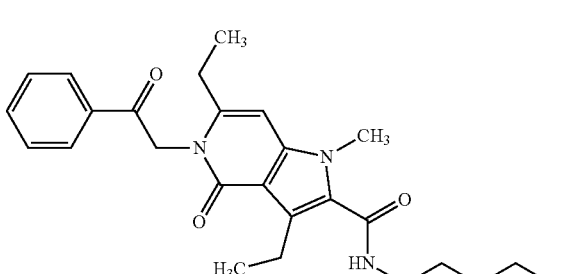 | 20.4 | 85 | 438.2 |

TABLE 1-continued

| Ex. No. | structure | yield (mg) | purity (%) | MS (ESI+) |
| --- | --- | --- | --- | --- |
| 13 | 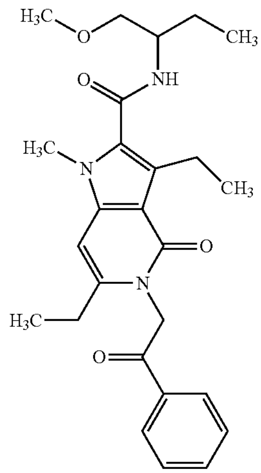 [SMILES: CCc1c(C(=O)NC(CC)COC)n(C)c2cc(CC)n(CC(=O)c3ccccc3)c(=O)c12] | 24.9 | 100 | 452.2 |
| 14 | 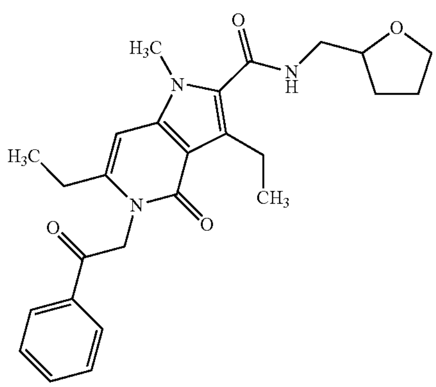 [SMILES: CCc1c(C(=O)NCC2CCCO2)n(C)c2cc(CC)n(CC(=O)c3ccccc3)c(=O)c12] | 26.6 | 100 | 450.2 |
| 15 | 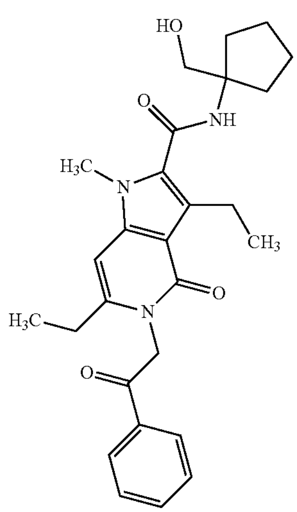 [SMILES: CCc1c(C(=O)NC2(CO)CCCC2)n(C)c2cc(CC)n(CC(=O)c3ccccc3)c(=O)c12] | 10.4 | 100 | 464.2 |

TABLE 1-continued
| Ex. No. | structure | yield (mg) | purity (%) | MS (ESI+) |
|---|---|---|---|---|
| 16 | 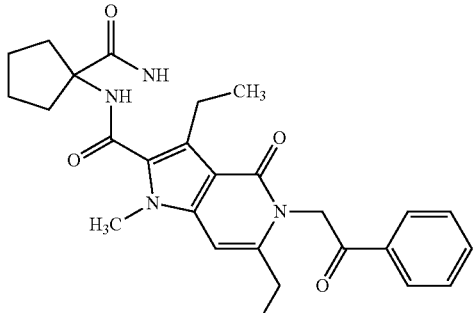 | 14.1 | 100 | 477.2 |
| 17 | 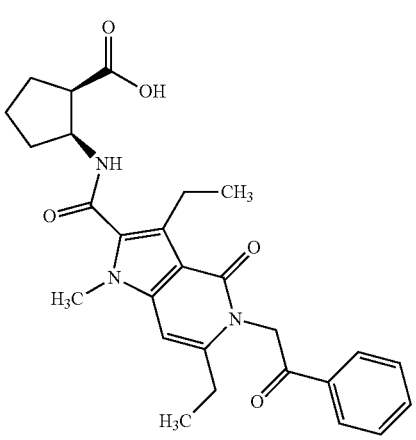 [SMILES: CCc1c(C(=O)N[C@H]2CCC[C@H]2C(=O)O)n(C)c2cc(CC)n(CC(=O)c3ccccc3)c(=O)c12] | 13.0 | 100 | 477.2 |
| 18 | 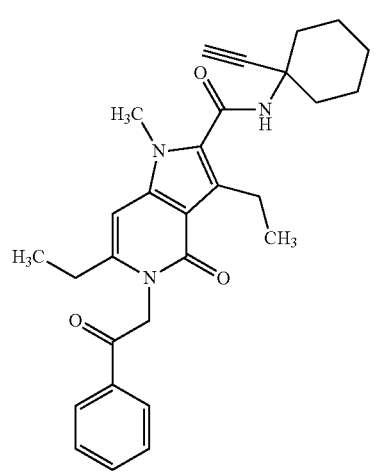 [SMILES: C#CC1(NC(=O)c2c(CC)c3c(=O)n(CC(=O)c4ccccc4)c(CC)cc3n2C)CCCCC1] | 4.7 | 100 | 472.2 |
| 19 | 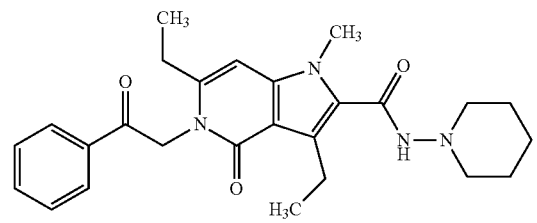 [SMILES: CCc1c(C(=O)NN2CCCCC2)n(C)c2cc(CC)n(CC(=O)c3ccccc3)c(=O)c12] | 2.1 | 100 | 449.2 |

TABLE 1-continued

| Ex. No. | structure | yield (mg) | purity (%) | MS (ESI+) |
|---|---|---|---|---|
| 20 | 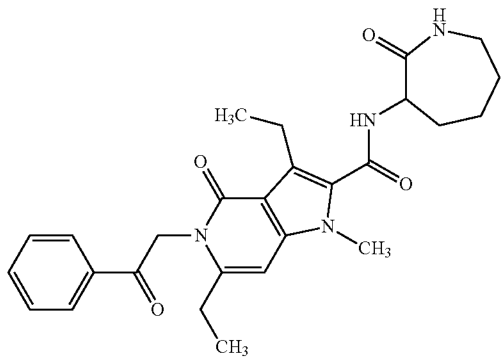 [SMILES: CCc1c(C(=O)NC2CCCCNC2=O)n(C)c2cc(CC)n(CC(=O)c3ccccc3)c(=O)c12] | 23.9 | 100 | 477.2 |
| 21 | 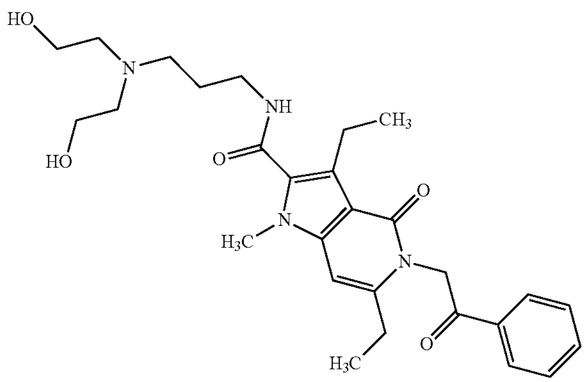 [SMILES: CCc1c(C(=O)NCCCN(CCO)CCO)n(C)c2cc(CC)n(CC(=O)c3ccccc3)c(=O)c12] | 15.2 | 100 | 511.3 |
| 22 | 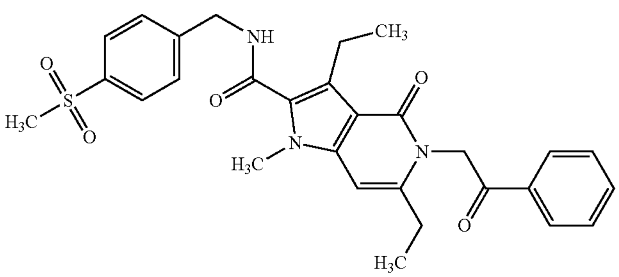 [SMILES: CCc1c(C(=O)NCc2ccc(S(C)(=O)=O)cc2)n(C)c2cc(CC)n(CC(=O)c3ccccc3)c(=O)c12] | 24.9 | 99 | 534.2 |
| 23 | 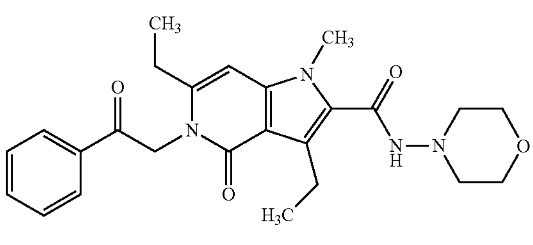 [SMILES: CCc1c(C(=O)NN2CCOCC2)n(C)c2cc(CC)n(CC(=O)c3ccccc3)c(=O)c12] | 4.6 | 100 | 451.2 |
| 24 | 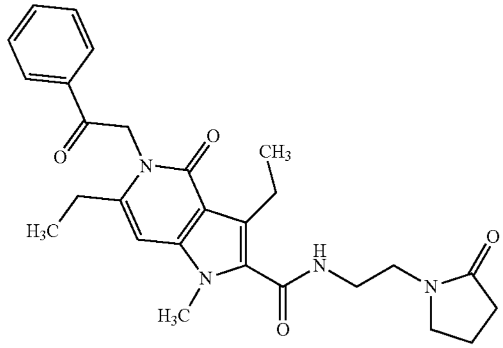 [SMILES: CCc1c(C(=O)NCCN2CCCC2=O)n(C)c2cc(CC)n(CC(=O)c3ccccc3)c(=O)c12] | 17.3 | 100 | 477.2 |

TABLE 1-continued

| Ex. No. | structure | yield (mg) | purity (%) | MS (ESI+) |
|---|---|---|---|---|
| 25 | 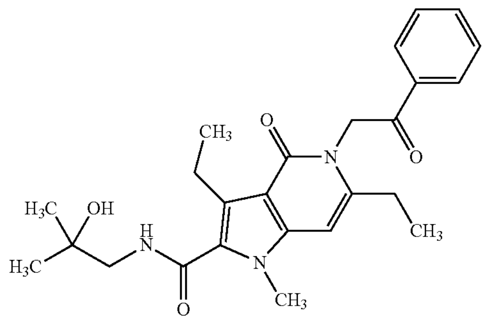 [SMILES: CCc1c(C(=O)NCC(C)(C)O)n(C)c2cc(CC)n(CC(=O)c3ccccc3)c(=O)c12] | 22.0 | 100 | 438.2 |
| 26 | 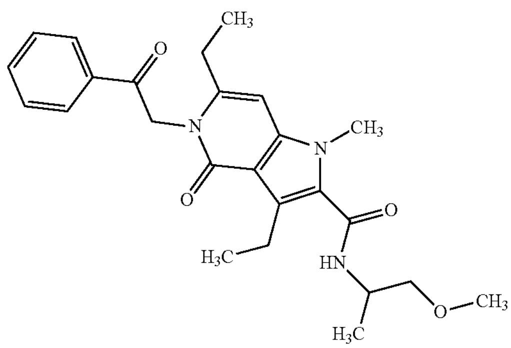 [SMILES: CCc1c(C(=O)NC(C)COC)n(C)c2cc(CC)n(CC(=O)c3ccccc3)c(=O)c12] | 21.8 | 99 | 438.2 |
| 27 | 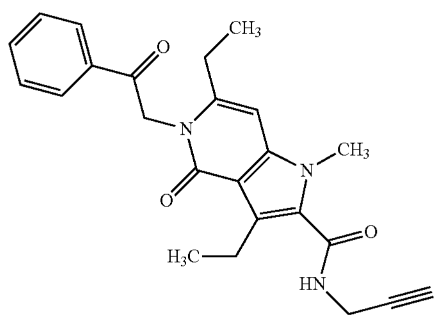 [SMILES: C#CCNC(=O)c1c(CC)c2c(=O)n(CC(=O)c3ccccc3)c(CC)cc2n1C] | 8.1 | 100 | 404.2 |
| 28 | 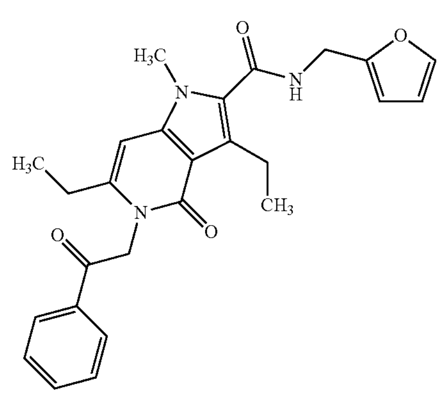 [SMILES: CCc1c(C(=O)NCc2ccco2)n(C)c2cc(CC)n(CC(=O)c3ccccc3)c(=O)c12] | 22.1 | 99 | 446.1 |

TABLE 1-continued

| Ex. No. | structure | yield (mg) | purity (%) | MS (ESI+) |
|---|---|---|---|---|
| 29 | 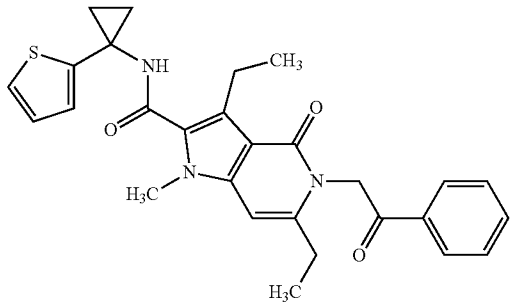 [SMILES: CCc1c(C(=O)NC2(c3cccs3)CC2)n(C)c2cc(CC)n(CC(=O)c3ccccc3)c(=O)c12] | 13.8 | 100 | 488.2 |
| 30 | 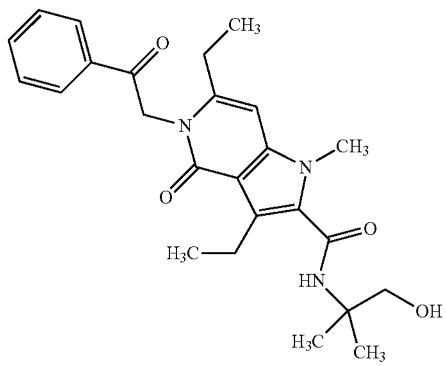 [SMILES: CCc1c(C(=O)NC(C)(C)CO)n(C)c2cc(CC)n(CC(=O)c3ccccc3)c(=O)c12] | 12.4 | 100 | 438.2 |

Example 31

Production of 3,6-diethyl-1-methyl-4-oxo-5-(2-oxo-2-phenylethyl)-N-(pyridin-4-yl)-4,5-dihydro-1H-pyrrolo[3,2-c]pyridine-2-carboxamide

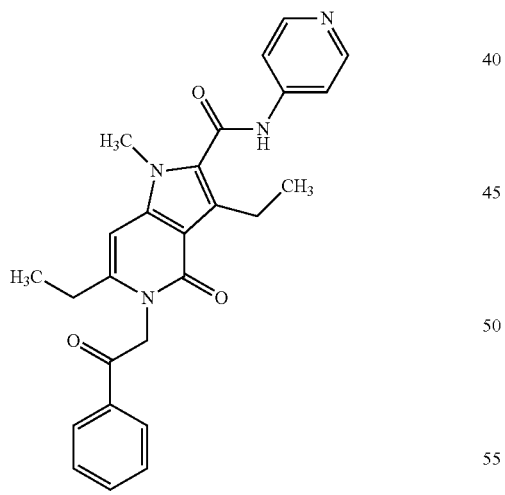

To a DMF solution (500 μL, 80 μmol) of pyridine-4-amine was added a 0.16M DMF solution (500 μL, 80 μmol) of the compound of Reference Example 10, and a DMF solution (500 μL) of HATU (160 μmol) and DIPEA (160 μmol) was added thereto. The reaction mixture was stirred at 70° C. overnight and extracted with ethyl acetate (3 mL) and 2% aqueous sodium hydrogen carbonate solution (2 mL). The organic layer was collected by upper layer PhaseSeptube (manufactured by Wako Pure Chemical Industries, Ltd.). Ethyl acetate was evaporated by blowing nitrogen against it, and the residue was dissolved in DMSO:acetonitrile (1:4) (1000 μL), and the solution was purified by preparative HPLC (acetonitrile-10 mM ammonium carbonate-containing water) to give the title compound.
yield: 0.9 mg
LC-MS analysis: purity 100%
MS (ESI+): 443.2 (M+H)

Example 32

Production of 6-ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

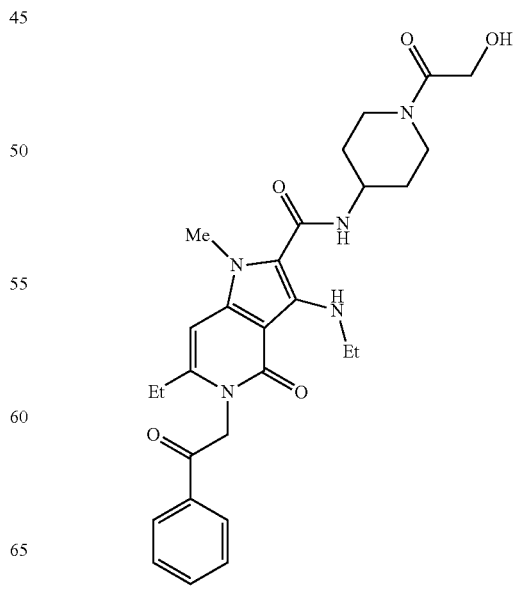

A mixture of the compound of Reference Example 25 (50 mg, 0.10 mmol), 2-(4-aminopiperidin-1-yl)-2-oxoethanol hydrochloride (24 mg, 0.13 mmol), HOBt (21 mg, 0.16 mmol), WSCD (30 mg, 0.16 mmol) and triethylamine (21 mg, 0.21 mmol) in DMF (2 ml) was stirred at room temperature for 2 days. The reaction mixture was diluted with saturated aqueous sodium hydrogen carbonate, and extracted twice with ethyl acetate. The extracts were combined, washed with brine, dried over magnesium sulfate, and concentrated under reduced pressure. The residue was purified by amino-silica gel column chromatography (eluate, ethyl acetate) to give 6-ethyl-3-[ethyl(trifluoroacetyl)amino]-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide (40 mg, 65%) as a colorless amorphous solid. A mixture of the 6-ethyl-3-[ethyl(trifluoroacetyl)amino]-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide (40 mg, 0.065 mmol) and potassium carbonate (18 mg, 0.13 mmol) in methanol (3 mL) was stirred at room temperature for 3 hr. Water (10 mL) was added to the reaction mixture, and the mixture was concentrated under reduced pressure. The residue was partitioned between ethyl acetate and saturated aqueous sodium hydrogen carbonate, and the organic layer was washed with brine, dried over magnesium sulfate, and concentrated under reduced pressure. The residue was recrystallized from ethyl acetate-hexane to give the title compound (22 mg, 65%) as beige crystals.

$^1$H NMR (300 MHz, DMSO-$d_6$) δ 1.08 (3H, t, J=6.9 Hz), 1.18 (3H, t, J=7.4 Hz), 1.27-1.50 (2H, m), 1.89 (2H, d, J=12.9 Hz), 2.56 (2H, q, J=7.0 Hz), 2.86 (1H, t, J=11.4 Hz), 2.95-3.05 (2H, m), 3.10 (1H, t, J=11.4 Hz), 3.66 (1H, d, J=11.7 Hz), 3.79 (3H, s), 3.99-4.14 (3H, m), 4.23 (1H, d, J=13.8 Hz), 4.51 (1H, t, J=5.4 Hz), 4.75 (1H, t, J=6.8 Hz), 5.57 (2H, s), 6.44 (1H, s), 7.60 (2H, t, J=7.5 Hz), 7.73 (1H, t, J=7.5 Hz), 8.09-8.12 (2H, m), 8.53 (1H, d, J=7.8 Hz).

Example 33

Production of 3-cyano-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

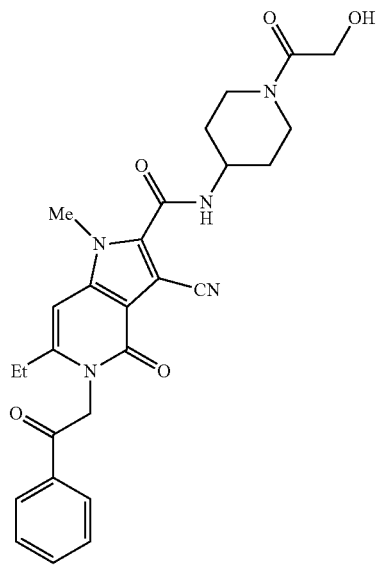 [SMILES: CCc1cc2c(c(C#N)c(C(=O)NC3CCN(C(=O)CO)CC3)n2C)c(=O)n1CC(=O)c1ccccc1]

A mixture of the compound of Reference Example 27 (16 mg, 0.044 mmol), 2-(4-aminopiperidin-1-yl)-2-oxoethanol hydrochloride (13 mg, 0.066 mmol), HOBt (9 mg, 0.066 mmol), WSCD (13 mg, 0.066 mmol) and triethylamine (13 mg, 0.13 mmol) in DMF (1 mL) was stirred at room temperature for 3 days. The reaction mixture was diluted with saturated aqueous sodium hydrogen carbonate, and extracted 3 times with ethyl acetate. The extracts were combined, washed with brine, dried over magnesium sulfate, and concentrated under reduced pressure. The residue was purified by amino-silica gel column chromatography (eluate, ethyl acetate, ethyl acetate/methanol=20/1-10/1), and recrystallized from ethyl acetate-hexane to give the title compound (17 mg, 77%) as white crystals.

$^1$H NMR (300 MHz, DMSO-$d_6$) δ 1.20 (3H, t, J=7.2 Hz), 1.30-1.60 (2H, m), 1.88 (2H, d, J=15.6 Hz), 2.63 (2H, q, J=7.2 Hz), 2.97 (1H, t, J=10.8 Hz), 3.14 (1H, t, J=11.6 Hz), 3.69 (1H, d, J=13.2 Hz), 3.83 (3H, s), 4.05-4.20 (4H, m), 4.54 (1H, t, J=5.4 Hz), 5.66 (2H, s), 6.64 (1H, s), 7.62 (2H, t, J=7.5 Hz), 7.75 (1H, t, J=7.5 Hz), 8.10-8.13 (2H, m), 8.93 (1H, d, J=7.5 Hz).

Formulation Example 1

A medicament containing the compound of the present invention as an active ingredient can be produced, for example, based on the following composition.

| 1. capsule | | |
|---|---|---|
| (1) | the compound obtained in Example 1 | 40 mg |
| (2) | lactose | 70 mg |
| (3) | crystalline cellulose | 9 mg |
| (4) | magnesium stearate | 1 mg |
| | 1 capsule | 120 mg |

(1), (2), (3) and ½ of (4) are blended and granulated. Thereto is added the rest of (4) and the total amount is filled in a gelatin capsule.

| 2. tablet | | |
|---|---|---|
| (1) | the compound obtained in Example 1 | 40 mg |
| (2) | lactose | 58 mg |
| (3) | cornstarch | 18 mg |
| (4) | crystalline cellulose | 3.5 mg |
| (5) | magnesium stearate | 0.5 mg |
| | 1 tablet | 120 mg |

(1), (2), (3), ⅔ of (4) and ½ of (5) are blended and granulated. Thereto is added the rest of (4) and (5) and the mixture is compression formed to give a tablet.

Formulation Example 2

The compound obtained in Example 1 (50 mg) is dissolved in the Japanese Pharmacopoeia distilled water for injection (50 ml), and the Japanese Pharmacopoeia distilled water for injection is added to 100 ml. The solution is filtered under sterile conditions, and 1 ml of the solution is filled in an injection vial under sterile conditions, and freeze-dried and sealed.

Genetic operation methods described in Experimental Examples below are based on the methods described in a book (Maniatis et al., Molecular Cloning, Cold Spring Harbor Laboratory, 1989), and the appended protocol of the reagent.

Experimental Example

1. Construction of Gli Reporter Plasmid

Gli reporter plasmid was constructed by inserting 8× Gli-binding site and chicken δ-crystalline promoter into the upstream of luc+ of pGL3 (Promega).

δ-Crystalline promoter was cloned by PCR method using, as a primer set, synthetic DNAs (SEQ ID NO: 1)
5'-GAAGATCTGCCAGCCCAGGCTCCGGGGC-3'

(SEQ ID NO: 2)
5'-CCCAAGCTTCTGCCCGCACAGCCCTGCTC-3' prepared in reference to the base sequence described in GenBank accession No.; X02187, and chicken genome DNA (Clontech) as a template. PCR reaction was performed using Pfu Turbo (Stratagene) and following the attached protocol. The obtained 108 bp fragment was digested with restriction enzymes BglII and HindIII, and inserted into BglII-HindIII site of pGL3 to give plasmid pGL3/δ-cry promoter.

As 8× Gli-binding site, a sequence containing eight 9-bp Gli bound consensus sequences (GACCACCCA) described in Yoon et al., J. Biol. Chem., vol. 273, pages 3496-3501 (1998) was prepared from synthetic DNA. That is, two synthetic DNAs, (SEQ ID NO: 3)
5'-GGGGTACCGACCACCCAGACCACCCAGACCACCCAGACCACCCA
GACCACCCAGACCACCCAGACCACCCAGACCACCCAAGATCTTC-3'

(SEQ ID NO: 4)
5'-GAAGATCTTGGGTGGTCTGGGTGGTCTGGGTGGTCTGGGTGGTC
TGGGTGGTCTGGGTGGTCTGGGTGGTCTGGGTGGTCGGTACCC-3' were heat treated at 95° C. for 2 minutes, and incubated at 37° C. for 1 hr for annealing to give a double stranded DNA of the above-mentioned two synthetic DNAs. The obtained double stranded DNA was digested with restriction enzymes BglII and KpnI, and the obtained DNA fragment was inserted into BglII-KpnI site of pGL3/δ-cry promoter to construct plasmid pGL3/δ-cry promoter, 8× Gli binding site, i.e., Gli reporter plasmid.

2. Construction of Plasmid for Expression of Mouse Shh-N End Fragment

As a material for construction of plasmid for Shh-N end fragment expression, mouse Shh cDNA was cloned at first.

The mouse Shh cDNA was cloned by Nested PCR method using mouse 11-day fetus cDNA (Clontech) as a template. The primer sequence was prepared in reference to the base sequence described in GenBank accession No.; NM_009170.

As the primer set for 1st PCR, (SEQ ID NO: 5)
5'-CTGGGTGGGGATCGGAGACA-3'

(SEQ ID NO: 6)
5'-GCGCTTTCCCATCAGTTCCTTATT-3' were used, and as the primer set for 2nd PCR, (SEQ ID NO: 7)
5'-GGGGTACCATGCTGCTGCTGCTGGCCA-3'

(SEQ ID NO: 8)
5'-GCTCTAGATCAGCTGGACTTGACCGCCA-3' were used. PCR reaction was performed using Pfu Turbo (Stratagene) and following the attached protocol. The resulting PCR product was cloned by pcDNA3.1 (+) (Invitrogen), and the inserted base sequence was confirmed.

Using the mouse Shh cDNA sequence obtained as mentioned above as a template, a partial cDNA sequence wherein stop codon (TGA) was added to 3'-terminal of cDNA sequence encoding 1st to 198th amino acid sequence of mouse Shh was obtained by PCR method. As the primer set, (SEQ ID NO: 9)
5'-ATGCTGCTGCTGCTGGCCAG-3'

(SEQ ID NO: 10)
5'-TCAGCCGCCGGATTTGGCCG-3' were used.

PCR reaction was performed using Pfu Turbo (Stratagene) and following the attached protocol. The obtained PCR product was cloned by pcDNA3.1 (+) (Invitrogen), and the inserted base sequence was confirmed.

In the manner mentioned above, a plasmid for mouse Shh-N end fragment expression, pcDNA3.1/mShh-N, was constructed.

3. Production of Recombinant Type Mouse Shh-N End Fragment

HEK293 cells were grown in D-MEM medium (Invitrogen) containing 10% fetal bovine serum in a 10 cm dish and pcDNA3.1/mShh-N was introduced into the cells using FuGENE6 (Roche Applied Science). Thereafter, the HEK293 cells were cultured in a carbon dioxide gas incubator at 37° C. for 24 hours, and the medium was exchanged with D-MEM medium (Invitrogen) containing 2% fetal bovine serum. After culturing for 48 hr, a culture supernatant containing recombinant type mouse Shh-N end fragment was obtained by filtration using a filter (0.22 μM).

4. Introduction of Plasmid for Gli-1 Expression and Reporter Plasmid into NIH-3T3 Cells and Production of Expressing Cells Using D-MEM (Invitrogen) containing 10% fetal bovine serum, expression plasmid pcDNA3.1 and Gli reporter plasmid (pGL3/δ-cry promoter, 8× Gli binding site) produced by the method of Experimental Example 1 were introduced into NIH-3T3 cells grown in a 10 cm dish by the use of FuGENE6 (Roche Applied Science).

After culture for 24 hr, the cells were recovered, suspended in D-MEM medium containing 10% fetal bovine serum and supplemented with Geneticin (Life Technologies Oriental, Inc.) to a final concentration of 500 μg/ml, diluted to $10^4$ cells/ml, plated on a 96 well plate, and cultured in a carbon dioxide gas incubator at 37° C. to give Geneticin resistant transformed cell line.

The obtained transformed cell line was cultured in a 96 well plate, mouse Shh-N end fragment obtained in Experimental Example 3 was added, and NIH-3T3/Gli reporter cell, which is a cell line capable of induction of luciferase expression, was selected.

5. Evaluation of Compound

NIH-3T3/Gli reporter cells cultured in D-MEM (Invitrogen) containing 10% fetal bovine serum were plated in a 96 well white plate at $1 \times 10^4$ cells/well, and cultured overnight in a carbon dioxide gas incubator at 37° C. The medium was removed, a compound (50 μl) and culture supernatant of mouse Shh-N end fragment-expressing HEK293 (D-MEM medium containing 2% fetal bovine serum, 50 μl) were added, and the cells were cultured for 48 hr in a carbon dioxide gas incubator at 37° C. Bright-Glo (Promega, 50 μl) was added, and the mixture was stirred, after which luciferase activity was measured by EnVision (PerkinElmer). The inhibition rate was calculated based on the luciferase activity of the control without addition of the compound as 100. The results are shown in Table 2 below.

TABLE 2

| Example | inhibitory rate (%) at 1 μM |
|---------|------------------------------|
| 1       | 100                          |
| 2       | 100                          |
| 32      | 98                           |

From the above-mentioned results, the compound of the present invention was shown to have a superior Smo inhibitory action.

INDUSTRIAL APPLICABILITY

Since the compound of the present invention shows a superior Smo inhibitory action, a clinically useful agent for the prophylaxis or treatment of diseases related to Smo (e.g., cancer etc.) can be provided. In addition, since the compound of the present invention is also superior in the efficacy expression, pharmacokinetics, solubility, interaction with other pharmaceutical products, safety and stability, it is useful as a medicament.

This application is based on patent application No. 2009-195784 filed in Japan, the contents of which are encompassed in full herein.

The invention claimed is:
1. A compound represented by formula (D1):

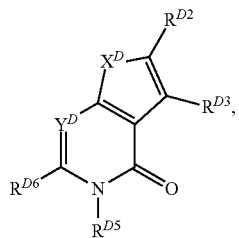

wherein
$X^D$ is $NR^{D1}$ wherein $R^{D1}$ is methyl;
$Y^D$ is $CR^{D7}$ wherein $R^{D7}$ is a hydrogen atom, or a nitrogen atom;
$R^{D2}$ is a carbamoyl group having 1 or 2 substituents selected from
(1) a 4- to 7-membered non-aromatic heterocyclic group optionally having 1 to 3 substituents selected from
 (a) a $C_{1-6}$ alkyl group optionally having 1 to 3 hydroxy groups,
 (b) a $C_{1-6}$ alkyl-carbonyl group optionally having 1 to 3 hydroxy groups, and
 (c) an oxo group;
(2) a $C_{3-8}$ cycloalkyl group optionally having 1 to 3 substituents selected from
 (a) a hydroxy group,
 (b) a $C_{1-6}$ alkyl group optionally having 1 to 3 hydroxy groups,
 (c) a carbamoyl group,
 (d) a $C_{2-6}$ alkynyl group, and
 (e) a 5- to 6-membered aromatic heterocyclic group;
(3) a $C_{1-6}$ alkyl group having one substituent selected from
 (a) a $C_{1-6}$ alkylsulfonyl group optionally having 1 to 3 $C_{1-6}$ alkoxy groups,
 (b) an amino group having one $C_{1-6}$ alkyl-carbonyl group optionally having 1 to 3 hydroxy groups,
 (c) an amino group having 1 or 2 $C_{1-6}$ alkyl groups optionally having 1 to 3 hydroxy groups,
 (d) a $C_{6-10}$ aryl group optionally having 1 to 3 $C_{1-6}$ alkylsulfonyl groups,
 (e) a 4- to 7-membered non-aromatic heterocyclic group optionally having 1 to 3 oxo groups,
 (f) a 5- to 6-membered aromatic heterocyclic group,
 (g) a hydroxy group, and
 (h) a $C_{1-6}$ alkoxy group;
(4) a 5- to 6-membered aromatic heterocyclic group; and
(5) a $C_{2-6}$ alkynyl group;
$R^{D3}$ is a $C_{1-6}$ alkyl group or a $C_{2-6}$ alkenyl group;
$R^{D5}$ is
(1) a $C_{1-6}$ alkyl group optionally having 1 to 3 substituents selected from
 (a) a $C_{6-10}$ aryl-carbonyl group,
 (b) a $C_{6-10}$ aryl group optionally having 1 to 3 substituents selected from
  (i) a halogen atom, and
  (ii) a $C_{1-6}$ alkoxy group, and
 (c) a $C_{1-6}$ alkoxy group optionally having 1 to 3 $C_{6-10}$ aryl groups;
(2) a $C_{6-10}$ aryl group optionally having 1 to 3 substituents selected from
 (a) a halogen atom,
 (b) a $C_{1-6}$ alkyl group optionally having 1 to 3 halogen atoms, and
 (c) a $C_{1-6}$ alkoxy group; or
(3) a 5- or 6-membered monocyclic aromatic heterocyclic group optionally having 1 to 3 substituents selected from
 (a) a halogen atom,
 (b) a $C_{1-6}$ alkyl group, and
 (c) a $C_{1-6}$ alkoxy group; and
$R^{D6}$ is a $C_{1-6}$ alkyl group,
or a salt thereof.

2. The compound or salt of claim 1, wherein $Y^D$ is $CR^{D7}$, wherein $R^{D7}$ is a hydrogen atom.

3. 3,6-Diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof.

4. 3-Ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof.

5. 6-Ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof.

6. A pharmaceutical composition comprising the compound or salt of claim 1 and at least one pharmacologically acceptable carrier.

7. The pharmaceutical composition of claim 6, which is an Smo inhibitor.

8. A pharmaceutical composition comprising the compound or salt of claim 3 and at least one pharmacologically acceptable carrier.

9. A pharmaceutical composition comprising the compound or salt of claim 4 and at least one pharmacologically acceptable carrier.

10. A pharmaceutical composition comprising the compound or salt of claim 5 and at least one pharmacologically acceptable carrier.

* * * * *